United States Patent
Luo et al.

(10) Patent No.: US 12,410,239 B2
(45) Date of Patent: Sep. 9, 2025

(54) ANTI-HEPATITIS B VIRUS ANTIBODY AND USES THEREOF

(71) Applicants: XIAMEN UNIVERSITY, Xiamen (CN); YANG SHENG TANG COMPANY, LTD., Hangzhou (CN)

(72) Inventors: Wenxin Luo, Xiamen (CN); Can Wen, Xiamen (CN); Xinchu Xiang, Xiamen (CN); Jixian Tang, Xiamen (CN); Yangtao Wu, Xiamen (CN); Tianying Zhang, Xiamen (CN); Quan Yuan, Xiamen (CN); Ningshao Xia, Xiamen (CN)

(73) Assignees: XIAMEN UNIVERSITY, Xiamen (CN); YANG SHENG TANG COMPANY, LTD., Hangzhou (CN)

( * ) Notice: Subject to any disclaimer, the term of this patent is extended or adjusted under 35 U.S.C. 154(b) by 961 days.

(21) Appl. No.: 17/613,322

(22) PCT Filed: May 22, 2020

(86) PCT No.: PCT/CN2020/091739
§ 371 (c)(1),
(2) Date: Nov. 22, 2021

(87) PCT Pub. No.: WO2020/233695
PCT Pub. Date: Nov. 26, 2020

(65) Prior Publication Data
US 2022/0235117 A1   Jul. 28, 2022

(30) Foreign Application Priority Data

May 23, 2019  (CN) .......................... 201910432602.7

(51) Int. Cl.
*C07K 16/08*  (2006.01)
*A61K 39/00*  (2006.01)
*A61P 31/20*  (2006.01)

(52) U.S. Cl.
CPC ............ *C07K 16/082* (2013.01); *A61P 31/20* (2018.01); *A61K 2039/505* (2013.01); *A61K 2039/575* (2013.01); *C07K 2317/24* (2013.01); *C07K 2317/515* (2013.01); *C07K 2317/52* (2013.01); *C07K 2317/56* (2013.01); *C07K 2317/565* (2013.01); *C07K 2317/567* (2013.01); *C07K 2317/622* (2013.01); *C07K 2317/76* (2013.01); *C07K 2317/92* (2013.01)

(58) Field of Classification Search
CPC .............. C07K 16/082; C07K 2317/24; C07K 2317/515; C07K 2317/52; C07K 2317/56; C07K 2317/565; C07K 2317/567; C07K 2317/622; C07K 2317/76; C07K 2317/92; A61P 31/20; A61K 2039/505; A61K 2039/575

See application file for complete search history.

(56) References Cited

U.S. PATENT DOCUMENTS

| | | |
|---|---|---|
| 9,751,914 B2 | 9/2017 | Yuan et al. |
| 10,246,494 B2 | 4/2019 | Yuan et al. |
| 10,548,973 B2 | 2/2020 | Zhang et al. |
| 10,556,949 B2 | 2/2020 | Igawa et al. |
| 2011/0111406 A1 | 5/2011 | Igawa et al. |
| 2012/0264921 A1 | 10/2012 | Kim et al. |
| 2014/0255398 A1 | 9/2014 | Igawa et al. |
| 2015/0050269 A1 | 2/2015 | Igawa et al. |
| 2015/0246948 A1 | 9/2015 | Yuan et al. |
| 2017/0022270 A1 | 1/2017 | Igawa et al. |
| 2017/0326231 A1 | 11/2017 | Yoon et al. |
| 2018/0002382 A1 | 1/2018 | Yuan et al. |
| 2018/0037634 A1 | 2/2018 | Viswanathan et al. |
| 2019/0185557 A1 | 6/2019 | Igawa et al. |

(Continued)

FOREIGN PATENT DOCUMENTS

| | | |
|---|---|---|
| CN | 102906111 A | 1/2013 |
| CN | 103483421 A | 1/2014 |

(Continued)

OTHER PUBLICATIONS

Rudikoff S, Giusti AM, Cook WD, Scharff MD. Single amino acid substitution altering antigen-binding specificity. Proc Natl Acad Sci USA. Mar. 1982;79(6):1979-83. (Year: 1982).*

International Search Report issued on Aug. 24, 2020 in PCT/CN2020/091739 filed on May 22, 2020, citing documents AA-AC, AO-AR, AX and AY therein, 5 pages.

Wen, C. et al., "Advance in research on recycling antibody," Chin. J. Biotech., vol. 35, No. 2, 2019, pp. 183-194 (with English abstract).

Yang, D. et al., "Maximizing in vivo target clearance by design of pH-dependent target binding antibodies with altered affinity to FcRn," MABS, vol. 9, No. 7, 2017, pp. 1105-1117.

(Continued)

*Primary Examiner* — Nicole Kinsey White
*Assistant Examiner* — Ruixue Wang
(74) *Attorney, Agent, or Firm* — Oblon, McClelland, Maier &Neustadt, L.L.P.

(57) ABSTRACT

Disclosed are antibodies to anti-hepatitis B surface antigen (HBsAg) (especially humanized antibodies), nucleic acid molecules encoding same, methods for preparing same, and pharmaceutical compositions containing same. The antibodies have higher affinity for HBsAg at neutral pH than at acidic pH, thereby significantly enhancing the virus clearance efficiency and prolonging the virus inhibition time. The antibodies and the pharmaceutical compositions can be used for preventing and/or treating HBV infections or diseases related to HBV infections (e.g., hepatitis B), for neutralizing the virulence of HBV in a subject (e.g., a human), for reducing the serum level of HBV DNA and/or HBsAg in the body of the subject, or for activating the humoral immune response of the subject (e.g., a chronic HBV infected or chronic hepatitis B patient) against HBV.

17 Claims, 15 Drawing Sheets

Specification includes a Sequence Listing.

(56) References Cited

U.S. PATENT DOCUMENTS

| | | |
|---|---|---|
| 2019/0247494 A1 | 8/2019 | Zhang et al. |
| 2019/0389939 A1 | 12/2019 | Luo et al. |
| 2020/0115447 A1 | 4/2020 | Igawa et al. |
| 2020/0147205 A1 | 5/2020 | Zhang et al. |

FOREIGN PATENT DOCUMENTS

| | | |
|---|---|---|
| CN | 104093424 A | 10/2014 |
| CN | 106046155 A | 10/2016 |
| CN | 106480070 A | 3/2017 |
| CN | 106565840 A | 4/2017 |
| CN | 108456686 A | 8/2018 |
| CN | 108690134 A | 10/2018 |
| CN | 109414496 A | 3/2019 |
| EP | 2 762 493 A1 | 8/2014 |
| JP | 2000-253878 A | 9/2000 |
| JP | 2012-521772 A | 9/2012 |
| JP | 2017-536832 A | 12/2017 |
| KR | 10-2018-0084045 A | 7/2018 |
| RU | 2 616 236 C1 | 4/2017 |
| WO | WO 2009/125825 A1 | 10/2009 |
| WO | WO 2010/112316 A1 | 10/2010 |
| WO | WO 2013/047729 A1 | 4/2013 |
| WO | WO 2013/047748 A1 | 4/2013 |
| WO | WO 2017/176319 A1 | 10/2017 |
| WO | WO 2018/052556 A1 | 3/2018 |
| WO | WO 2018/184593 A1 | 10/2018 |
| WO | WO 2018/195165 A1 | 10/2018 |
| WO | WO 2018/206748 A1 | 11/2018 |

OTHER PUBLICATIONS

Bonvin et al., "De novo isolation of antibodies with pH-dependent binding properties", mAbs, vol. 7, Issue 2, Mar./Apr. 2015, pp. 294-302.

Japanese Office Action issued Jun. 4, 2024 in Japanese Patent Application No. 2021-569886 (with English Translation), citing reference 15 therein, 12 pages.

Korean Office Action issued May 20, 2024 in Korean Patent Application No. 10-2021-7041773 (with English Translation), citing reference 16 therein, 25 pages.

International Search Report issued on Aug. 26, 2020 in PCT/CN2020/091890 filed May 22, 2020 citing documents AA-AK, AO-AS and AX-AZ therein, 22 total pages (with English translation).

Xu, L., et al., "Humanization of Therapeutic Antibody of One Hepatitis B Virus and Identification of Its Biological Activity", Journal of Xiamen University (Natural Science), vol. 56, No. 1, 2017, pp. 72-78 (with English abstract).

Chaouch, H., et al., "Naturally Occurring Surface Antigen Variants of Hepatitis B Virus in Tunisian Patients" Intervirology, vol. 59, 2016, pp. 36-47.

Kang, X., et al., "Single-domain antibody—advances in research and application", Chinese Journal of Biotechnology, vol. 34, No. 12, 2018, pp. 1974-1984 (with English abstract).

* cited by examiner

|  | HCDR1 | HCDR2 | HCDR3 | LCDR1 | LCDR3 |
|---|---|---|---|---|---|
| M1D | GGSITSNFW (SEQ ID NO: 20) | SGSGTYT (SEQ ID NO: 21) | ARSHDYGSNDYAFDF (SEQ ID NO: 16) | QDISSS (SEQ ID NO: 11) | QQYHSLPLT (SEQ ID NO: 46) |
| A31-73 | GGSIHSNFW (SEQ ID NO: 8) | SGPGHHT (SEQ ID NO: 9) | ARSHDYGHHDYAFDF (SEQ ID NO:10) | - | QQYHYLPLT (SEQ ID NO: 13) |
| A42-12 | GGSIHHNFW (SEQ ID NO: 14) | HGPGHYT (SEQ ID NO: 15) | - | - | QQYHYLPLT (SEQ ID NO: 13) |
| A41-8 | - | - | ARSHHYGSNDYAFDF (SEQ ID NO: 22) | QDISYS (SEQ ID NO: 23) | QQYHYLPLT (SEQ ID NO: 13) |
| A42-23 | GGSITHNFW (SEQ ID NO: 17) | SGYDTYT (SEQ ID NO: 18) | ARSHDYGHHDYAFDF (SEQ ID NO: 10) | QDIHHS (SEQ ID NO: 19) | QQYHYLPLT (SEQ ID NO: 13) |

FIG.5

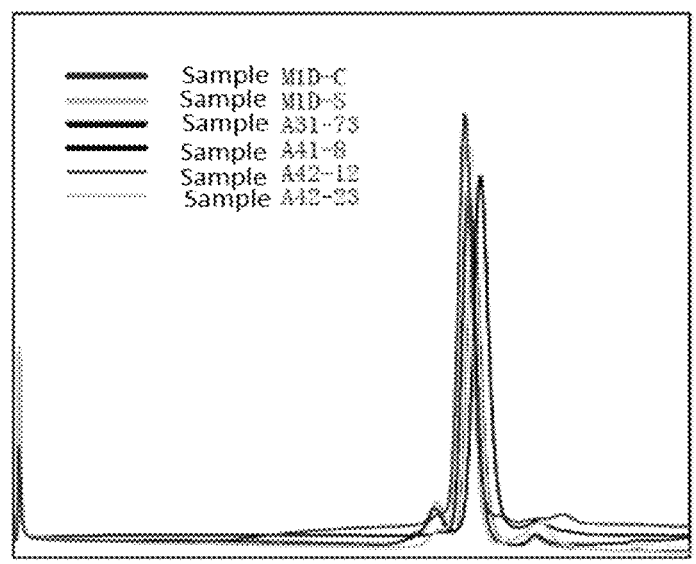

FIG.6

SEQUENCE LISTING

```
<160> NUMBER OF SEQ ID NOS: 58

<210> SEQ ID NO 1
<211> LENGTH: 122
<212> TYPE: PRT
<213> ORGANISM: Artificial sequence
<220> FEATURE:
<223> OTHER INFORMATION: A31-73 VH

<400> SEQUENCE: 1

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile His Ser Asn
```

```
                    20                  25                  30
Phe Trp Ser Trp Ile Arg Gln Pro Pro Gly Lys Gly Leu Glu Trp Ile
                35                  40                  45
Gly Tyr Ile Ser Gly Pro Gly His His Thr Asp Tyr Asn Pro Ser Leu
            50                  55                  60
Lys Ser Arg Val Thr Ile Ser Val Asp Thr Ser Lys Asn Gln Phe Ser
65                  70                  75                  80
Leu Lys Leu Ser Ser Val Thr Ala Ala Asp Thr Ala Val Tyr Tyr Cys
                85                  90                  95
Ala Arg Ser His Asp Tyr Gly His His Asp Tyr Ala Phe Asp Phe Trp
                100                 105                 110
Gly Gln Gly Thr Thr Val Thr Val Ser Ser
            115                 120

<210> SEQ ID NO 2
<211> LENGTH: 107
<212> TYPE: PRT
<213> ORGANISM: Artificial sequence
<220> FEATURE:
<223> OTHER INFORMATION: A31-73/A42-12  VK

<400> SEQUENCE: 2

Asp Ile Gln Met Thr Gln Ser Pro Ser Ser Leu Ser Ala Ser Val Gly
1               5                   10                  15
Asp Arg Val Thr Ile Thr Cys Arg Ala Thr Gln Asp Ile Ser Ser Ser
                20                  25                  30
Leu Asn Trp Tyr Gln Leu Lys Pro Gly Lys Ala Pro Lys Leu Leu Ile
                35                  40                  45
Tyr Tyr Ala Asn Arg Leu Gln Ser Gly Val Pro Ser Arg Phe Ser Gly
            50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr His Tyr Leu Pro Leu
                85                  90                  95
Thr Phe Gly Gly Gly Thr Lys Val Glu Ile Lys
                100                 105

<210> SEQ ID NO 3
<211> LENGTH: 122
<212> TYPE: PRT
<213> ORGANISM: Artificial sequence
<220> FEATURE:
<223> OTHER INFORMATION: A42-12 VH

<400> SEQUENCE: 3

Gln Val Gln Leu Gln Glu Ser Gly Pro Gly Leu Val Lys Pro Ser Glu
1               5                   10                  15
Thr Leu Ser Leu Thr Cys Thr Val Ser Gly Gly Ser Ile His His Asn
                20                  25                  30
Phe Trp Ser Trp Ile Arg Gln Pro Pro Gly Lys Gly Leu Glu Trp Ile
                35                  40                  45
Gly Tyr Ile His Gly Pro Gly His Tyr Thr Asp Tyr Asn Pro Ser Leu
            50                  55                  60
Lys Ser Arg Val Thr Ile Ser Val Asp Thr Ser Lys Asn Gln Phe Ser
65                  70                  75                  80
Leu Lys Leu Ser Ser Val Thr Ala Ala Asp Thr Ala Val Tyr Tyr Cys
                85                  90                  95
```

```
Ala Arg Ser His Asp Tyr Gly Ser Asn Asp Tyr Ala Phe Asp Phe Trp
            100                 105                 110

Gly Gln Gly Thr Thr Val Thr Val Ser Ser
        115                 120
```

<210> SEQ ID NO 4
<211> LENGTH: 122
<212> TYPE: PRT
<213> ORGANISM: Artificial sequence
<220> FEATURE:
<223> OTHER INFORMATION: A42-23 VH

<400> SEQUENCE: 4

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Thr His Asn
            20                  25                  30

Phe Trp Ser Trp Ile Arg Gln Pro Pro Gly Lys Gly Leu Glu Trp Ile
            35                  40                  45

Gly Tyr Ile Ser Gly Tyr Asp Thr Tyr Thr Asp Tyr Asn Pro Ser Leu
        50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
            85                  90                  95

Ala Arg Ser His Asp Tyr Gly His His Asp Tyr Ala Phe Asp Phe Trp
            100                 105                 110

Gly Gln Gly Thr Thr Val Thr Val Ser Ser
        115                 120
```

<210> SEQ ID NO 5
<211> LENGTH: 107
<212> TYPE: PRT
<213> ORGANISM: Artificial sequence
<220> FEATURE:
<223> OTHER INFORMATION: A42-23 VK

<400> SEQUENCE: 5

```
Asp Ile Gln Met Thr Gln Ser Pro Ser Ser Leu Ser Ala Ser Val Gly
1               5                   10                  15

Asp Arg Val Thr Ile Thr Cys Arg Ala Thr Gln Asp Ile His His Ser
            20                  25                  30

Leu Asn Trp Tyr Gln Gln Lys Pro Gly Lys Ala Pro Lys Leu Leu Ile
            35                  40                  45

Tyr Tyr Ala Asn Arg Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr His Tyr Leu Pro Leu
            85                  90                  95

Thr Phe Gly Gly Gly Thr Lys Val Glu Ile Lys
        100                 105
```

<210> SEQ ID NO 6
<211> LENGTH: 122
<212> TYPE: PRT
<213> ORGANISM: Artificial sequence
<220> FEATURE:
<223> OTHER INFORMATION: A41-8 VH

```
<400> SEQUENCE: 6

Gln Val Gln Leu Gln Glu Ser Gly Pro Gly Leu Val Lys Pro Ser Glu
1               5                   10                  15

Thr Leu Ser Leu Thr Cys Thr Val Ser Gly Ser Ile Thr Ser Asn
            20                  25                  30

Phe Trp Ser Trp Ile Arg Gln Pro Pro Gly Lys Gly Leu Glu Trp Ile
            35                  40                  45

Gly Tyr Ile Ser Gly Ser Gly Thr Tyr Thr Asp Tyr Asn Pro Ser Leu
        50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser His His Tyr Gly Ser Asn Asp Tyr Ala Phe Asp Phe Trp
            100                 105                 110

Gly Gln Gly Thr Thr Val Thr Val Ser Ser
        115                 120

<210> SEQ ID NO 7
<211> LENGTH: 107
<212> TYPE: PRT
<213> ORGANISM: Artificial sequence
<220> FEATURE:
<223> OTHER INFORMATION: A41-8 VK

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Thr Gln Asp Ile Ser Tyr Ser
            20                  25                  30

Leu Asn Trp Tyr Gln Gln Lys Pro Gly Lys Ala Pro Lys Leu Leu Ile
            35                  40                  45

Tyr Tyr Ala Asn Arg Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr His Tyr Leu Pro Leu
                85                  90                  95

Thr Phe Gly Gly Gly Thr Lys Val Glu Ile Lys
            100                 105

<210> SEQ ID NO 8
<211> LENGTH: 9
<212> TYPE: PRT
<213> ORGANISM: Artificial sequence
<220> FEATURE:
<223> OTHER INFORMATION: A31-73 HCDR1

<400> SEQUENCE: 8

Gly Gly Ser Ile His Ser Asn Phe Trp
1               5

<210> SEQ ID NO 9
<211> LENGTH: 7
<212> TYPE: PRT
<213> ORGANISM: Artificial sequence
<220> FEATURE:
<223> OTHER INFORMATION: A31-73 HCDR2

<400> SEQUENCE: 9
```

```
Ser Gly Pro Gly His His Thr
1               5
```

<210> SEQ ID NO 10
<211> LENGTH: 15
<212> TYPE: PRT
<213> ORGANISM: Artificial sequence
<220> FEATURE:
<223> OTHER INFORMATION: A31-73/A42-23 HCDR3

<400> SEQUENCE: 10

```
Ala Arg Ser His Asp Tyr Gly His His Asp Tyr Ala Phe Asp Phe
1               5                   10                  15
```

<210> SEQ ID NO 11
<211> LENGTH: 6
<212> TYPE: PRT
<213> ORGANISM: Artificial sequence
<220> FEATURE:
<223> OTHER INFORMATION: M1D/A31-73/A42-12 LCDR1

<400> SEQUENCE: 11

```
Gln Asp Ile Ser Ser Ser
1               5
```

<210> SEQ ID NO 12
<211> LENGTH: 3
<212> TYPE: PRT
<213> ORGANISM: Artificial sequence
<220> FEATURE:
<223> OTHER INFORMATION: M1D/A31-73/A42-12/A42-23/A41-8 LCDR2

<400> SEQUENCE: 12

```
Tyr Ala Asn
1
```

<210> SEQ ID NO 13
<211> LENGTH: 9
<212> TYPE: PRT
<213> ORGANISM: Artificial sequence
<220> FEATURE:
<223> OTHER INFORMATION: A31-73/A42-12/A42-23/A41-8 LCDR3

<400> SEQUENCE: 13

```
Gln Gln Tyr His Tyr Leu Pro Leu Thr
1               5
```

<210> SEQ ID NO 14
<211> LENGTH: 9
<212> TYPE: PRT
<213> ORGANISM: Artificial sequence
<220> FEATURE:
<223> OTHER INFORMATION: A42-12 HCDR1

<400> SEQUENCE: 14

```
Gly Gly Ser Ile His His Asn Phe Trp
1               5
```

<210> SEQ ID NO 15
<211> LENGTH: 7
<212> TYPE: PRT
<213> ORGANISM: Artificial sequence
<220> FEATURE:
<223> OTHER INFORMATION: A42-12 HCDR2

<400> SEQUENCE: 15

His Gly Pro Gly His Tyr Thr
1               5

<210> SEQ ID NO 16
<211> LENGTH: 15
<212> TYPE: PRT
<213> ORGANISM: Artificial sequence
<220> FEATURE:
<223> OTHER INFORMATION: M1D/A42-12 HCDR3

<400> SEQUENCE: 16

Ala Arg Ser His Asp Tyr Gly Ser Asn Asp Tyr Ala Phe Asp Phe
1               5                   10                  15

<210> SEQ ID NO 17
<211> LENGTH: 9
<212> TYPE: PRT
<213> ORGANISM: Artificial sequence
<220> FEATURE:
<223> OTHER INFORMATION: A42-23 HCDR1

<400> SEQUENCE: 17

Gly Gly Ser Ile Thr His Asn Phe Trp
1               5

<210> SEQ ID NO 18
<211> LENGTH: 7
<212> TYPE: PRT
<213> ORGANISM: Artificial sequence
<220> FEATURE:
<223> OTHER INFORMATION: A42-23 HCDR2

<400> SEQUENCE: 18

Ser Gly Tyr Asp Thr Tyr Thr
1               5

<210> SEQ ID NO 19
<211> LENGTH: 6
<212> TYPE: PRT
<213> ORGANISM: Artificial sequence
<220> FEATURE:
<223> OTHER INFORMATION: A42-23 LCDR1

<400> SEQUENCE: 19

Gln Asp Ile His His Ser
1               5

<210> SEQ ID NO 20
<211> LENGTH: 9
<212> TYPE: PRT
<213> ORGANISM: Artificial sequence
<220> FEATURE:
<223> OTHER INFORMATION: M1D/A41-8 HCDR1

<400> SEQUENCE: 20

Gly Gly Ser Ile Thr Ser Asn Phe Trp
1               5

<210> SEQ ID NO 21
<211> LENGTH: 7
<212> TYPE: PRT
<213> ORGANISM: Artificial sequence
<220> FEATURE:
<223> OTHER INFORMATION: M1D/A41-8 HCDR2

<400> SEQUENCE: 21

Ser Gly Ser Gly Thr Tyr Thr

```
<210> SEQ ID NO 22
<211> LENGTH: 15
<212> TYPE: PRT
<213> ORGANISM: Artificial sequence
<220> FEATURE:
<223> OTHER INFORMATION: A41-8 HCDR3

<400> SEQUENCE: 22

Ala Arg Ser His His Tyr Gly Ser Asn Asp Tyr Ala Phe Asp Phe
1               5                   10                  15

<210> SEQ ID NO 23
<211> LENGTH: 6
<212> TYPE: PRT
<213> ORGANISM: Artificial sequence
<220> FEATURE:
<223> OTHER INFORMATION: A41-8 LCDR1

<400> SEQUENCE: 23

Gln Asp Ile Ser Tyr Ser
1               5

<210> SEQ ID NO 24
<211> LENGTH: 25
<212> TYPE: PRT
<213> ORGANISM: Artificial sequence
<220> FEATURE:
<223> OTHER INFORMATION: M1D HFR1

<400> SEQUENCE: 24

Gln Val Gln Leu Gln Glu Ser Gly Pro Gly Leu Val Lys Pro Ser Glu
1               5                   10                  15

Thr Leu Ser Leu Thr Cys Thr Val Ser
            20                  25

<210> SEQ ID NO 25
<211> LENGTH: 17
<212> TYPE: PRT
<213> ORGANISM: Artificial sequence
<220> FEATURE:
<223> OTHER INFORMATION: M1D HFR2

<400> SEQUENCE: 25

Ser Trp Ile Arg Gln Pro Pro Gly Lys Gly Leu Glu Trp Ile Gly Tyr
1               5                   10                  15

Ile

<210> SEQ ID NO 26
<211> LENGTH: 38
<212> TYPE: PRT
<213> ORGANISM: Artificial sequence
<220> FEATURE:
<223> OTHER INFORMATION: M1D HFR3

<400> SEQUENCE: 26

Asp Tyr Asn Pro Ser Leu Lys Ser Arg Val Thr Ile Ser Val Asp Thr
1               5                   10                  15

Ser Lys Asn Gln Phe Ser Leu Lys Leu Ser Ser Val Thr Ala Ala Asp
            20                  25                  30

Thr Ala Val Tyr Tyr Cys
            35
```

```
<210> SEQ ID NO 27
<211> LENGTH: 11
<212> TYPE: PRT
<213> ORGANISM: Artificial sequence
<220> FEATURE:
<223> OTHER INFORMATION: M1D HFR4

<400> SEQUENCE: 27

Trp Gly Gln Gly Thr Thr Val Thr Val Ser Ser
1               5                   10

<210> SEQ ID NO 28
<211> LENGTH: 26
<212> TYPE: PRT
<213> ORGANISM: Artificial sequence
<220> FEATURE:
<223> OTHER INFORMATION: M1D LFR1

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Arg Ala Thr
            20                  25

<210> SEQ ID NO 29
<211> LENGTH: 17
<212> TYPE: PRT
<213> ORGANISM: Artificial sequence
<220> FEATURE:
<223> OTHER INFORMATION: M1D LFR2

<400> SEQUENCE: 29

Leu Asn Trp Tyr Gln Gln Lys Pro Gly Lys Ala Pro Lys Leu Leu Ile
1               5                   10                  15

Tyr

<210> SEQ ID NO 30
<211> LENGTH: 36
<212> TYPE: PRT
<213> ORGANISM: Artificial sequence
<220> FEATURE:
<223> OTHER INFORMATION: M1D LFR3

<400> SEQUENCE: 30

Arg Leu Gln Ser Gly Val Pro Ser Arg Phe Ser Gly Ser Gly Ser Gly
1               5                   10                  15

Thr Asp Phe Thr Leu Thr Ile Ser Ser Leu Gln Pro Glu Asp Phe Ala
            20                  25                  30

Thr Tyr Tyr Cys
        35

<210> SEQ ID NO 31
<211> LENGTH: 10
<212> TYPE: PRT
<213> ORGANISM: Artificial sequence
<220> FEATURE:
<223> OTHER INFORMATION: M1D LFR4

<400> SEQUENCE: 31

Phe Gly Gly Gly Thr Lys Val Glu Ile Lys
1               5                   10

<210> SEQ ID NO 32
<211> LENGTH: 49
<212> TYPE: DNA
```

```
<213> ORGANISM: Artificial sequence
<220> FEATURE:
<223> OTHER INFORMATION: Primer

<400> SEQUENCE: 32
gttattactc gtggcccagc cggccatggc acaggtgcag ctgcaggag          49

<210> SEQ ID NO 33
<211> LENGTH: 71
<212> TYPE: DNA
<213> ORGANISM: Artificial sequence
<220> FEATURE:
<223> OTHER INFORMATION: Primer

<400> SEQUENCE: 33
cactccagac ccttccctgg gggctggcgg atccagctcc agaagttgyk gkkgatgykg    60
ysgysagaga c                                                        71

<210> SEQ ID NO 34
<211> LENGTH: 68
<212> TYPE: DNA
<213> ORGANISM: Artificial sequence
<220> FEATURE:
<223> OTHER INFORMATION: Primer

<400> SEQUENCE: 34
ccagggaagg gtctggagtg gattgggtat atcymtggty mtsrtmmtya tmmcgactac    60
aacccctc                                                            68

<210> SEQ ID NO 35
<211> LENGTH: 67
<212> TYPE: DNA
<213> ORGANISM: Artificial sequence
<220> FEATURE:
<223> OTHER INFORMATION: Primer

<400> SEQUENCE: 35
cccttggccc cagaaatcaa aagcgtrgts gtkgykgysg trgtsgtgcg atctcgcaca    60
gtaatac                                                             67

<210> SEQ ID NO 36
<211> LENGTH: 58
<212> TYPE: DNA
<213> ORGANISM: Artificial sequence
<220> FEATURE:
<223> OTHER INFORMATION: Primer

<400> SEQUENCE: 36
cctccactcc cgcctccacc tgaagagacg gtgacggtgg tcccttggcc ccagaaat     58

<210> SEQ ID NO 37
<211> LENGTH: 61
<212> TYPE: DNA
<213> ORGANISM: Artificial sequence
<220> FEATURE:
<223> OTHER INFORMATION: Primer

<400> SEQUENCE: 37
tggaggcggg agtggaggtg gcggatctgg aggggtggt agcgacatac agatgacgca    60
g                                                                   61

<210> SEQ ID NO 38
<211> LENGTH: 51
```

-continued

<212> TYPE: DNA
<213> ORGANISM: Artificial sequence
<220> FEATURE:
<223> OTHER INFORMATION: Primer

<400> SEQUENCE: 38
tgctgatacc aatttaaaga actgctaatg tcstgagttg cccggcaagt g    51

<210> SEQ ID NO 39
<211> LENGTH: 38
<212> TYPE: DNA
<213> ORGANISM: Artificial sequence
<220> FEATURE:
<223> OTHER INFORMATION: Primer

<400> SEQUENCE: 39
tctttaaatt ggtatcagca aaaccgggg aaagcccc    38

<210> SEQ ID NO 40
<211> LENGTH: 60
<212> TYPE: DNA
<213> ORGANISM: Artificial sequence
<220> FEATURE:
<223> OTHER INFORMATION: Primer

<400> SEQUENCE: 40
caccttggtc cctccgccga aagtgaggkg taaactatgg trctgttgac agtaataagt    60

<210> SEQ ID NO 41
<211> LENGTH: 50
<212> TYPE: DNA
<213> ORGANISM: Artificial sequence
<220> FEATURE:
<223> OTHER INFORMATION: Primer

<400> SEQUENCE: 41
tagtcgacca ggcccccgag gcctttgatt tccaccttgg tccctccgcc    50

<210> SEQ ID NO 42
<211> LENGTH: 48
<212> TYPE: DNA
<213> ORGANISM: Artificial sequence
<220> FEATURE:
<223> OTHER INFORMATION: Primer

<400> SEQUENCE: 42
agtagcaact gcaaccggtg tacattctca ggtgcagctg caggagtc    48

<210> SEQ ID NO 43
<211> LENGTH: 40
<212> TYPE: DNA
<213> ORGANISM: Artificial sequence
<220> FEATURE:
<223> OTHER INFORMATION: Primer

<400> SEQUENCE: 43
gatgggccct tggtcgacgc tgaagagacg gtgacggtgg    40

<210> SEQ ID NO 44
<211> LENGTH: 50
<212> TYPE: DNA
<213> ORGANISM: Artificial sequence
<220> FEATURE:
<223> OTHER INFORMATION: Primer

<400> SEQUENCE: 44

```
agtagcaact gcaaccggtg tacattctga catacagatg acgcagtctc        50
```

<210> SEQ ID NO 45
<211> LENGTH: 39
<212> TYPE: DNA
<213> ORGANISM: Artificial sequence
<220> FEATURE:
<223> OTHER INFORMATION: Primer

<400> SEQUENCE: 45

```
atggtgcagc caccgtacgt ttgatttcca ccttggtcc                    39
```

<210> SEQ ID NO 46
<211> LENGTH: 9
<212> TYPE: PRT
<213> ORGANISM: Artificial sequence
<220> FEATURE:
<223> OTHER INFORMATION: M1D LCDR3

<400> SEQUENCE: 46

Gln Gln Tyr His Ser Leu Pro Leu Thr
1               5

<210> SEQ ID NO 47
<211> LENGTH: 330
<212> TYPE: PRT
<213> ORGANISM: Artificial sequence
<220> FEATURE:
<223> OTHER INFORMATION: Human IgG1 heavy chain constant region with V4
      mutation

<400> SEQUENCE: 47

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Tyr Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

```
Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Tyr His Tyr Thr
305                 310                 315                 320

Gln Lys Ser Leu Ser Leu Ser Pro Gly Lys
                325                 330

<210> SEQ ID NO 48
<211> LENGTH: 330
<212> TYPE: PRT
<213> ORGANISM: Artificial sequence
<220> FEATURE:
<223> OTHER INFORMATION: Human IgG1 heavy chain constant region with DY
      mutation

<400> SEQUENCE: 48

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Asp Ala Tyr Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
```

```
                245                 250                 255
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 49
<211> LENGTH: 19
<212> TYPE: PRT
<213> ORGANISM: Artificial sequence
<220> FEATURE:
<223> OTHER INFORMATION: Signal peptide

<400> SEQUENCE: 49

Met Gly Trp Ser Cys Ile Ile Leu Phe Leu Val Ala Thr Ala Thr Gly
1               5                   10                  15

Val His Ser

<210> SEQ ID NO 50
<211> LENGTH: 9
<212> TYPE: PRT
<213> ORGANISM: Artificial sequence
<220> FEATURE:
<223> OTHER INFORMATION: HCDR1 general formula
<220> FEATURE:
<221> NAME/KEY: MISC_FEATURE
<222> LOCATION: (5)..(5)
<223> OTHER INFORMATION: X = T or H
<220> FEATURE:
<221> NAME/KEY: MISC_FEATURE
<222> LOCATION: (6)..(6)
<223> OTHER INFORMATION: X = S or H

<400> SEQUENCE: 50

Gly Gly Ser Ile Xaa Xaa Asn Phe Trp
1               5

<210> SEQ ID NO 51
<211> LENGTH: 7
<212> TYPE: PRT
<213> ORGANISM: Artificial sequence
<220> FEATURE:
<223> OTHER INFORMATION: HCDR2 general formula
<220> FEATURE:
<221> NAME/KEY: MISC_FEATURE
<222> LOCATION: (1)..(1)
<223> OTHER INFORMATION: X = S or H
<220> FEATURE:
<221> NAME/KEY: MISC_FEATURE
<222> LOCATION: (3)..(3)
<223> OTHER INFORMATION: X = P, S or Y
<220> FEATURE:
<221> NAME/KEY: MISC_FEATURE
<222> LOCATION: (4)..(4)
<223> OTHER INFORMATION: X = G or D
<220> FEATURE:
<221> NAME/KEY: MISC_FEATURE
<222> LOCATION: (5)..(5)
<223> OTHER INFORMATION: X = T or H
<220> FEATURE:
<221> NAME/KEY: MISC_FEATURE
<222> LOCATION: (6)..(6)
```

```
<223> OTHER INFORMATION: X = Y or H

<400> SEQUENCE: 51

Xaa Gly Xaa Xaa Xaa Xaa Thr
1               5

<210> SEQ ID NO 52
<211> LENGTH: 15
<212> TYPE: PRT
<213> ORGANISM: Artificial sequence
<220> FEATURE:
<223> OTHER INFORMATION: HCDR3 general formula
<220> FEATURE:
<221> NAME/KEY: MISC_FEATURE
<222> LOCATION: (5)..(5)
<223> OTHER INFORMATION: X = D or H
<220> FEATURE:
<221> NAME/KEY: MISC_FEATURE
<222> LOCATION: (8)..(8)
<223> OTHER INFORMATION: X = S or H
<220> FEATURE:
<221> NAME/KEY: MISC_FEATURE
<222> LOCATION: (9)..(9)
<223> OTHER INFORMATION: X = H or N

<400> SEQUENCE: 52

Ala Arg Ser His Xaa Tyr Gly Xaa Xaa Asp Tyr Ala Phe Asp Phe
1               5                   10                  15

<210> SEQ ID NO 53
<211> LENGTH: 6
<212> TYPE: PRT
<213> ORGANISM: Artificial sequence
<220> FEATURE:
<223> OTHER INFORMATION: LCDR1 general formula
<220> FEATURE:
<221> NAME/KEY: MISC_FEATURE
<222> LOCATION: (4)..(4)
<223> OTHER INFORMATION: X = S or H
<220> FEATURE:
<221> NAME/KEY: MISC_FEATURE
<222> LOCATION: (5)..(5)
<223> OTHER INFORMATION: X = S, Y or H

<400> SEQUENCE: 53

Gln Asp Ile Xaa Xaa Ser
1               5

<210> SEQ ID NO 54
<211> LENGTH: 9
<212> TYPE: PRT
<213> ORGANISM: Artificial sequence
<220> FEATURE:
<223> OTHER INFORMATION: LCDR3 general formula
<220> FEATURE:
<221> NAME/KEY: MISC_FEATURE
<222> LOCATION: (5)..(5)
<223> OTHER INFORMATION: X = S or Y

<400> SEQUENCE: 54

Gln Gln Tyr His Xaa Leu Pro Leu Thr
1               5

<210> SEQ ID NO 55
<211> LENGTH: 97
<212> TYPE: PRT
<213> ORGANISM: Artificial sequence
<220> FEATURE:
<223> OTHER INFORMATION: IGHV4-4*08

<400> SEQUENCE: 55
```

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Thr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg

<210> SEQ ID NO 56
<211> LENGTH: 95
<212> TYPE: PRT
<213> ORGANISM: Artificial sequence
<220> FEATURE:
<223> OTHER INFORMATION: IGKV1-39*01

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95

<210> SEQ ID NO 57
<211> LENGTH: 330
<212> TYPE: PRT
<213> ORGANISM: Artificial sequence
<220> FEATURE:
<223> OTHER INFORMATION: Human IgG1 heavy chain constant region

<400> SEQUENCE: 57

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110
```

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 58
<211> LENGTH: 107
<212> TYPE: PRT
<213> ORGANISM: Artificial sequence
<220> FEATURE:
<223> OTHER INFORMATION: Human kappa light chain constant region

<400> SEQUENCE: 58

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Ser Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

ANTI-HEPATITIS B VIRUS ANTIBODY AND USES THEREOF

TECHNICAL FIELD

The present invention relates to the field of molecular virology and immunology, especially the field of treatment of hepatitis B virus (HBV) infection. Specifically, the present invention relates to an antibody against hepatitis B virus surface antigen (HBsAg) and a nucleic acid encoding the antibody, and a use thereof. The anti-HBsAg antibody of the present invention has a higher binding affinity for HBsAg at neutral pH than at acidic pH. The novel antibody can be used for the prevention and/or treatment of an HBV infection or a disease associated with HBV infection (for example, hepatitis B), for neutralizing a virulence of HBV in a subject (for example, a human), or for reducing a serum level of HBV DNA and/or HBsAg in a subject. Therefore, the present invention further relates to a use of the antibody and variant thereof in the manufacture of a pharmaceutical composition for the prevention and/or treatment of an HBV infection or a disease related to an HBV infection (for example, hepatitis B), for neutralizing a virulence of HBV in a subject (for example, a human), for reducing a serum level of HBV DNA and/or HBsAg in a subject, or for activating a humoral immune response to HBV in a subject (for example, a person with chronic HBV infection or a patient with chronic hepatitis B).

BACKGROUND ART

Hepatitis B virus infection, especially chronic HBV infection, is one of the most important public health problems in the world (Dienstag J L. Hepatitis B virus infection. N Engl J Med Oct. 2, 2008; 359(14):1486-1500). Chronic HBV infection can lead to a series of liver diseases such as chronic hepatitis B (CHB), liver cirrhosis (LC) and primary hepatocellular carcinoma (HCC) (Liaw Y F, Chu C M. Hepatitis B virus infection. Lancet Feb. 14, 2009; 373(9663): 582-592). According to reports, there are currently about 2 billion people in the world who have been infected with HBV, there are now about 350 million persons with chronic hepatitis B virus infections, the risk of these infected persons eventually dying from HBV infection-associated liver diseases can reach 15% to 25%, and more than one million people die from such diseases each year worldwide (Dienstag J L., ibid; and Liaw Y F, et al., ibid).

The current treatment drugs for chronic HBV infection can be divided into interferons (IFNs) and nucleoside or nucleotide analogs (NAs) (Dienstag J L., ibid.; Kwon H, Lok A S. Hepatitis B therapy. Nat Rev Gastroenterol Hepatol 2011 May; 8(5): 275-284; and Liaw Y F et al., ibid.). However, the treatment with the above-mentioned drugs alone or in combination cannot completely eliminate the HBV virus in the infected persons, and the response rate of HBsAg negative conversion or HBsAg seroconversion (a sign of complete HBV virus clearance in the infected person) caused thereby is usually less than 5% (Kwon H et al., ibid.).

The development of new drugs for the treatment of chronic HBV infection based on immunological means is one of the important research directions in this field. Immunotherapy for chronic HBV infection is usually carried out in two ways: active immunotherapy (its corresponding drug forms including vaccines, etc.) and passive immunotherapy (its corresponding drug forms including antibodies, etc.). Active immunotherapy refers to administration of a therapeutic vaccine (including protein vaccine, peptide vaccine, nucleic acid vaccine, etc.) in order to stimulate the body of chronic HBV infected person to actively produce a cellular immune response (CTL effect, etc.) or/and humoral immune response against HBV (antibodies, etc.), so as to achieve the purpose of inhibiting or eliminating HBV. Currently, there is no definitely significant and effective active immunotherapy drug/vaccine that can be used to treat chronic HBV infection. Passive immunotherapy (taking antibody as an example) refers to administration of an antibody with therapeutic properties to a HBV infected person, and a therapeutic effect can be achieved by the antibody-mediated virus neutralization to block HBV from infecting newborn hepatocytes, or by the antibody-mediated immune clearance to remove viruses and infected liver cells from the body. At present, the anti-HBs polyclonal antibody purified from the serum/plasma of those who had a response to a prophylactic hepatitis B vaccine or those who have recovered from HBV infection, namely high-potency hepatitis B immunoglobulin (HBIG), has been widely used to block mother-to-child vertical transmission of HBV, prevent HBV reinfection after liver transplantation in patients with chronic HBV infection, and prevent people accidentally exposed to HBV from being infected. However, the direct application of HBIG in the treatment of HBV-infected patients (for example, CHB patients) has no obvious effect, and it has many limitations such as fewer sources for high-potency plasma, high price, unstable nature, and potential safety issues.

Therefore, it is urgent and necessary to develop innovative treatment methods and drugs for HBV infected persons that can more effectively remove HBV virus, especially HBsAg.

Contents of the Present Invention

The present inventors have previously developed an anti-HBsAg humanized antibody with excellent properties, which can neutralize the virulence of HBV in vivo and reduce the serum levels of HBV DNA and/or HBsAg. On the basis of the previous research, the present inventors have paid a lot of creative work to conduct in-depth research and engineering of the humanized antibody, thereby developing an anti-HBsAg antibody with pH-dependent antigen binding ability. The anti-HBsAg antibody of the present invention has a higher binding affinity for HBsAg at neutral pH than at acidic pH, so that the reuse of antibody is realized, the antibody half-life is significantly extended, and the efficiency of HBV clearance is enhanced. Furthermore, the present inventors obtain a scavenger antibody and further extend the antibody half-life by introducing a mutation into the Fc region of the above-mentioned antibody to enhance its affinity to hFcRn or mFcγRII under neutral condition.

The antibody of the present invention is extremely advantageous, since it not only retains the activity of reducing the serum level of HBV DNA and/or HBsAg, but also has a longer time of antigen suppression, thereby greatly reducing the injection dosage and administration frequency of treatment, and having significant clinical value.

Antibody of the Present Invention

Therefore, in one aspect, the present invention provides an antibody or antigen-binding fragment thereof capable of specifically binding to HBsAg, in which the antibody or antigen-binding fragment thereof binds to HBsAg with higher affinity at neutral pH than at acidic pH.

In certain embodiments, the neutral pH is pH 6.7 to pH 7.5, such as pH 7.4.

In certain embodiments, the acidic pH is pH 4.0 to pH 6.5, such as pH 6.0.

In certain embodiments, a ratio of $K_D$ of binding to HBsAg at an acidic pH (for example, pH 6.0) to $K_D$ of binding to HBsAg at neutral pH (for example, pH 7.4) (i.e., value of $K_D$ (acidic pH)/$K_D$ (neutral pH)), of the antibody or antigen-binding fragment thereof, is greater than 1, for example not less than 1.5, not less than 2, not less than 3, not less than 4, not less than 5, not less than 6, not less than 7, not less than 8, not less than 9, not less than 10, not less than 15, not less than 20, not less than 30, not less than 40, not less than 50, not less than 60, not less than 70, not less than 80, not less than 90, not less than 100, not less than 300, not less than 500, not less than 800, not less than 1000, not less than 2000, not less than 5000, or not less than 10,000. In some embodiments, the value of $K_D$ (acidic pH)/$K_D$ (neutral pH) is greater than 1 and not greater than 10000, for example, not greater than 5000, not greater than 2000, not greater than 1000, not greater than 900, not greater than 800, not greater than 700, not greater than 600, not greater than 500, not greater than 400, not greater than 300, not greater than 200, not greater than 100, not greater than 90, not greater than 80, not greater than 70, not greater than 60, not greater than 50, not greater than 40, not greater than 30, not greater than 20, or not greater than 10. The $K_D$ can be measured by a technique known in the art, for example, by SPR technique (for example, Biacore).

In some embodiments, a ratio of $K_D$ of binding to HBsAg at pH 6.0 to $K_D$ of binding to HBsAg at pH 7.4 of the antibody or antigen-binding fragment thereof, is greater than 1, for example not less than 1.5, not less than 2. In certain embodiments, the $K_D$ value of the antibody or antigen-binding fragment thereof at neutral pH may be $10^{-7}$ M, $10^{-8}$ M, $10^{-9}$ M, $10^{-10}$ M, $10^{-11}$ M, $10^{-12}$ M or less. In some embodiments, the $K_D$ value of the antibody of the present invention at acidic pH may be $10^{-9}$ M, $10^{-8}$ M, $10^{-7}$ M, $10^{-6}$ M or more.

In certain embodiments, a ratio of EC50 of binding to HBsAg at an acidic pH (for example, pH 6.0) to EC50 of binding to HBsAg at neutral pH (for example, pH 7.4) (i.e., value of EC50 (acidic pH)/EC50 (neutral pH)), of the antibody or antigen-binding fragment thereof, is greater than 1, for example not less than 1.5, not less than 2, not less than 3, not less than 4, not less than 5, not less than 6, not less than 7, not less than 8, not less than 9, not less than 10, not less than 15, not less than 20, not less than 30, not less than 40, not less than 50, not less than 60, not less than 70, not less than 80, not less than 90, not less than 100, not less than 300, not less than 500, not less than 800, not less than 1000, not less than 2000, not less than 5000, or not less than 10,000. In some embodiments, the value of EC50 (acidic pH)/EC50 (neutral pH) is greater than 1 and not greater than 10000, for example, not greater than 5000, not greater than 2000, not greater than 1000, not greater than 900, and not greater than 800, not greater than 700, not greater than 600, not greater than 500, not greater than 400, not greater than 300, not greater than 200, not greater than 100, not greater than 90, not greater than 80, not greater than 70, not greater than 60, not greater than 50, not greater than 40, not greater than 30, not greater than 20, or not greater than 10. In some embodiments, the EC50 is measured by ELISA method, for example, calculated by the regression analysis of a dose-response curve generated by the ELISA method.

In certain embodiments, a ratio of EC50 of binding to HBsAg at pH 6.0 to EC50 of binding to HBsAg at pH 7.4 of the antibody or antigen-binding fragment thereof, is greater than 1, for example, not less than 1.5, or not less than 2.

In certain embodiments, the antibody or antigen-binding fragment thereof of the present invention is derived from the anti-HBV humanized antibody M1D (which is described in detail in Chinese Patent Application 201810307136.5).

In certain embodiments, the antibody or antigen-binding fragment thereof of the present invention binds to aa118-124 of HBsAg with higher affinity at neutral pH than at acidic pH.

In certain embodiments, the antibody or antigen-binding fragment thereof comprises a heavy chain variable region (VH) comprising HCDR1, HCDR2 and HCDR3, which has one or more of the following characteristics:

(i) HCDR1 has at least one amino acid (for example, 1, 2, 3, 4 or 5 amino acids) replaced with histidine as compared with a sequence shown in SEQ ID NO: 20;

(ii) HCDR2 has at least one amino acid (for example, 1, 2, 3, 4 or 5 amino acids) replaced with histidine as compared with a sequence shown in SEQ ID NO: 21; and/or, (iii) HCDR2 has at least one amino acid (for example, 1, 2, 3, 4 or 5 amino acids) replaced with histidine as compared with a sequence shown in SEQ ID NO: 16.

In certain embodiments, the antibody or antigen-binding fragment thereof comprises a heavy chain variable region (VL) comprising LCDR1, LCDR2 and LCDR3, which has one or more of the following characteristics:

(i) LCDR1 has at least one amino acid (for example, 1, 2, 3, 4 or 5 amino acids) replaced with histidine as compared with a sequence shown in SEQ ID NO: 11;

(ii) LCDR2 has at least one amino acid (for example, 1, 2, 3, 4 or 5 amino acids) replaced with histidine as compared with a sequence shown in SEQ ID NO: 12; and/or, (iii) LCDR2 has at least one amino acid (for example, 1, 2, 3, 4 or 5 amino acids) replaced with histidine as compared with a sequence shown in SEQ ID NO: 46.

In certain embodiments, the antibody or antigen-binding fragment thereof comprises:

(a) a heavy chain variable region (VH) comprising the following 3 CDRs:

(i) HCDR1 with a sequence of $GGSIX_1X_2NFW$ (SEQ ID NO: 50), wherein $X_1$ is selected from T or H, and $X_2$ is selected from S or H;

(ii) HCDR2 with a sequence of $X_3GX_4X_5X_6X_7T$ (SEQ ID NO: 51), wherein $X_3$ is selected from S or H, $X_4$ is selected from P, S or Y, $X_3$ is selected from G or D, $X_6$ is selected from T or H, and $X_7$ is selected from Y or H; and (iii) HCDR3 with a sequence of $ARSHX_8YGX_9X_{10}DYAFDF$ (SEQ ID NO: 52), wherein $X_8$ is selected from D or H, $X_9$ is selected from S or H, and $X_{10}$ is selected from H or N; and/or, (b) a light chain variable region (VL) comprising the following 3 CDRs:

(iv) LCDR1 with a sequence of $QDIX_{11}X_{12}S$ (SEQ ID NO: 53), wherein $X_{11}$ is selected from S or H, and $X_{12}$ is selected from S, Y or H;

(v) LCDR2 with a sequence of YAN (SEQ ID NO: 12); and (vi) LCDR3 with a sequence of $QQYHX_{13}LPLT$ (SEQ ID NO: 54), wherein $X_{13}$ is selected from S or Y.

In certain embodiments, the antibody or antigen-binding fragment thereof comprises:

(a) a heavy chain variable region (VH) comprising the following 3 CDRs:

(i) HCDR1, which is composed of a sequence selected from the following: SEQ ID NOs: 8, 14, 17, 20;

(ii) HCDR2, which is composed of a sequence selected from: SEQ ID NOs: 9, 15, 21, 18; and (iii) HCDR3, which is composed of a sequence selected from the following: SEQ ID NOs: 10, 16, 22;
and/or,
(b) a light chain variable region (VL) comprising the following 3 CDRs:
(iv) LCDR1, which is composed of a sequence selected from the following: SEQ ID NOs: 11, 19, 23;
(v) LCDR2, which is composed of a sequence shown in SEQ ID NO: 12; and
(vi) LCDR3, which is composed of a sequence shown in SEQ ID NO: 13.

In certain embodiments, $X_1$ is selected from T or H, $X_2$ is selected from S, $X_3$ is selected from S, $X_4$ is selected from P or S, $X_5$ is selected from G, $X_6$ is selected from T or H, $X_7$ is selected from Y or H, $X_8$ is selected from D or H, $X_9$ is selected from S or H, $X_{10}$ is selected from H or N, $X_{11}$ is selected from S, $X_{12}$ is selected from S or Y, and $X_{13}$ is selected from Y.

In certain embodiments, the antibody or antigen-binding fragment thereof comprises:
(a) a heavy chain variable region (VH) comprising the following 3 CDRs:
(i) HCDR1, which is composed of a sequence selected from the following: SEQ ID NOs: 8, 20;
(ii) HCDR2, which is composed of a sequence selected from: SEQ ID NOs: 9, 21; and
(iii) HCDR3, which is composed of a sequence selected from the following: SEQ ID NOs: 10, 22;
and/or,
(b) a light chain variable region (VL) comprising the following 3 CDRs:
(iv) LCDR1, which is composed of a sequence selected from the following: SEQ ID NOs: 11, 23;
(v) LCDR2, which is composed of a sequence shown in SEQ ID NO: 12; and
(vi) LCDR3, which is composed of a sequence shown in SEQ ID NO: 13.

In certain embodiments, the antibody or antigen-binding fragment thereof comprises:
(1) a VH comprising the following 3 CDRs: HCDR1 shown in SEQ ID NO: 8, HCDR2 shown in SEQ ID NO: 9, HCDR3 shown in SEQ ID NO: 10; and, a VL comprising the following 3 CDRs: LCDR1 shown in SEQ ID NO: 11, LCDR2 shown in SEQ ID NO: 12, LCDR3 shown in SEQ ID NO: 13;
(2) a VH comprising the following 3 CDRs: HCDR1 shown in SEQ ID NO: 14, HCDR2 shown in SEQ ID NO: 15, HCDR3 shown in SEQ ID NO: 16; and, a VL comprising the following 3 CDRs: LCDR1 shown in SEQ ID NO: 11, LCDR2 shown in SEQ ID NO: 12, LCDR3 shown in SEQ ID NO: 13;
(3) a VH comprising the following 3 CDRs: HCDR1 shown in SEQ ID NO: 20, HCDR2 shown in SEQ ID NO: 21, HCDR3 shown in SEQ ID NO: 22; and, a VL comprising the following 3 CDRs: LCDR1 shown in SEQ ID NO: 23, LCDR2 shown in SEQ ID NO: 12, LCDR3 shown in SEQ ID NO: 13; or,
(4) a VH comprising the following 3 CDRs: HCDR1 shown in SEQ ID NO: 17, HCDR2 shown in SEQ ID NO: 18, HCDR3 shown in SEQ ID NO: 10; and, a VL comprising the following 3 CDRs: LCDR1 shown in SEQ ID NO: 19, LCDR2 shown in SEQ ID NO: 12, LCDR3 shown in SEQ ID NO: 13.

In certain embodiments, the antibody or antigen-binding fragment thereof further comprises a framework region of a human immunoglobulin (for example, a framework region contained in an amino acid sequence encoded by a human germline antibody gene), and the framework region optionally comprises one or more (for example, 1, 2, 3, 4, 5, 6, 7, 8, 9 or 10) back mutations from human residues to murine residues.

In certain embodiments, the antibody or antigen-binding fragment thereof comprises: a heavy chain framework region contained in an amino acid sequence encoded by a human heavy chain germline gene, and/or a light chain framework region contained in an amino acid sequence encoded by a human light chain germline gene.

In certain embodiments, the antibody or antigen-binding fragment thereof comprises: a heavy chain framework region contained in an amino acid sequence encoded by IGHV4-4*08 (SEQ ID NO: 55), and a light chain framework region contained in an amino acid sequence encoded by IGKV1-39*01 (SEQ ID NO: 56), and the heavy chain framework region and/or the light chain framework region optionally comprises one or more (for example, 1, 2, 3, 4, 5, 6, 7, 8, 9 or 10) back mutations from human residues to murine residues.

In certain embodiments, the VH of the antibody or antigen-binding fragment thereof comprises: VH FR1 as shown in SEQ ID NO: 24, VH FR2 as shown in SEQ ID NO: 25, VH FR3 as shown in SEQ ID NO: 26, and VH FR4 shown in SEQ ID NO: 27.

In some embodiments, the VL of the antibody or antigen-binding fragment thereof comprises: VL FR1 as shown in SEQ ID NO: 28, VL FR2 as shown in SEQ ID NO: 29, VL FR3 as shown in SEQ ID NO: 30, and VL FR4 shown in SEQ ID NO: 31.

In certain embodiments, the antibody or antigen-binding fragment thereof comprises:
(a) a heavy chain variable region (VH), which comprises an amino acid sequence selected from the following:
(i) a sequence shown in any one of SEQ ID NOs: 1, 3, 4 and 6;
(ii) a sequence with substitution, deletion or addition of one or several amino acids (for example, substitution, deletion or addition of 1, 2, 3, 4 or 5 amino acids) as compared with a sequence shown in any one of SEQ ID NOs: 1, 3, 4, 6; or
(iii) a sequence with a sequence identity of at least 80%, at least 85%, at least 90%, at least 91%, at least 92%, at least 93%, at least 94%, at least 95%, at least 96%, at least 97%, at least 98%, at least 99%, or 100% as compared with a sequence shown in any one of SEQ ID NOs: 1, 3, 4, 6; and
(b) a light chain variable region (VL), which comprises an amino acid sequence selected from the following:
(iv) a sequence shown in any one of SEQ ID NOs: 2, 5, and 7;
(v) a sequence with substitution, deletion or addition of one or several amino acids (for example, substitution, deletion or addition of 1, 2, 3, 4 or 5 amino acids) as compared with a sequence shown in any one of SEQ ID NOs: 2, 5, 7; or
(vi) a sequence with a sequence identity of at least 80%, at least 85%, at least 90%, at least 91%, at least 92%, at least 93%, at least 94%, at least 95%, at least 96%, at least 97%, at least 98%, at least 99%, or 100% as compared with a sequence shown in any one of SEQ ID NOs: 2, 5, 7.

In certain embodiments, the substitution described in (ii) or (v) is a conservative substitution.

In certain embodiments, the antibody or antigen-binding fragment thereof comprises:
(1) a VH with a sequence shown in SEQ ID NO: 1 and a VL with a sequence shown in SEQ ID NO: 2;

(2) a VH with a sequence shown in SEQ ID NO: 3 and a VL with a sequence shown in SEQ ID NO: 2;

(3) a VH with a sequence shown in SEQ ID NO: 4 and a VL with a sequence shown in SEQ ID NO: 5; or (4) a VH with a sequence shown in SEQ ID NO: 6 and a VL with a sequence shown in SEQ ID NO: 7.

In certain embodiments, the antibody or antigen-binding fragment thereof further comprises a constant region derived from a human immunoglobulin.

In certain embodiments, the heavy chain of the antibody or antigen-binding fragment thereof comprises a heavy chain constant region derived from a human immunoglobulin (for example, IgG1, IgG2, IgG3, or IgG4), and the light chain of the antibody or antigen-binding fragment thereof comprises a light chain constant region derived from a human immunoglobulin (for example, κ or λ).

In certain embodiments, the antibody or antigen-binding fragment thereof comprises:

(a) a heavy chain constant region (CH) of a human immunoglobulin or a variant thereof, wherein the variant has substitution, deletion or addition of one or more amino acids or any combination thereof (for example, substitution, deletion or addition of at most 20, at most 15, at most 10, or at most 5 amino acids or any combination thereof; for example, substitution, deletion or addition of 1, 2, 3, 4 or 5 amino acids or any combination thereof) as compared with a wild-type sequence from which it is derived; and/or (b) a light chain constant region (CL) of a human immunoglobulin or a variant thereof, wherein the variant has substitution, deletion or addition of one or more amino acids or any combination thereof (for example, substitution, deletion or addition of at most 20, at most 15, at most 10, or at most 5 amino acids or any combination thereof; for example, substitution, deletion or addition of 1, 2, 3, 4 or 5 amino acids or any combination thereof) as compared with a wild-type sequence from which it is derived.

In certain embodiments, the antibody or antigen-binding fragment thereof comprises a human IgG1 or IgG4 heavy chain constant region. In certain embodiments, the antibody or antigen-binding fragment thereof comprises a heavy chain constant region (CH) as shown in SEQ ID NO: 57.

In certain embodiments, the antibody or antigen-binding fragment thereof of the present invention comprises a variant of a heavy chain constant region (CH) of a human immunoglobulin, in which the variant has an enhanced affinity to hFcRn or mFcγRII at neutral pH (for example, pH 7.4) as compared with a wild-type sequence from which it is derived. In such embodiments, the variant generally has substitution of at least one amino acid as compared with a wild-type sequence from which it is derived.

In certain embodiments, the antibody or antigen-binding fragment thereof comprises a variant of a human IgG1 heavy chain constant region, in which the variant has the following substitutions as compared to a wild-type sequence from which it is derived: (i) M252Y, N286E, N434Y; or, (ii) K326D, L328Y; wherein the above-mentioned amino acid positions are positions according to the Kabat numbering system. In certain embodiments, the antibody or antigen-binding fragment thereof comprises a heavy chain constant region (CH) as shown in SEQ ID NO: 47 or 48.

In certain embodiments, the light chain constant region is a κ light chain constant region. In certain embodiments, the antibody or antigen-binding fragment thereof comprises a light chain constant region (CL) as shown in SEQ ID NO: 58.

In certain embodiments, the antibody or antigen-binding fragment thereof comprises:

(1) a heavy chain comprising a VH shown in SEQ ID NO: 1 and a CH shown in SEQ ID NO: 57, and a light chain comprising a VL shown in SEQ ID NO: 2 and a CL shown in SEQ ID NO: 58;

(2) a heavy chain comprising a VH shown in SEQ ID NO: 1 and a CH shown in SEQ ID NO: 47, and a light chain comprising a VL shown in SEQ ID NO: 2 and a CL shown in SEQ ID NO: 58;

(3) a heavy chain comprising a VH shown in SEQ ID NO: 1 and a CH shown in SEQ ID NO: 48, and a light chain comprising a VL shown in SEQ ID NO: 2 and a CL shown in SEQ ID NO: 58;

(4) a heavy chain comprising a VH shown in SEQ ID NO: 3 and a CH shown in SEQ ID NO: 57, and a light chain comprising a VL shown in SEQ ID NO: 2 and a CL shown in SEQ ID NO: 58;

(5) a heavy chain comprising a VH shown in SEQ ID NO: 3 and a CH shown in SEQ ID NO: 47, and a light chain comprising a VL shown in SEQ ID NO: 2 and a CL shown in SEQ ID NO: 58;

(6) a heavy chain comprising a VH shown in SEQ ID NO: 3 and a CH shown in SEQ ID NO: 48, and a light chain comprising a VL shown in SEQ ID NO: 2 and a CL shown in SEQ ID NO: 58;

(7) a heavy chain comprising a VH shown in SEQ ID NO: 4 and a CH shown in SEQ ID NO: 57, and a light chain comprising a VL shown in SEQ ID NO: 5 and a CL shown in SEQ ID NO: 58;

(8) a heavy chain comprising a VH shown in SEQ ID NO: 4 and a CH shown in SEQ ID NO: 47, and a light chain comprising a VL shown in SEQ ID NO: 5 and a CL shown in SEQ ID NO: 58;

(9) a heavy chain comprising a VH shown in SEQ ID NO: 4 and a CH shown in SEQ ID NO: 48, and a light chain comprising a VL shown in SEQ ID NO: 5 and a CL shown in SEQ ID NO: 58;

(10) a heavy chain comprising a VH shown in SEQ ID NO: 6 and a CH shown in SEQ ID NO: 57, and a light chain comprising a VL shown in SEQ ID NO: 7 and a CL shown in SEQ ID NO: 58;

(11) a heavy chain comprising a VH shown in SEQ ID NO: 6 and a CH shown in SEQ ID NO: 47, and a light chain comprising a VL shown in SEQ ID NO: 7 and a CL shown in SEQ ID NO: 58; or

(12) a heavy chain comprising a VH shown in SEQ ID NO: 6 and a CH shown in SEQ ID NO: 48, and a light chain comprising a VL shown in SEQ ID NO: 7 and a CL shown in SEQ ID NO: 58.

Preparation of Antibody

The antibody of the present invention can be prepared by various methods known in the art, for example, obtained by genetic engineering recombination technology. For example, DNA molecules encoding the heavy chain and light chain genes of the antibody of the present invention are obtained by chemical synthesis or PCR amplification. The resulting DNA molecule is inserted into an expression vector and then transfected into a host cell. Then, the transfected host cell is cultured under specific conditions, and the antibody of the present invention is expressed.

The antigen-binding fragment of the present invention can be obtained by hydrolyzing a complete antibody molecule (see Morimoto et al., J. Biochem. Biophys. Methods 24:107-117 (1992) and Brennan et al., Science 229:81 (1985)). In addition, these antigen-binding fragments can also be directly produced by recombinant host cells (reviewed in Hudson, Curr. Opin. Immunol. 11: 548-557 (1999); Little et al., Immunol. Today, 21: 364-370 (2000))). For example, Fab' fragments can be obtained directly from host cells; Fab' fragments can be chemically coupled to form F(ab')$_2$ fragments (Carter et al., Bio/Technology, 10: 163-167 (1992)). In addition, Fv, Fab or F(ab')$_2$ fragments can also be directly isolated from a recombinant host cell culture medium. Those of ordinary skill in the art are fully aware of other techniques for preparing these antigen-binding fragments.

Therefore, in another aspect, the present invention provides an isolated nucleic acid molecule comprising a nucleotide sequence encoding the antibody or antigen-binding fragment thereof of the present invention, or heavy chain variable region and/or light chain variable region thereof. In certain preferred embodiments, the isolated nucleic acid molecule encodes the antibody or antigen-binding fragment thereof of the present invention, or heavy chain variable region and/or light chain variable region thereof.

In another aspect, the present invention provides a vector (for example, a cloning vector or an expression vector) comprising the isolated nucleic acid molecule of the present invention. In certain preferred embodiments, the vector of the present invention is, for example, plasmid, cosmid, bacteriophage and the like.

In another aspect, the present invention provides a host cell comprising the isolated nucleic acid molecule of the present invention or the vector of the present invention. Such host cell includes, but is not limited to, prokaryotic cell such as *E. coli* cell, and eukaryotic cell such as yeast cell, insect cell, plant cell and animal cell (for example, mammalian cell, such as mouse cell, human cell, etc.). In certain preferred embodiments, the host cell of the present invention is a mammalian cell, such as CHO (for example, CHO—K1, CHO—S, CHO DG44).

In another aspect, a method for preparing the antibody or antigen-binding fragment thereof of the present invention is provided, which comprises culturing the host cell of the present invention under conditions that allow expression of the antibody or antigen-binding fragment thereof, and recovering the antibody or antigen-binding fragment thereof from the cultured host cell culture.

Derived Antibody

The antibody or antigen-binding fragment thereof of the present invention can be derivatized, for example linked to another molecule (for example, another polypeptide or protein). Generally, the derivatization (for example, labeling) of the antibody or antigen-binding fragment thereof will not adversely affect its binding to HBsAg. Therefore, the antibody or antigen-binding fragment thereof of the present invention is also intended to include such derivatized forms. For example, the antibody or antigen-binding fragment of the present invention can be functionally linked (by chemical coupling, gene fusion, non-covalent linkage or other means) to one or more other molecular groups, such as another antibody (for example, to form a bispecific antibody), detection reagent, pharmaceutical reagent, and/or protein or polypeptide capable of mediating the antibody or antigen-binding fragment to bind to another molecule (for example, avidin or polyhistidine tag).

Therefore, in certain embodiments, the antibody of the present invention or antigen-binding fragment thereof is labeled. In some embodiments, the antibody or antigen-binding fragment thereof of the present invention bears a detectable label, such as enzyme, radionuclide, fluorescent dye, luminescent substance (for example, chemiluminescent substance), or biotin. The detectable label of the present invention can be any substance that can be detected by fluorescence, spectroscopy, photochemistry, biochemistry, immunology, electrical, optical or chemical means. Such labels are well known in the art, examples of which include, but are not limited to, enzyme (for example, horseradish peroxidase, alkaline phosphatase, β-galactosidase, urease, glucose oxidase, etc.), radioactive nuclide (for example, $^3$H, $^{125}$I, $^{35}$S, $^{14}$C or $^{32}$P), fluorescent dye (for example, fluorescein isothiocyanate (FITC), fluorescein, tetramethylrhodamine isothiocyanate (TRITC), phycoerythrin (PE), Texas red, rhodamine, quantum dots or cyanine dye derivatives (for example, Cy7, Alexa 750)), luminescent substance (for example, chemiluminescent substance, such as acridine ester compound), magnetic beads (for example, Dynabeads®), calorimetric marker such as colloidal gold or colored glass or plastic (e.g. polystyrene, polypropylene, latex, etc.) beads, and biotin used to ligate avidin (for example, streptavidin) modified by the above-mentioned marker. In certain embodiments, such label can be suitable for immunological detection (for example, enzyme-linked immunoassay, radioimmunoassay, fluorescent immunoassay, chemiluminescence immunoassay, etc.). In certain embodiments, the detectable label as described above can be ligated to the antibody or antigen-binding fragment thereof of the present invention through a linker of different length to reduce potential steric hindrance.

Pharmaceutical Composition and Therapeutic Use

The antibody or antigen-binding fragment thereof of the present invention can be used for the prevention or treatment of an HBV infection in a subject (for example, a human) or a disease associated with HBV infection (for example, hepatitis B), for neutralizing in vitro or in a subject (for example, a human) a virulence of HBV, for reducing a serum level of HBV DNA and/or HBsAg in a subject (for example, a human), and for activating a humoral immune response to HBV in a subject (for example, a patient with chronic HBV infection or chronic hepatitis B).

Therefore, in another aspect, the present invention provides a pharmaceutical composition, which comprises the antibody or antigen-binding fragment thereof of the present invention, and a pharmaceutically acceptable carrier and/or excipient. The pharmaceutical composition of the present invention may also comprises an additional pharmaceutically active agent. In certain embodiments, the additional pharmaceutically active agent is a drug used to prevent or treat an HBV infection or a disease associated with HBV infection (for example, hepatitis B), for example, interferon drug, such as interferon or pegylated interferon.

In another aspect, the present invention provides a use of the antibody or antigen-binding fragment thereof of the present invention or the pharmaceutical composition of the present invention in the manufacture of a medicament for the prevention and/or treatment of an HBV infection (for example, a human) or a disease associated with HBV infection (for example, hepatitis B) in a subject, for neutralizing a virulence of HBV in vitro or in a subject (for example, a human), for reducing a serum level of HBV DNA and/or HBsAg in a subject (for example, a human), and/or for activating a humoral immune response to HBV in a subject (for example, a patient with chronic HBV infection or chronic hepatitis B).

In another aspect, the present invention provides a method for preventing or treating an HBV infection or a disease associated with HBV infection (for example, hepatitis B) in a subject (for example, a human), for neutralizing a virulence of HBV in vivo or in a subject (for example, a human), for reducing a serum level of HBV DNA and/or HBsAg in a subject (for example, a human), and/or for activating a humoral immune response to HBV in a subject (for example, a patient with chronic HBV infection or chronic hepatitis B), the method comprises administering an effective amount of the antibody or antigen-binding fragment thereof according to the present invention or the pharmaceutical composition according to the present invention to a subject in need thereof.

The drugs and pharmaceutical compositions provided by the present invention can be used alone or in combination, and can also be used in combination with other pharmaceutically active agents (for example, other antiviral agents, such as interferon drugs, such as interferon or pegylated interferon).

The antibody or antigen-binding fragment thereof of the present invention or the pharmaceutical composition of the present invention can be administered by a traditional route of administration, including but not limited to oral, buccal, sublingual, ocular, topical, parenteral, rectal, intrathecal, intracytoplasmic reticulum, inguinal, intravesical, topical (e.g., powder, ointment or drops), or nasal route. The antibody or antigen-binding fragment thereof of the present invention can be administered by various methods known in the art. However, for many therapeutic applications, the preferred route/mode of administration is parenteral administration (for example, intravenous injection, subcutaneous injection, intraperitoneal injection, intramuscular injection). The skilled person should understand that the route and/or mode of administration will vary according to the intended purpose. In a preferred embodiment, the antibody or antigen-binding fragment thereof of the present invention is administered by intravenous infusion or injection.

The antibody or antigen-binding fragment thereof of the present invention or the pharmaceutical composition of the present invention can be formulated into a variety of dosage forms, such as liquid, semisolid, and solid forms, for example, solution (e.g. injection), dispersion or suspension, tablet, powder, granule, emulsion, pill, syrup, powder, liposome, capsule and suppository. The preferred dosage form depends on the intended mode of administration and therapeutic use.

For example, one preferred dosage form is an injection. Such an injection may be a sterile injectable solution. For example, a sterile injectable solution can be prepared by the following method: a necessary dose of the antibody or an antigen binding fragment thereof according to the invention is incorporated into a suitable solvent, and optionally, other expected ingredients (including, but not limited to, a pH regulator, a surfactant, an adjuvant, an ionic strength enhancer, an isotonic agent, a preservative, a diluent, or any combination thereof) are incorporated simultaneously, and then filtered sterilization is carried out. In addition, the sterile injectable solution can be prepared into a sterile powder (for example, by vacuum drying or freeze drying) for the convenience of storage and use. Such sterile powder can be dispersed in a suitable vehicle before use, such as sterile pyrogen-free water.

Another preferred dosage form is a dispersion. A dispersion can be prepared by the following method: the antibody or an antigen binding fragment thereof according to the invention is incorporated in a sterile vehicle comprising a basic dispersion medium and optionally, other expected ingredients (including, but not limited to, a pH regulator, a surfactant, an adjuvant, an ionic strength enhancer, an isotonic agent, a preservative, a diluent, or any combination thereof). In addition, an absorption delaying agent can also be incorporated in a dispersion, such as monostearate salt and gelatin, in order to obtain an expected pharmacokinetic property.

Another preferred dosage form is an oral solid dosage form, including capsule, tablet, powder, granule, and the like. Such a solid dosage form generally comprises at least one of: (a) inert drug excipient (or vehicle), such as sodium citrate and calcium phosphate; (b) filler, such as starch, lactose, sucrose, mannose and silicic acid; (c) binder, such as carboxymethyl cellulose, alginate, gelatin, polyvinylpyrrolidone, sucrose and arabic gum; (d) wetting agent, such as glycerol; (e) disintegrating agent, such as agar, calcium carbonate, potato or tapioca starch; (f) retarder, such as olefin; (g) absorption enhancer, such as quaternary ammonium compound; (h) humectant, such as cetyl alcohol and glyceryl monostearate; (i) adsorbent, such as kaolin and bentonite; (j) lubricant, such as talc, calcium stearate, magnesium stearate, solid polyethylene glycol, sodium dodecyl sulfate, or any combination thereof. In the case of tablet and capsule dosage forms, a buffer can also be comprised.

In addition, a release rate modifier (i.e. an agent capable of changing drug release rate) may also be added to an oral solid dosage form, in order to obtain a modified release or pulsed release dosage form. Such a release rate modifier includes, but is not limited to carboxypropyl methylcellulose, methylcellulose, carboxymethyl cellulose sodium, ethyl cellulose, cellulose acetate, polyethylene oxide, xanthan gum, isoacrylic amino copolymer, hydrogenated flavoring oil, carnauba wax, paraffin, cellulose acetate phthalate, carboxypropyl methylcellulose phthalate, methacrylic acid copolymer, or any combination thereof. A modified release or pulsed release dosage form may comprise one or a group of release rate modifiers.

Another preferred dosage form is an oral liquid dosage form, including emulsion, solution, suspension, syrup, and the like. In addition to active ingredients, such an oral liquid dosage form may further comprise inert solvents commonly used in the art, for example water or other solvents, such as ethyl alcohol, isopropanol, propylene glycol, 1,3-butylene glycol, oil (such as cotton seed oil, peanut oil, corn oil, olive oil, flavoring oil and sesame oil), glycerol, polyethylene glycol and sorbitan fatty acid ester, and any combination thereof. In addition to these inert solvents, such an oral liquid dosage form may further comprise humectant, emulsifying agent, suspending agent, sweetening agent, flavoring agent, fragrant agent, and the like.

In addition, the antibody or an antigen binding fragment thereof according to the invention may be present in a unit dosage form in a pharmaceutical composition, for the convenience of administration. The pharmaceutical composition according to the invention should be sterile, and stable under the conditions of manufacture and storage conditions.

The medicament and pharmaceutical composition provided in the invention may be used alone or in combination, or may be used in combination with an additional pharmaceutically active agent (for example, other antiviral agents, e.g. interferon-type agents, such as interferon or pegylated interferon). In some preferred embodiments, the antibody or an antigen binding fragment thereof according to the invention is used in combination with other antiviral agent(s), in order to prevent and/or treat a disease associated with HBV infection. The antibody or an antigen binding fragment thereof according to the invention and such antiviral agent(s) can be administered simultaneously, separately or sequentially. Such antiviral agent(s) include, but are not limited to, interferon-type agents, ribavirin, adamantane, hydroxyurea, IL-2, L-12 and pentacarboxy cytosolic acid, etc.

The pharmaceutical composition according to the invention may comprise "a therapeutically effective amount" or "a prophylactically effective amount" of the antibody or an antigen binding fragment thereof according to the invention. "A prophylactically effective amount" refers to an amount that is sufficient to prevent, suppress or delay the development of a disease (such as HBV infection or a disease associated with HBV infection). "A therapeutically effective amount" refers to an amount that is sufficient to cure or at least partially suppress a disease and its complications in a patient with the disease. The therapeutically effective amount of the antibody or an antigen binding fragment thereof according to the invention may vary depending on the following factors: the severity of a disease to be treated, general state of the immune system in a patient, general conditions of a patient such as age, weight and gender, administration modes of drugs, additional therapies used simultaneously, and the like.

A dosage regimen can be adjusted to provide an optimal desired effect (for example, a therapeutic or prophylactic effect). For example, a single dose may be administered, or multiple doses may be administered within a period of time, or the dose can be proportionally reduced or increased as indicated by the exigencies of the therapeutic situation.

For the antibody or antigen binding fragment thereof according to the invention, an exemplary and non-limiting range for a therapeutically or prophylactically effective amount is from 0.025 to 50 mg/kg, more preferably from 0.1 to 50 mg/kg, more preferably 0.1-25 mg/kg, 0.1-10 mg/kg. It should be noticed that a dose can vary depending on the type and severity of a disease to be treated. In addition, a person skilled in the art understands that for any specific patient, specific dosage regimen should be adjusted over time depending on the patient's need and the professional evaluation made by a doctor; the dose range provided here is only provided for the purpose of exemplification, rather than defining the use or scope of the pharmaceutical composition according to the invention.

Kit and Detection Use

The antibody or antigen-binding fragment thereof of the present invention can specifically bind to HBsAg, so that it can be used to detect the presence or level of HBsAg in a sample.

Therefore, in another aspect, the present invention provides a kit comprising the antibody or antigen-binding fragment thereof of the present invention. In some embodiments, the antibody or antigen-binding fragment thereof of the present invention bears a detectable label. In other embodiments, the kit further comprises a second antibody, which specifically recognizes the antibody or antigen-binding fragment thereof of the present invention. Preferably, the second antibody further comprises a detectable label. Such detectable labels are well known to those skilled in the art, and include, but are not limited to, radioisotope, fluorescent substance, luminescent substance, colored substance and enzyme (for example, horseradish peroxidase) and the like.

In another aspect, the present invention provides a method for detecting the presence or level of HBsAg protein in a sample, which comprises: using the antibody or antigen-binding fragment thereof of the present invention. In some embodiments, the antibody or antigen-binding fragment thereof of the present invention further comprises a detectable label. In other embodiments, the method further comprises using a second antibody carrying a detectable label to detect the antibody or antigen-binding fragment thereof of the present invention. The method can be used for diagnostic purposes, or for non-diagnostic purposes (for example, the sample is a cell sample, not a sample from a patient).

In some embodiments, the method comprises: (1) contacting the sample with the antibody or antigen-binding fragment thereof of the present invention; (2) detecting the formation of a complex between the antibody or antigen-binding fragment thereof and HBsAg protein or detecting an amount of the complex. The formation of the complex indicates the presence of HBsAg protein and/or HBV.

In another aspect, the present invention provides a method for diagnosing whether a subject is infected with HBV, which comprises: using the antibody or antigen-binding fragment thereof of the present invention to detect the presence of HBsAg protein in a sample from the subject. In some embodiments, the antibody or antigen-binding fragment thereof of the present invention further comprises a detectable label. In other embodiments, the method further comprises using a second antibody carrying a detectable label to detect the antibody or antigen-binding fragment thereof of the present invention.

In another aspect, there is provided a use of the antibody or antigen-binding fragment thereof of the present invention in the manufacture of a kit for detecting the presence or level of HBsAg protein in a sample, or for diagnosing whether a subject is infected with HBV.

Definition of Terms

In the present invention, unless otherwise specified, the scientific and technical terms used herein have the meanings commonly understood by those skilled in the art. Moreover, the cell culture, biochemistry, nucleic acid chemistry, immunology laboratory and other operating steps used in this article are all routine steps widely used in the corresponding fields. At the same time, in order to better understand the present invention, definitions and explanations of related terms are provided below.

As used herein, the term "antibody" refers to an immunoglobulin molecule typically composed of two pairs of polypeptide chains, each pair having a light chain (LC) and a heavy chain (HC). Antibody light chains can be classified into κ (kappa) and λ (lambda) light chains. Heavy chains can be classified as μ, δ, γ, α, or ε, and the isotypes of antibody are defined as IgM, IgD, IgG, IgA, and IgE, respectively. Within the light and heavy chains, the variable and constant regions are connected by a "J" region of about 12 or more amino acids, and the heavy chain also comprises a "D" region of about 3 or more amino acids. Each heavy chain is composed of a heavy chain variable region (VH) and a heavy chain constant region (CH). The heavy chain constant region is composed of 3 domains (CH1, CH2, and CH3). Each light chain is composed of a light chain variable region (VL) and a light chain constant region (CL). The light chain constant region is composed of a domain CL. The constant domain does not directly participate in the binding of antibody and antigen, but exhibits a variety of effector functions, such as mediating the binding of immunoglobulin to a host tissue or factor, including various cells of immune system (for example, effector cells) and the first component of classical complement system (C1q). The VH and VL regions can also be subdivided into hypervariable regions (called complementarity determining regions (CDRs)), interspersed with relatively conservative regions called framework regions (FRs). Each VH and VL is composed of 3 CDRs and 4 FRs arranged in the following order: FR1, CDR1, FR2, CDR2, FR3, CDR3, FR4 from the amino terminus to the carboxy terminus. The variable regions (VH and VL) of each heavy chain/light chain pair form antigen binding site respectively. The assignment of amino acids in each region or domain can follow the definitions of Kabat, Sequences of Proteins of Immunological Interest (National Institutes of Health, Bethesda, Md. (1987 and 1991)), or Chothia & Lesk (1987) J. Mol. Biol. 196:901-917; Chothia et al. (1989) Nature 342:878-883.

As used herein, the term "complementarity determining region" or "CDR" refers to amino acid residues in a variable region of an antibody that are responsible for antigen binding. Each of the variable regions of the heavy chain and the light chain contains three CDRs, named CDR1, CDR2, and CDR3. The precise boundaries of these CDRs can be defined according to various numbering systems known in the art, for example, according to the Kabat numbering system (Kabat et al., Sequences of Proteins of Immunological Interest, 5th Ed. Public Health Service, National Institutes of Health, Bethesda, Md., 1991), Chothia numbering system (Chothia & Lesk (1987) J. Mol. Biol. 196:901-917; Chothia et al. (1989) Nature 342:878-883) or IMGT numbering system (Lefranc et al. al., Dev. Comparat. Immunol. 27:55-77, 2003). For a given antibody, those skilled in the art will easily identify the CDRs defined by each numbering system. Moreover, the correspondence between different numbering systems is well known to those skilled in the art (for example, see Lefranc et al., Dev. Comparat. Immunol. 27:55-77, 2003).

In the present invention, the CDRs contained in the antibody or antigen-binding fragment thereof of the present invention can be determined according to various numbering systems known in the art. In certain embodiments, the CDRs contained in the antibody or antigen-binding fragment thereof of the present invention are preferably determined by the Kabat, Chothia or IMGT numbering system. In certain embodiments, the CDRs contained in the antibody or antigen-binding fragment thereof of the present invention are preferably determined by the Kabat numbering system.

As used herein, the term "framework region" or "FR" residues refers to those amino acid residues in a variable region of an antibody other than the CDR residues as defined above.

The term "antibody" is not limited by any specific method for producing the antibody. For example, it comprises recombinant antibody, monoclonal antibody, and polyclonal antibody. The antibody may be an antibody of different isotype, for example, IgG (for example, IgG1, IgG2, IgG3 or IgG4 subtype), IgA1, IgA2, IgD, IgE or IgM antibody.

As used herein, the term "antigen-binding fragment" of antibody refers to a polypeptide comprising a fragment of a full-length antibody that retains the ability to specifically bind to the same antigen to which the full-length antibody binds, and/or competes with the full-length antibody to specifically bind to the antigen, which is also called "antigen binding portion". See generally, Fundamental Immunology, Ch. 7 (Paul, W., ed., 2nd edition, Raven Press, NY (1989), which is incorporated herein by reference in its entirety for all purposes. Antigen-binding fragment of antibody can be produced by recombinant DNA technology or by the enzymatic or chemical cleavage of the intact antibody. Non-limiting examples of antigen-binding fragment include Fab, Fab', F(ab')$_2$, Fd, Fv, complementarity determining region (CDR) fragments, scFv, diabody, single domain antibody, chimeric antibody, linear antibody, nanobody (technology from Domantis), probody and such polypeptides which comprise at least a portion of the antibody that is enough to confer a specific antigen-binding capacity to the polypeptides. Engineered antibody variants are reviewed in Holliger et al., 2005; Nat Biotechnol, 23: 1126-1136.

As used herein, the term "full-length antibody" refers to an antibody composed of two "full-length heavy chains" and two "full-length light chains." "full-length heavy chain" refers to a polypeptide composed of a heavy chain variable region (VH), a heavy chain constant region CH1 domain, a hinge region (HR), a heavy chain constant region CH2 domain and a heavy chain constant region CH3 domain in the N-terminal to C-terminal direction; and, when the full-length antibody is of the IgE isotype, it optionally also comprises a heavy chain constant region CH4 domain. Preferably, the "full-length heavy chain" is a polypeptide chain composed of VH, CH1, HR, CH2, and CH3 in the N-terminal to C-terminal direction. The "full-length light chain" is a polypeptide chain composed of a light chain variable region (VL) and a light chain constant region (CL) in the N-terminal to C-terminal direction. The two pairs of full-length antibody chains are connected by a disulfide bond between CL and CH1 and a disulfide bond between HRs of the two full-length heavy chains. The full-length antibody of the present invention can be derived from a single species, such as human; it can also be a chimeric antibody or a humanized antibody. The full-length antibody of the present invention comprises two antigen binding sites formed by VH and VL pairs respectively, and the two antigen binding sites specifically recognize/bind the same antigen.

As used herein, the term "Fd" refers to an antibody fragment composed of VH and CH1 domains; the term "dAb fragment" refers to an antibody fragment composed of VH domain (Ward et al., Nature 341:544 546 (1989)); the term "Fab fragment" refers to an antibody fragment composed of VL, VH, CL and CH1 domains; the term "F(ab')$_2$ fragment" refers to an antibody fragment composed of two Fab fragments connected by a disulfide bridge on the hinge region; the term "Fab' fragment" refers to a fragment obtained by reducing the disulfide bond connecting the two heavy chain fragments in the F(ab')$_2$ fragment, and is composed of an intact light chain and a Fd fragment (consisting of VH and CH1 domains) of heavy chain.

As used herein, the term "Fv" refers to an antibody fragment composed of a single-arm VL and VH domains of an antibody. Fv fragment is generally considered to be the smallest antibody fragment that can form a complete antigen-binding site. It is generally believed that six CDRs confer antigen-binding specificity to an antibody. However, even one variable region (e.g., Fd fragment, which contains only three antigen-specific CDRs) can recognize and bind to antigen, although its affinity may be lower than the complete binding site.

As used herein, the term "Fc" refers to an antibody fragment that is formed by linking the second, third constant region of a first heavy chain of an antibody and the second, third constant region of a second heavy chain via disulfide bonding. The Fc fragment of an antibody has many different functions, but does not participate in antigen binding.

As used herein, the term "scFv" refers to a single polypeptide chain comprising VL and VH domains, wherein the VL and VH are connected by a linker (see, for example, Bird et al., Science 242:423-426 (1988); Huston et al., Proc. Natl. Acad. Sci. USA 85:5879-5883 (1988); and Pluckthun, The Pharmacology of Monoclonal Antibodies, Vol. 113, Roseburg and Moore eds, Springer-Verlag, New York, pp. 269-315 (1994)). Such scFv molecules may have the general structure: NH$_2$—VL-linker-VH—COOH or NH$_2$—VH-linker-VL-COOH. Suitable prior art linkers consist of repeated GGGGS amino acid sequences or variants thereof. For example, a linker having the amino acid sequence (GGGGS)$_4$ can be used, but variants thereof can also be used (Holliger et al. (1993), Proc. Natl. Acad. Sci. USA 90: 6444-6448). Other linkers that can be used in the present invention are described by Alfthan et al. (1995), Protein Eng. 8:725-731, Choi et al. (2001), Eur. J. Immunol. 31: 94-106, Hu et al. (1996), Cancer Res. 56:3055-3061, Kipriyanov et al. (1999), J. Mol. Biol. 293:41-56 and Roovers et al. (2001), Cancer Immunol. In some cases, there may also be disulfide bonds between the VH and VL of the scFv.

As used herein, the term "diabody" refers to that its VH and VL domains are expressed on a single polypeptide chain, but the used linker is too short to allow pairing between the two domains of the same chain, thereby forcing one domain to pair with the complementary domain of another chain and generating two antigen-binding sites (see, for example, Holliger P. et al., Proc. Natl. Acad. Sci. USA 90: 6444-6448 (1993), and Poljak R J et al., Structure 2:1121-1123 (1994)).

Each of the aforementioned antibody fragments maintains the ability to specifically bind to the same antigen to which the full-length antibody binds, and/or competes with the full-length antibody to specifically bind to the antigen.

Conventional techniques known to those skilled in the art (for example, recombinant DNA technology or enzymatic or chemical fragmentation) can be used to obtain from a given antibody (for example, the antibody provided by the present invention) the antigen-binding fragments of the antibody (for example, the above-mentioned antibody fragments), and can be screened for specificity in the same manner by which intact antibodies are screened.

Herein, unless the context clearly dictates otherwise, when the term "antibody" is referred to, it includes not only intact antibody but also antigen-binding fragments of the antibody.

As used herein, the term "monoclonal antibody", "McAb" and "mAb" have the same meaning and can be used interchangeably. It refers to an antibody or a fragment of an antibody from a population of highly homologous antibody molecules, i.e. a population of completely identical antibody molecules except for natural mutation that may occur spontaneously. A monoclonal antibody has a high specificity for a single epitope of an antigen. Polyclonal antibody, relative to monoclonal antibody, generally comprises at least two or more different antibodies which generally recognize different epitopes on an antigen. In addition, the modifier "monoclonal" merely indicates the character of the antibody as being obtained from a highly homogeneous population of antibodies, and is not to be construed as requiring production of the antibody by any particular method.

As used herein, the term "chimeric antibody" refers to an antibody that a part of its light chain or/and heavy chain is derived from an antibody (which may be derived from a specific species or belong to a specific antibody class or subclass), and another part of its light chain or/and heavy chain is derived from another antibody (which may be derived from the same or different species or belong to the same or different antibody class or subclass), but in any case, it still retains the binding activity to the target antigen (U.S. Pat. No. 4,816,567 to Cabilly et al.; Morrison et al., Proc. Natl. Acad. Sci. USA, 81:6851 6855 (1984)). For example, the term "chimeric antibody" may include such an antibody (e.g., human-mouse chimeric antibody), in which the heavy and light chain variable regions of the antibody are derived from a first antibody (e.g., mouse antibody), while the heavy chain and light chain constant regions of the antibody are derived from a second antibody (e.g., human antibody). In order to prepare a chimeric antibody, the methods known in the art can be used to link immunoglobulin variable regions of an immunized animal to human immunoglobulin constant regions (see, for example, U.S. Pat. No. 4,816,567 to Cabilly et al.). For example, a DNA encoding VH is operably linked to another DNA molecule encoding the heavy chain constant region to obtain a full-length heavy chain gene. The sequence of the human heavy chain constant region gene is known in the art (see, for example, Kabat, E A et al. (1991), Sequences of Proteins of Immunological Interest, Fifth Edition, US Department of Health and Human Services, NIH Publication No. 91-3242), the DNA fragments comprising these regions can be obtained by standard PCR amplification. The heavy chain constant region may be an IgG1, IgG2, IgG3, IgG4, IgA, IgE, IgM, or IgD constant region, but is generally preferably an IgG1 or IgG4 constant region. For example, the DNA encoding VL is operably linked to another DNA molecule encoding the light chain constant region CL to obtain a full-length light chain gene (and a Fab light chain gene). The sequence of the human light chain constant region gene is known in the art (see, for example, Kabat, E A et al. (1991), Sequences of Proteins of Immunological Interest, Fifth Edition, US Department of Health and Human Services, NIH Publication No. 91-3242), and DNA fragments comprising these regions can be obtained by standard PCR amplification. The light chain constant region can be a κ or λ constant region, but is generally preferably a κ constant region.

As used herein, the term "humanized antibody" refers to a genetically engineered non-human antibody, whose amino acid sequence has been modified to increase homology with the sequence of a human antibody. Generally speaking, all or part of the CDR regions of a humanized antibody are derived from a non-human antibody (donor antibody), and all or part of the non-CDR regions (for example, variable region FR and/or constant region) are derived from a human immunoglobulin (receptor antibody). In some embodiments, the CDR regions of the humanized antibody are derived from a non-human antibody (donor antibodies), and all or part of the non-CDR regions (for example, variable region FR and/or constant regions) are derived from a human immunoglobulin (receptor antibody). The humanized antibody generally retains the expected properties of the donor antibody, including, but not limited to, antigen specificity, affinity, reactivity, etc. The donor antibody may be a mouse, rat, rabbit, or non-human primate (for example, cynomolgus monkey) antibody with desired properties (for example, antigen specificity, affinity, reactivity, etc.). In order to prepare the humanized antibody, the methods known in the art can be used to insert the CDR regions of the immunized animal into the human framework sequences (see U.S. Pat. No. 5,225,539 to Winter; U.S. Pat. No. 5,530,101 to Queen et al.; U.S. Pat. Nos. 5,585,089; 5,693,762 and 6,180,370; and Lo, Benny, K C, editor, in Antibody Engineering: Methods and Protocols, volume 248, Humana Press, New Jersey, 2004).

As used herein, the term "germline antibody gene" or "germline antibody gene segment" refers to a sequence present in the genome of an organism encoding immunoglobulin, which has not undergone a maturation process that can lead to genetic rearrangements and mutations for expression of a particular immunoglobulin. In the present invention, the expression "heavy chain germline gene" refers to an germline antibody gene or gene fragment encoding an immunoglobulin heavy chain, which includes V gene (variable), D gene (diversity), J gene (joining) and C gene (constant); similarly, the expression "light chain germline gene" refers to an germline antibody gene or gene fragment encoding an immunoglobulin light chain, which includes V gene (variable), J gene (joining), and C gene (constant). In the present invention, the amino acid sequence encoded by the germline antibody gene or the germline antibody gene fragment is also referred to as "germline sequence". The germline antibody gene or germline antibody gene fragment and their corresponding germline sequences are well known to those skilled in the art and can be obtained or queried from professional databases (e.g., IMGT, unswag, NCBI or VBASE2).

As used herein, the term "specific binding" refers to a non-random binding reaction between two molecules, such as the reaction between an antibody and an antigen to which it is directed. The strength or affinity of a specific binding interaction can be expressed by an equilibrium dissociation constant ($K_D$) of the interaction. In the present invention, the term "$K_D$" refers to a dissociation equilibrium constant of a specific antibody-antigen interaction, which is used to describe the binding affinity between the antibody and the antigen. The smaller the equilibrium dissociation constant, the tighter the antibody-antigen binding, and the higher the affinity between the antibody and the antigen. The specific binding properties between two molecules can be measured using methods known in the art, for example, using surface plasmon resonance (SPR) of BIACORE instrument.

As used herein, the expression "binding at a neutral pH with an affinity higher than that at an acidic pH" or the equivalent expression "pH-dependent binding" refers to that the antibody of the present invention has a $K_D$ value or EC50 value for binding HBsAg at an acidic pH that is higher than its $K_D$ value or EC50 value for binding HBsAg at a neutral pH. The $K_D$ can be measured by a technique known in the art, for example, by SPR technique (for example, Biacore). In the present invention, the term "EC50" refers to an antibody-antigen half maximum effect concentration, that is, an antibody concentration required to reach 50% of the maximum binding effect between a specific antibody-antigen, and it is used to describe the binding capacity between the antibody and the antigen. The smaller the EC50, the higher the binding capacity between the antibody and the antigen. The antibody-antigen half maximum effect concentration (EC50) can be determined using methods known in the art, for example, using an enzyme-linked immunosorbent assay (ELISA) in which an antigen is bound to a solid phase carrier, and the antibody specifically binds to the antigen.

As used herein, "neutralizing antibody" refers to an antibody or antigen-binding fragment thereof that can significantly reduce or completely inhibit the virulence (for example, the ability to infect cells) of the target virus. Generally speaking, neutralizing antibodies can recognize and bind the target virus, and prevent the target virus from entering/infecting the subject's cells. The antibody of the present invention is a neutralizing antibody.

However, it should be understood that in the present application, the virus-neutralizing ability of an antibody is not directly equivalent to the virus-clearing ability of an antibody. As used herein, "neutralizing virus" means that the virulence of a target virus is neutralized (i.e. the virulence of a target virus is significantly reduced or completely inhibited) by inhibiting the target virus from entering/infecting the cell of a subject. As used herein, "clearing virus" means that a target virus (no matter it infects a cell or not) is eliminated from an organism, and therefore the organism turns toward the state before infection by the virus (e.g. the serological test result of virus turns negative). Therefore, in general, neutralizing antibodies do not necessarily have virus-clearing ability. However, in the present application, the inventor surprisingly found that the antibodies according to the invention can not only neutralize HBV, but also clear virus (i.e. can clear HBV DNA and/or HBsAg in vivo, clear HBV and HBV-infected cells in vivo), and therefore have important clinical value.

As used herein, the term "isolated" refers to a state obtained from natural state by artificial means. If a certain "isolated" substance or component is present in nature, it is possible because its natural environment changes, or the substance is isolated from natural environment, or both. For example, a certain un-isolated polynucleotide or polypeptide naturally exists in a certain living animal body, and the same polynucleotide or polypeptide with a high purity isolated from such a natural state is called isolated polynucleotide or polypeptide. The term "isolated" excludes neither the mixed artificial or synthesized substance nor other impure substances that do not affect the activity of the isolated substance.

As used herein, the term "vector" refers to a nucleic acid vehicle into which a polynucleotide can be inserted. When a vector enables the expression of a protein encoded by an inserted polynucleotide, the vector is referred to as an expression vector. A vector can be introduced into a host cell by transformation, transduction or transfection, so that the genetic material elements carried by the vector can be expressed in the host cell. Vectors are well known to those skilled in the art and include, but are not limited to: plasmids; phagemids; cosmids; artificial chromosomes, such as yeast artificial chromosomes (YAC), bacterial artificial chromosomes (BAC) or P1-derived artificial chromosomes (PAC); bacteriophages such as λ phage or M13 phage and animal viruses. Animal viruses that can be used as vectors include, but are not limited to, retroviruses (including lentiviruses), adenoviruses, adeno-associated viruses, herpes viruses (e.g., herpes simplex virus), poxviruses, baculoviruses, papillomaviruses, papovavirus (e.g., SV40). A vector may comprise a variety of elements that control expression, including, but not limited to, promoter sequence, transcription initiation sequence, enhancer sequence, selection element, and reporter gene. In addition, the vector may comprise a replication initiation site.

As used herein, the term "host cell" refers to a cell into which a vector can be introduced, which includes, but is not limited to, prokaryotic cell such as *Escherichia coli* or *Bacillus subtilis*, fungal cell such as yeast cell or *Aspergillus*, insect cell such as S2 *Drosophila* cell or Sf9, or animal cell such as fibroblast, CHO cell, COS cell, NSO cell, HeLa cell, BHK cell, HEK 293 cell or human cell.

As used herein, the term "identity" refers to the match degree between two polypeptides or between two nucleic acids. When two sequences for comparison have the same monomer sub-unit of base or amino acid at a certain site (e.g., each of two DNA molecules has an adenine at a certain site, or each of two polypeptides has a lysine at a certain site), the two molecules are identical at the site. The percent identity between two sequences is a function of the number of identical sites shared by the two sequences over the total number of sites for comparison ×100. For example, if 6 of 10 sites of two sequences are matched, these two sequences have an identity of 60%. For example, DNA sequences: CTGACT and CAGGTT share an identity of 50% (3 of 6 sites are matched). Generally, the comparison of two sequences is conducted in a manner to produce maximum identity. Such alignment can be conducted by using a computer program such as Align program (DNAstar, Inc.) which is based on the method of Needleman, et al. (J. Mol. Biol. 48:443-453, 1970). The percent identity between two amino acid sequences can also be determined using the algorithm of E. Meyers and W. Miller (Comput. Appl.

Biosci., 4:11-17 (1988)) which has been incorporated into the ALIGN program (version 2.0), using a PAM120 weight residue table, a gap length penalty of 12 and a gap penalty of 4. In addition, the percentage of identity between two amino acid sequences can be determined by the algorithm of Needleman and Wunsch (J. Mol. Biol. 48:444-453 (1970)) which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

The twenty conventional amino acids involved herein are expressed in routine manners. See, for example, Immunology-A Synthesis (2nd Edition, E. S. Golub and D. R. Gren, Eds., Sinauer Associates, Sunderland, Mass. (1991)), which is incorporated herein by reference. In the present disclosure, the terms "polypeptide" and "protein" have the same meaning and are used interchangeably. Also in the present disclosure, amino acids are generally represented by single letter and three letter abbreviations as known in the art. For example, alanine can be represented by A or Ala. In addition, as used herein, the terms "monoclonal antibody" and "McAb" have the same meaning and can be used interchangeably; the terms "polyclonal antibody" and "PcAb" have the same meaning and can be used interchangeably.

As used herein, the term "a pharmaceutically acceptable carrier and/or excipient" refers to a carrier and/or excipient pharmacologically and/or physiologically compatible with a subject and an active agent, which is well known in the art (see, e.g., Remington's Pharmaceutical Sciences. Edited by Gennaro A R, 19th ed. Pennsylvania: Mack Publishing Company, 1995), and includes, but is not limited to a pH adjuster, a surfactant, an adjuvant, an ionic strength enhancer, a diluent, an osmotic pressure-controlling agent, an absorption delaying agent, and a preservative. For example, the pH adjuster includes, but is not limited to, phosphate buffer. The surfactant includes, but is not limited to, cationic, anionic, or non-ionic surfactant, e.g. Tween-80. The ionic strength enhancer includes, but is not limited to, sodium chloride. The preservative includes, but is not limited to a variety of antibacterial agents and antifungal agents, such as paraben, chlorobutanol, phenol, and sorbic acid. The osmotic pressure-controlling agent includes, but is not limited to sugar, NaCl and analogs thereof. The absorption delaying agent includes, but is not limited to monostearate and gelatin.

As used herein, the term "prevention/preventing" refers to a method that is carried out in order to suppress or delay the occurrence of a disease, a disorder or a symptom (such as HBV infection or a disease associated with HBV infection) in a subject. As used herein, the term "treatment/treating" refers to a method that is carried out in order to obtain a beneficial or desired clinical outcome. For the purpose of the invention, the beneficial or desired clinical outcome includes, but is not limited to, easing symptom, narrowing the scope of disease, stabilizing (i.e. not aggravating) the state of disease, delaying or slowing the progress of disease, and alleviating symptoms (either partially or completely), no matter detectable or not detectable. In addition, "treatment" also refers to a prolonged survival period compared to the expected survival period (if no treatment is accepted). In the present application, the antibody according to the invention has the ability of neutralizing HBV, and therefore can be used to prevent/protect an unaffected subject or a cell thereof from infection by HBV. In addition, the antibody according to the invention has the ability of clearing HBV (i.e. able to clear HBV DNA and/or HBsAg in vivo, clear HBV and cells infected by HBV in vivo), and therefore can be used to treat HBV infection or a disease associated with HBV infection in an infected subject.

As used herein, the term "subject" refers to a mammal, such as a primate mammal, such as a human.

As used herein, the term "an effective amount" refers to an amount that is sufficient to achieve or at least partially achieve the expected effect. For example, an amount effective for preventing a disease (such as HBV infection or diseases associated with HBV infection) refers to an amount effective for preventing, suppressing, or delaying the occurrence of a disease (such as HBV infection or diseases associated with HBV infection). An effective amount for treating a disease refers to an amount effective for curing or at least partially blocking a disease and its complication in a patient having the disease. The determination of such an effective amount is within the ability of a person skilled in the art. For example, an amount effective for a therapeutic use depends on severity of a disease to be treated, general state of the immune system in a patient, general conditions of a patient, such as age, weight and gender, administration means of drugs, additional therapies used simultaneously, and the like.

Beneficial Effects of the Present Invention

The antibody of the present invention not only can specifically recognize/bind HBsAg, can neutralize the virulence of HBV, can reduce the serum level of HBV DNA and/or HBsAg in the subject, and can effectively eliminate HBV and HBV-infected cells in the body, but also has a significantly enhanced antigen clearance effect and antigen suppression time. It is particularly surprising that it is known in the art that patients with chronic hepatitis B tend to produce immune depletion (tolerance) against HBV due to high levels of HBsAg in the body, thereby prolonging the infection, but the antibody of the present invention can activate the subject (for example patients with chronic HBV infection, or patients with chronic hepatitis B) to regenerate a humoral immune response against HBV, thereby increasing the clinical cure rate. Therefore, the antibody of the present invention is particularly suitable for preventing and treating HBV infection and diseases associated with HBV infection (for example, hepatitis B). In addition, the antibody of the present invention has pH-dependent antigen binding properties, and a single molecule of antibody can bind to multiple molecules of antigens, so that it can also reduce the frequency and dosage of administration, and has great clinical value.

The embodiments of the present invention will be described in detail below in conjunction with the accompanying drawings and examples. However, those skilled in the art will understand that the following drawings and examples are only used to illustrate the present invention, but not to limit the scope of the present invention. According to the accompanying drawings and the following detailed description of the preferred embodiments, various objects and advantageous aspects of the present invention will become apparent to those skilled in the art.

BRIEF DESCRIPTION OF THE DRAWINGS

FIG. 4A: the detection results of binding to HBsAg at pH 7.4 and pH 6.0 for the phage library of the pH-dependent scFv antibody derived from M1D after the third round of screening, wherein the abscissa represents the phage antibody number or dilution factor, the ordinate represents the OD value. The results show that these single clones all have strong antigen binding activity and have a significant decrease in binding activity at pH 6.0. FIG. 4B: the detection results of pH-dependent binding to HBsAg for the 6 single clones with high $OD_{(450/630)}$ value at pH 7.4 in the third round and showing the largest difference in $OD_{(450/630)}$ values at pH7.4 and pH 6.0, with 8 gradients and 3-fold dilution, in which the abscissa represents the dilution factor, the ordinate represents the OD value. The results show that the pH-dependent antigen binding effect is better presented after gradient dilution, among which A31-73 shows the best effect. FIG. 4C: the preliminary results of pH-dependent binding detection of scFv antibody phage to HBsAg for the 24 excellent candidates of phage-scFv after the fourth round of screening with 4 gradients and 5-fold dilution, in which the abscissa represents the dilution factor, the ordinate represents the OD value. The results show that A41-8, A42-12, and A42-23 are better than A31-73, while A44-1 and A44-20 are equivalent to A31-73.

FIG. 5 shows a summary of the mutation sites of A31-73, A42-13, A42-23 and A41-8.

FIG. 6 shows the HPLC results of A31-73, A42-12, A42-23 and A41-8 in Example 2, in which M1D-C/S is a positive control, referring to different batches of M1D antibodies, and it can be seen from the results that the four antibodies are single-component.

FIG. 8A: the clearance effect of HBsAg in mouse serum, wherein the abscissa represents the number of days after antibody injection (d), and the ordinate represents the level of HBsAg in the mouse serum after clearance (log10 IU/ml). FIG. 8B: the change of the antibody concentration in mouse serum, wherein the abscissa represents the number of days after antibody injection (d), and the ordinate represents the antibody concentration (Log10 ng/ml). The results show that the HBsAg level of M1D rebounds back to the baseline after about 10 days, while our modified antibodies rebound back to the baseline after about 15 days; regarding the antibody concentration in the serum, M1D has the lowest antibody concentration on the day 10, while the three modified antibodies still can be detectable on the day 15, indicating that the pH-dependent modified antibodies show an ability of clearing HBsAg comparable to that of the parent, and they have an antigen inhibition time longer than that of the parent, that is, their clearance effect can be exerted for a longer time.

As shown in FIG. 9, the scavenger antibody is located outside the cell and acts as a "transport helper" for reciprocally transporting antigens into the cell, the antibody half-life can thus be extremely prolonged, and it can bind to antigen again, thereby improving the cell entry efficiency of antigens, and greatly improving the clearance efficiency.

FIG. 13A: the clearance effect of HBsAg in mouse serum, wherein the abscissa represents the number of days after antibody injection (d), and the ordinate represents the clearance level of HBsAg in mouse serum (log10 IU/ml). FIG. 13B: the clearance effect of HBV DNA in mouse serum, wherein the abscissa represents the number of days after antibody injection (d), and the ordinate represents the clearance level of HBV DNA in mouse serum (log10 IU/ml). FIG. 13C: change in the antibody concentration in mouse serum, wherein the abscissa represents the number of days after antibody injection (d), and the ordinate represents the antibody concentration (Log 10 ng/ml). The results show that the scavenger antibodies have an antigen clearance ability comparable to that of M1D, but have a longer inhibition time. After M1D exerts the maximum antigen clearance effect, the antigen quickly begins to rebound, and M1D starts to fail on the day 14, and the HBsAg in serum returns to the baseline level (based on the negative control 16G12). However, after the two scavenger antibodies exert their maximum clearance effect, they can still maintain a low antigen level for a long time, and rebound slowly. In the A41-8 V4 treatment group, HBsAg rebounds back to the baseline in about 30 days. A31-73 V4 showed a better performance, after the expected end of the experiment, HBsAg still does not return to the baseline level, which is consistent with the detection results of antibody half-life in serum.

FIG. 17A: the clearance effect of HBsAg in mouse serum, wherein the abscissa represents the number of days after antibody injection (d), the ordinate represents the level of HBsAg in mouse serum after clearance (log10 IU/ml). FIG. 17B: the clearance effect of HBV DNA in mouse serum, wherein the abscissa represents the number of days after antibody injection (d), and the ordinate represents the clearance level of HBV DNA in mouse serum (log10 IU/ml). FIG. 17C: change in the antibody concentration in mouse serum, wherein the abscissa represents the number of days after antibody injection (d), and the ordinate represents the antibody concentration (ng/ml). The results show that the scavenger antibody A31-73 DY with DY modification is more than an order of magnitude stronger than M1D in antigen clearance. A31-73 DY can not only quickly clear HBsAg in HBV transgenic mice, but also effectively reduce the HBV DNA titer in mice, which is consistent with the detection results of antibody half-life in serum. Comparing the antibody concentration in serum, the half-life of A31-73 DY is longer than that of M1D by nearly 8 days, which shows that the scavenger antibody A31-73 DY has the function of reciprocally binding antigen, thereby increasing the time of antigen clearance.

FIG. 18A: a schematic diagram of this animal experiment, the number represents the number of days, the red arrow represents the time point of blood collection, and the white arrow represents the time point of administration. FIG. 18B: the clearance effect of HBsAg in mouse serum, wherein the abscissa represents the number of days after antibody injection (d), and the ordinate represents the clearance level of HBsAg in mouse serum (log10 IU/ml). FIG. 18C: relative titers of Anti-HBs in mouse serum, wherein the abscissa represents the name of antibody, and the ordinate represents the relative titer of Anti-HBs (log10 OD450/OD630). The results show that the scavenger antibody A31-73 DY breaks through the limitation of traditional antibodies and achieves the treatment at low-dose and low-frequency, the HBsAg titer in mice is long-term inhibited at a level of below 100 IU/mL, and the humoral immune response is activated in muse after treatment, allowing the production of Anti-HBs.

SEQUENCE INFORMATION

Figure 1:
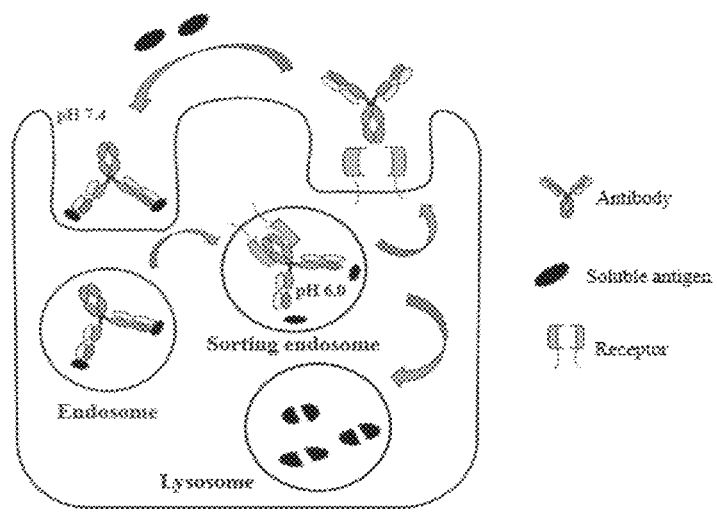
FIG. 1 shows a schematic diagram of the working principle of an antibody with pH-dependent antigen-binding activity. Human plasma is neutral, with a pH of about 7.4, while the intracellular environment is acidic, with a pH of about 6.0. An antibody with pH-dependent antigen-binding activity can bind to an antigen in the plasma, the antigen-antibody complex is then internalized into the cell. The pH-dependent antibody will dissociate from the antigen in the acidic environment of the endosome. The antibody dissociated from the antigen will be captured by FcRn and circulated to the outside of the cell. In the extracellular neutral environment, the FcRn releases the antibody, and the antibody returned to the plasma can bind to other antigen again, thereby realizing the cycle use of the antibody.

The information of partial sequences involved in the present invention is provided in Table 1 below.

TABLE 1

Description of sequences

| SEQ ID NO | Description | Sequence information |
|---|---|---|
| 1 | A31-73 VH | QVQLQESGPGLVKPSETLSLTCTVSGGSIHSNFWSWIRQPPGKGLE WIGYISGPGHHTDYNPSLKSRVTISVDTSKNQFSLKLSSVTAADTA VYYCARSHDYGHHDYAFDFWGQGTTVTVSS |
| 2 | A31-73 A42-12 VK | DIQMTQSPSSLSASVGDRVTITCRATQDISSSLNWYQQKPGKAPKL LIYYANRLQSGVP.SRFSGSGSGTDFTLTISSLQPEDFATYYCQQYH YLPLTFGGGTKVEIK |
| 3 | A42-12 VH | QVQLQESGPGLVKPSETLSLTCTVSGGSIHHNFWSWIRQPPGKGLE WIGYIHGPGHYTDYNPSLKSRVTISVDTSKNQFSLKLSSVTAADTA VYYCARSHDYGSNDYAFDFWGQGTTVTVSS |

TABLE 1-continued

Description of sequences

| SEQ ID NO | Description | Sequence information |
|---|---|---|
| 4 | A42-23 VH | QVQLQESGPGLVKPSETLSLTCTVSGGSITHNFWSWIRQPPGKGLE WIGYISGYDTYTDYNPSLKSRVTISVDTSKNQFSLKLSSVTAADTA VYYCARSHDYGHHDYAFDFWGQGTTVTVSS |
| 5 | A42-23 VK | DIQMTQSPSSLSASVGDRVTITCRATQDIHHSLNWYQQKPGKAPK LLIYYANRLQSGVP.SRFSGSGSGTDFTLTISSLQPEDFATYYCQQY HYLPLTFGGGTKVEIK |
| 6 | A41-8 VH | QVQLQESGPGLVKPSETLSLTCTVSGGSITSNFWSWIRQPPGKGLE WIGYISGSGTYTDYNPSLKSRVTISVDTSKNQFSLKLSSVTAADTA VYYCARSHHYGSNDYAFDFWGQGTTVTVSS |
| 7 | A41-8 VK | DIQMTQSPSSLSASVGDRVTITCRATQDISYSLNWYQQKPGKAPK WYYANRLQSGVP.SRFSGSGSGTDFTLTISSLQPEDFATYYCQQY HYLPLTFGGGTKVEIK |
| 8 | A31-73 HCDR1 | GGSIHSNFW |
| 9 | A31-73 HCDR2 | SGPGHHT |
| 10 | A31-73 A42-23 HCDR3 | ARSHDYGHHDYAFDF |
| 11 | MID A31-73 A42-12 LCDR1 | QDISSS |
| 12 | MID A31-73 A42-12 A42-23 A41-8 LCDR2 | YAN |
| 13 | A31-73 A42-12 A42-23 A41-8 LCDR3 | QQYHYLPLT |
| 14 | A42-12 HCDR1 | GGSIHHNFW |
| 15 | A42-12 HCDR2 | HGPGHYT |
| 16 | MID A42-12 HCDR3 | ARSHDYGSNDYAFDF |
| 17 | A42-23 HCDR1 | GGSITHNFW |
| 18 | A42-23 HCDR2 | SGYDTYT |
| 19 | A42-23 LCDR1 | QDIHHS |
| 20 | MID A41-8 HCDR1 | GGSITSNFW |
| 21 | MID A41-8 HCDR2 | SGSGTYT |
| 22 | A41-8 HCDR3 | ARSHHYGSNDYAFDF |
| 23 | A41-8 LCDR1 | QDISYS |
| 24 | MID HFR1 | QVQLQESGPGLVKPSETLSLTCTVS |
| 25 | MID HFR2 | SWIRQPPGKGLEWIGYI |

TABLE 1-continued

Description of sequences

| SEQ ID NO | Description | Sequence information |
|---|---|---|
| 26 | MID HFR3 | DYNPSLKSRVTTSVDTSKNQFSLKLSSVTAADTAVYYC |
| 27 | MID HFR4 | WGQGTTVTVSS |
| 28 | M1D LFR1 | DIQMTQSPSSLSASVGDRVTITCRAT |
| 29 | M1D LFR2 | LNWYQQKPGKAPKLLIY |
| 30 | M1D LFR3 | RLQSGVP.SRFSGSGSGTDFTLTISSLQPEDFATYYC |
| 31 | M1D LFR4 | FGGGTKVEIK |
| 32 | Primer | 5'>GTTATTACTCGTGGCCCAGCCGGCCATGGCACAGGTGCAGCTGCAGGAG<3' |
| 33 | Primer | 5'>CACTCCAGACCCTTCCCTGGGGGCTGGCGGATCCAGCTCCAGAAGTTGYKGKKGATGYKGYSGYSAGAGAC<3' |
| 34 | Primer | 5'>CCAGGGAAGGGTCTGGAGTGGATTGGGTATATCYMTGGTYMTSRTMMTYATMMCGACTACAACCCCTC<3' |
| 35 | Primer | 5'>CCCTTGGCCCCAGAAATCAAAAGCGTRGTSGTKGYKGYSGTRGTSGTGCGATCTCGCACAGTAATAC<3' |
| 36 | Primer | 5'>CCTCCACTCCCGCCTCCACCTGAAGAGACGGTGACGGTGGTCCCTTGGCCCCAGAAAT<3' |
| 37 | Primer | 5'>TGGAGGCGGGAGTGGAGGTGGCGGATCTGGAGGGGGTGGTAGCGACATACAGATGACGCAG<3' |
| 38 | Primer | 5'>TGCTGATACCAATTTAAAGAACTGCTAATGTCSTGAGTTGCCCGGCAAGTG<3' |
| 39 | Primer | 5'>TCTTTAAATTGGTATCAGCAAAAACCGGGGAAAGCCCC<3' |
| 40 | Primer | 5'>CACCTTGGTCCCTCCGCCGAAAGTGAGGKGTAAACTATGGTRCTGTTGACAGTAATAAGT<3' |
| 41 | Primer | 5'>TAGTCGACCAGGCCCCCGAGGCCTTTGATTTCCACCTTGGTCCCTCCGCC<3' |
| 42 | Primer | 5'-AGTAGCAACTGCAACCGGTGTACATTCTCAGGTGCAGCTGCAGGAGTC |
| 43 | Primer | 5'-GATGGGCCCTTGGTCGACGCTGAAGAGACGGTGACGGTGG |
| 44 | Primer | 5'-AGTAGCAACTGCAACCGGTGTACATTCTGACATACAGATGACGCAGTCTC |
| 45 | Primer | 5'-ATGGTGCAGCCACCGTACGTTTGATTTCCACCTTGGTCC |
| 46 | M1D LCDR3 | QQYHSLPLT |
| 47 | Human IgG1 heavy chain constant region with V4 mutation | ASTKGPSVFPLAPSSKSTSGGTAALGCLVKDYFPEPVTVSWNSGALTSGVHTFPAVLQSSGLYSLSSVVTVPSSSLGTQTYTCNVNHKPSNTKVDKKVEPKSCDKTHTCPPCPAPELLGGPSVFLFPPKPKDTLYTSRTPEVTCVVVDVSHEDPEVKFNWYVDGVEVHEAKTKPREEQYNSTYRVVSVLTVLHQDWLNGKEYKCKVSNKALPAPTEKTTSKAKGQPREPQVYTLPPSRDELTKNQVSLTCLVKGFYPSDTAVEWESNGQPENNYKTTPPVLDSDGSFFLYSKLTVDKSRWQQGNVFSCSVMHEALHYHYTQKSLSLSPGK |
| 48 | Human IgG1 heavy chain | ASTKGPSVFPLAPSSKSTSGGTAALGCLVKDYFPEPVTVSWNSGALTSGVHTFPAVLQSSGLYSLSSVVTVPSSSLGTQTYICNVNHKPSN |

TABLE 1-continued

Description of sequences

| SEQ ID NO | Description | Sequence information |
|---|---|---|
|  | constant region with DY mutation | TKVDKKVEPKSCDKTHTCPPCPAPELLGGPSVFLFPPKPKDTLMIS RTPEVTCVVVDVSHEDPEVKFNWYVDGVEVHNAKTKPREEQYN STYRVVSVLTVLHQDWLNGKEYKCKVSNDAYPAPTEKTT SKAKGQPREPQVYTLPPSRDELTKNQVSLTCLVKGFYPSDIAVEW ESNGQPENNYKTTPPVLDSDGSFFLYSKLTVDKSRWQQGNVFSCS VMHEALHNHYTQKSLSLSPGK |
| 49 | Signal peptide | MGWSCIILFLVATATGVHS |
| 50 | General formula of HCDR1 | GGSIX$_1$X$_2$NFW |
| 51 | General formula of HCDR2 | X$_3$GX$_4$X$_5$X$_6$X$_7$T |
| 52 | General formula of HCDR3 | ARSHX$_8$YGX$_9$X$_{10}$DYAFDF |
| 53 | General formula of LCDR1 | QDIX$_{11}$X$_{12}$S |
| 54 | General formula of LCDR3 | QQYHX$_{13}$LPLT |
| 55 | IGHV4-4*08 | QVQLQESGPGLVKPSETLSLTCTVSGGSISSYYWSWIRQPPGKGLE WIGYIYTSGSTNYNPSLKSRVTISVDTSKNQFSLKLSSVTAADTAV YYCAR |
| 56 | IGKV1-39*01 | DIQMTQSPSSLSASVGDRVTITCRASQSISSYLNWYQQKPGKAPKL LIYAASSLQSGVPSRFSGSGSGTDFTLTTSSLQPEDFATYYCQQSYS TP |
| 57 | Human IgG1 heavy chain constant region | ASTKGPSVFPLAPSSKSTSGGTAALGCLVKDYFPEPVTVSWNSGA LTSGVHTFPAVLQSSGLYSLSSVVTVPSSSLGTQTYICNVNHKPSN TKVDKKVEPKSCDKTHTCPPCPAPELLGGPSVFLFPPKPKDTLMIS RTPEVTCVVVDVSHEDPEVKFNWYVDGVEVHNAKTKPREEQYN STYRVVSVLTVLHQDWLNGKEYKCKVSNKALPAPTEKTISKAKG QPREPQVYTLPPSRDELTKNQVSLTCLVKGFYPSDIAVEWESNGQ PENNYKTTPPVLDSDGSFFLYSKLTVDKSRWQQGNVFSCSVMHE ALHNHYTQKSLSLSPGK |
| 58 | Human κ light chain constant region | RTVAAPSVFIFPPSDEQLKSGTASVVCLLNNFYPREAKVQWKVDS ALQSGNSQESVTEQDSKDSTYSLSSTLTLSKADYEKHKVYACEVT HQGLSSPVTKSFNRGEC |

EXAMPLES

The present invention will now be described with reference to the following examples which are intended to illustrate the present invention rather than limit the present invention.

Unless otherwise specified, the molecular biology experimental methods and immunoassay methods used in the present invention basically refer to J. Sambrook et al., Molecular Cloning: Laboratory Manual, 2nd Edition, Cold Spring Harbor Laboratory Press, 1989, and F M Ausubel et al., Compiled Molecular Biology Experiment Guide, 3rd edition, John Wiley & Sons, Inc., 1995; the restriction enzymes were used in accordance with the conditions recommended by the product manufacturer. Those skilled in the art know that the examples describe the present invention by way of example, and are not intended to limit the scope of protection claimed by the present invention.

Figure 2:
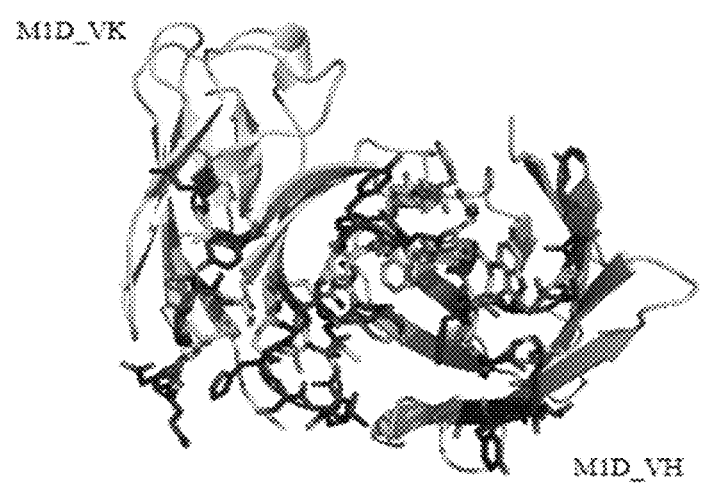
FIG. 2 shows a simulation of the three-dimensional structure of M1D variable region. The rod structure represents the CDR region, the blue represents the VK CDR, the green represents the VH CDR, and the red represents the surface amino acids. A total of 25 surface amino acids can be found in the CDR region.

Example 1: Phage Screening of pH-Dependent Anti-HBsAg Antibody 1.1 Determination of Mutation Site for pH-Dependent Antibody Modification The anti-HBV humanized antibody M1D (described in detail in Chinese Patent Application 201810307136.5) previously developed in the laboratory was used as the parent antibody, its variable regions were modified for pH-dependent antigen binding. As shown in FIG. 1, the modified M1D could maintain the antigen-binding activity under neutral conditions, but had a significant decrease in antigen-binding activity under acidic conditions; the dissociated modified M1D could bind to intracellular FcRn so as to return to the plasma and bind to antigen again, so that one molecule of M1D after pH-dependent antigen binding modification could repeatedly bind to and neutralize a plurality of molecules of antigens. Histidine could be protonated under acidic conditions and was a key amino acid to bring pH-dependent antigen binding properties. The three-dimensional structure of the variable regions of M1D was simulated (the three-dimensional structure of the variable regions was simulated according to the amino acid sequences of the variable regions) and shown in FIG. 2. The stick-shaped structure represented the CDR region, the blue represented the VK CDR, the green represented the VH CDR, and the red represented the surface amino acids. A total of 25 surface amino acids were found in the CDR regions, combined with the experience gained from the amino acids disclosed in the literatures, it was determined that there were 24 random replacement sites for histidine.

1.2 Phage Library Construction of pH-Dependent scFv Antibodies Derived from M1D

Figure 3:
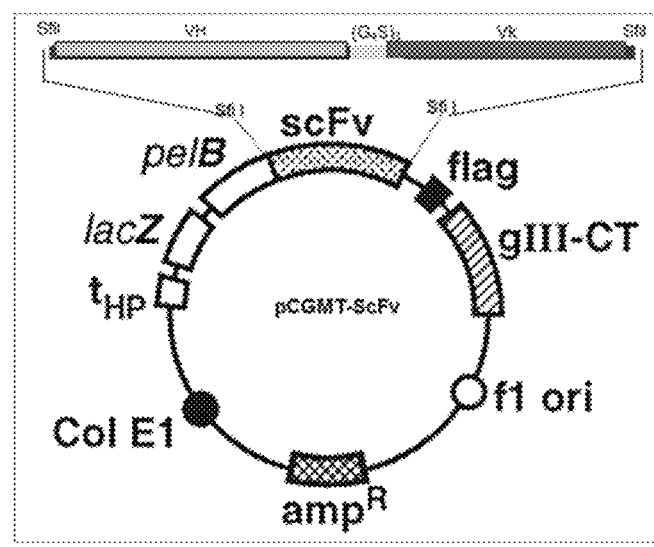
FIG. 3 shows a schematic diagram of the recombinant vector (pCGMT-scFv) encoding the scFv antibody, in which the structure of the scFv antibody is: $NH_2$—VH-linker-VL-COOH.

Using the variable regions of the light and heavy chains of the M1D antibody as a template, the 24 sites determined in the antibody variable region CDRs were replaced with histidines, and the target fragments were amplified according to the primers in Table 2 to obtain the gene fragments coding the pH-dependent scFv antibodies derived from MID. PCR conditions were: 95° C., 5 min; 95° C., 30 s; 57° C., 30 s; 72° C., 30 s; 72° C., 10 min; for 25 amplification cycles; SOE-PCR reaction conditions were: 95° C., 5 min; 95° C., 30 s; 57° C., 30 s; 72° C., 30 s; 72° C., 10 min; for 5 amplification cycles. The amplified products were analyzed by agarose gel electrophoresis, and the amplification products were recovered/purified by using the DNA purification and recovery kit (TianGen, DP214-03), thereby obtaining the gene fragments H—K encoding the pH-dependent scFv antibodies derived from M1D. The structure of scFv antibodies was: $NH_2$—VH-linker-VL-COOH, and the linker sequence could be $(G_4S)_3$. Each of the gene fragments H—K was digested with SfiI, and then ligated to the vector pCGMT (from Scripps, *Making chemistry selectable by linking it to infectivity*) at a molar ratio of 10:1 (gene fragment:vector). The ligation products were transformed into competent *Escherichia coli* ER2738 by electroporation (electroporation conditions: 25 μF, 2.5 KV, 200Ω). The transformed *Escherichia coli* was recovered in SOC medium for 45 min, and then 200 μL of bacterial solution was plated on LB plates (comprising 100 g/L ampicillin+tetracycline+2 g/mL glucose), and incubated by standing at 37° C. overnight. All colonies on the plates were the libraries that the mutation sites determined in the variable regions were randomly mutated into histidine, which were used for subsequent screening. Monoclonal colonies were picked out from the plates and sequenced to ensure the correctness of the sequences of recombinant vectors encoding the scFv antibodies. The schematic diagram of the recombinant vector (pCGMT-scFv) encoding the scFv antibody was shown in FIG. 3.

TABLE 2

Mutant primers for pH-dependent scFv antibodies derived from M1D

| Primer name | Sequence |
|---|---|
| VH-F | SEQ ID NO: 32 |
| HCDR1-R | SEQ ID NO: 33 |
| HCDR2-F | SEQ ID NO: 34 |
| HCDR3-R | SEQ ID NO: 35 |
| VH-R | SEQ ID NO: 36 |
| VK-F | SEQ ID NO: 37 |
| KCDR1-R | SEQ ID NO: 38 |
| KCDR2-F | SEQ ID NO: 39 |
| KCDR3-R | SEQ ID NO: 40 |
| VK-R | SEQ ID NO: 41 |

1.3 Screening of pH-Dependent scFv Antibodies

The library obtained in the previous step was screened for multiple rounds, and the positive monoclonal colonies obtained in the screening were cultured with 2×YT medium comprising ampicillin (100 g/L) and glucose (2 g/mL) to reach an OD value of 0.6, and then M13KO7 was added for auxiliary super-infection. After 2 h, 100 g/L of kanamycin was added and super-infection was performed at 37° C. After 2 h, the culture was centrifuged at 4000 rpm for 10 min, the supernatant was discarded, and the cell pellet was collected. The cell pellet was resuspended in a medium comprising ampicillin and kanamycin (100 g/L), and cultured under shaking at 30° C. overnight. Subsequently, the culture was centrifuged at 12000 rpm for 10 min, the cells and supernatant were collected, and stored at 4° C. for testing.

Figure 4A:
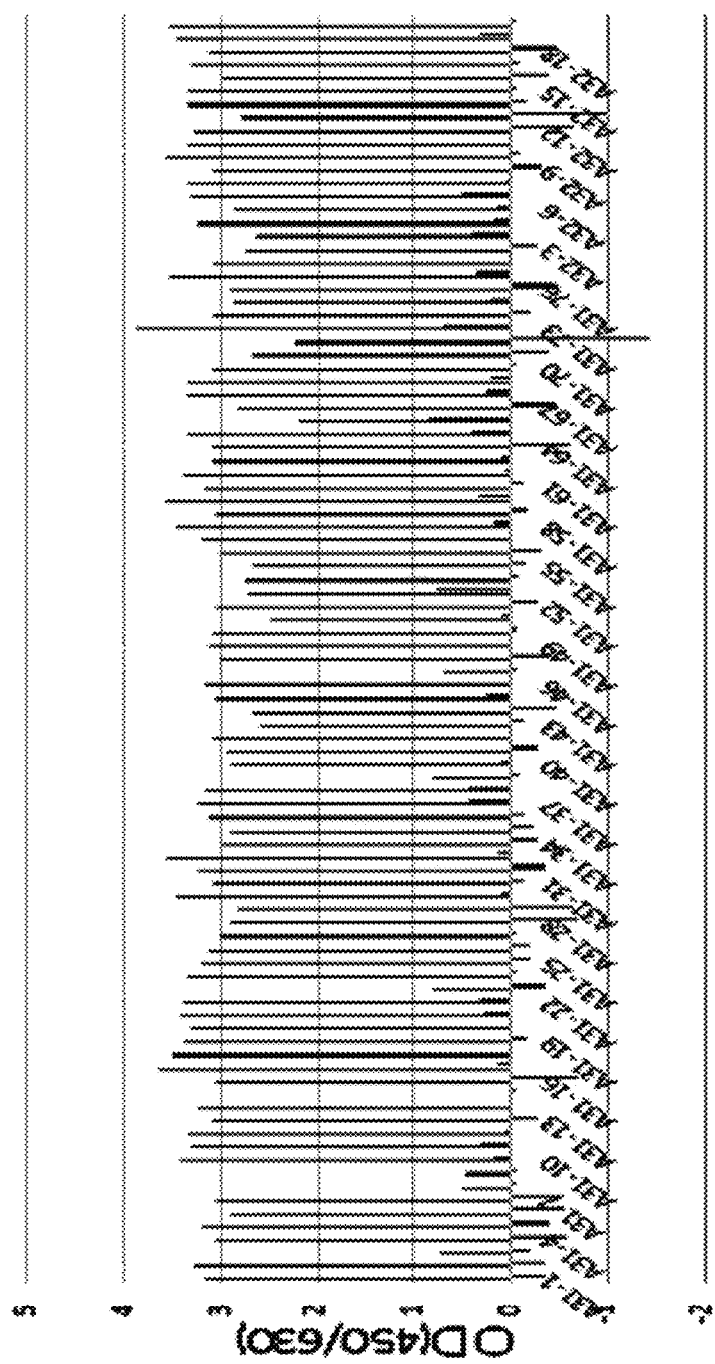
FIGS. 4A to 4C show the ELISA results of the phage library displaying the pH-dependent scFv antibody derived from M1D and the antigen HBsAg.
Figure 4B:
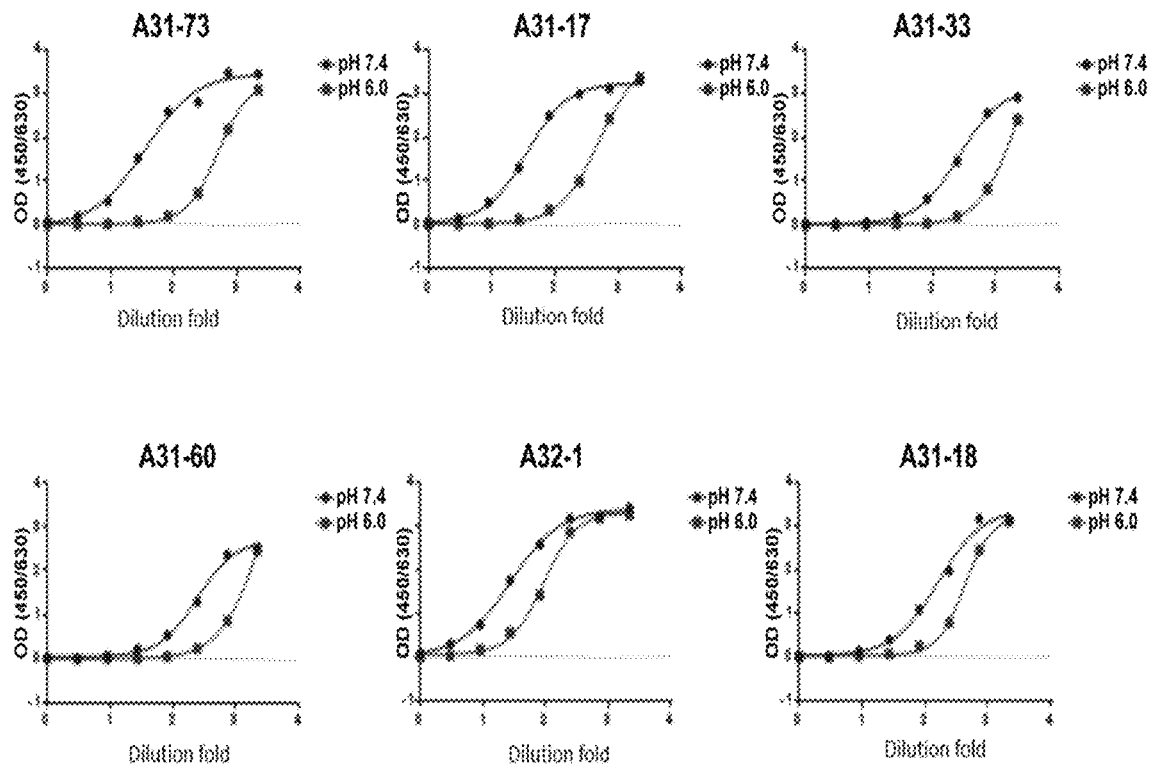
Figure 4C:
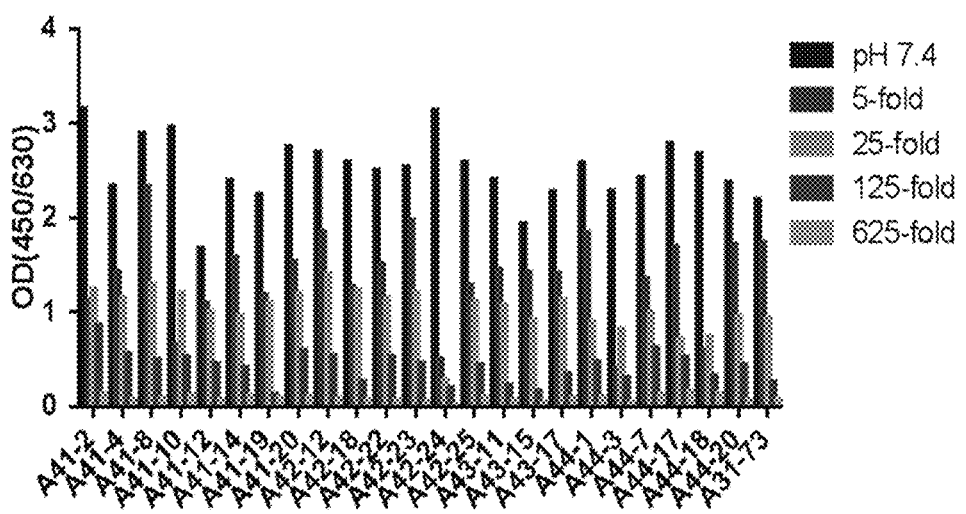

The ELISA plate coated with HBsAg (200 ng/mL) antigen was taken, 100 μL of the supernatant to be tested was added to each well, and incubation was performed at 37° C. for 1 h (two wells for each supernatant). Subsequently, the ELISA plate was washed once with PBST, and then 120 μL of pH 7.4 PBS and pH 6.0 PBS were added to the two wells of each supernatant respectively and incubated at 37° C. for 30 min. Washing was performed 5 times with PBST of corresponding pH, 100 μL of anti M13-HRP diluted 1:5000 was added, and incubated at 37° C. for 30 min. Subsequently, the ELISA plate was washed 5 times with PBST, and the substrate TMB solution was added. After 15 minutes of color development, the color reaction was terminated with $H_2SO_4$, and the reading was measured at $OD_{450/620}$. The results of the third round of ELISA testing were shown in FIGS. 4A to 4C. The results of FIGS. 4A to 4C showed that the phages displaying these scFv antibodies all had reactivity in ELISA detection and could weakly bind to the antigen at pH 6.0. 4 strains of pH-dependent phage antibodies with good effects were initially obtained, named A31-73, A42-13, A42-23 and A41-8.

Example 2: Preparation of pH-Dependent Anti-HBsAg Antibody 2.1 Construction of Recombinant Vector for Eukaryotic Expression In the present invention, a large amount of antibody recombination needed to be carried out, so it was necessary to construct a set of light and heavy chain vectors that can efficiently recombine antibodies. In the present invention, the existing eukaryotic expression vector pTT5 in the laboratory was specially modified to construct a set of light and heavy chain recombinant vectors for double plasmid co-transfection. MGWSCIILFLVATATGVHS (SEQ TD NO: 49) was used as the signal peptide for the light and heavy chains. The sequences encoding the constant regions of the human antibody light and heavy chains were separately ligated to the downstream of signal peptide to construct a set of eukaryotic expression vectors pTT5-CH, pTT5-Cκ and pTT5-Cλ that facilitated antibody recombination.

The four scFv antibodies obtained in 1.3 were used to amplify the light and heavy chain variable region fragments with the primers in Table 3. The specific amplification reaction conditions were: 95° C., 5 min; 95° C., 30 s; 57° C., 30 s; 72° C., 30 s; 72° C., 10 min; for 25 amplification cycles. And the amplification products were recovered from the gel.

The laboratory-made Gibson assembly solution was used to ligate the above constructed eukaryotic expression vector with the recovered PCR product of antibody variable region gene (the primer carried a sequence homologous to the vector) to obtain the recombinant vectors VH+pTT5-CH (comprising the heavy chain constant region shown in SEQ ID NO: 57) and VH+pTT5-Cκ (comprising the light chain constant region shown in SEQ ID NO: 58). The recombinant vector was transformed into *E. coli* DH5a strain, plated on LB plate, and cultivated overnight in a 37° C. incubator. Monoclonal colonies were picked out from the plate and sequenced, and the sequencing results were subjected to sequence comparison using MEGA to confirm the correctness of its genes, and exclude the genes with wrong information.

TABLE 3

Primers for construction of eukaryotic expression vectors

| Primer | Primer sequence |
|---|---|
| VH-F | SEQ ID NO: 42 |
| VH-R | SEQ ID NO: 43 |
| VK-F | SEQ ID NO: 44 |
| VK-R | SEQ ID NO: 45 |

2.2 Small- and Large-Scale Expression of Antibody Genes

The constructed recombinant vectors VH+pTT5-CH and VH+pTT5-Cκ were co-transfected into HEK293 cells, and double plasmids for small-scale expression were co-transfected into a 24-well plate, 500 μL per well; if the cell supernatant of small-scale expression had antigenic activity, the transfection system was enlarged to 100 mL (determined by the amount of antibody used) of FreeStyle™ 293F suspension cells (the cell density was about $2\times10^6$ cells/ml). The transfected cells were cultured in a shake flask in a 32° C., 5% $CO_2$ incubator, and the supernatant was collected after 7 days of expression.

2.3 Antibody Purification

The cell expression supernatant was collected and purified with a Protein A column according to the manufacturer's instructions. The specific steps were as follows: the harvested cell culture supernatant was centrifuged at 8000 rpm for 10 min, the supernatant was retained, the pH value was adjusted to 8.4 with dry powder $Na_2HPO_4$, and then filtered with a filter membrane with 0.22 μm pore diameter. 10 mL of Sepharose 4B medium coupled with Protein A was loaded into column, it was connected to AKTA Explorer100 system, the pump A was connected to 0.2 M disodium hydrogen phosphate solution, and the pump B was connected to 0.2 M citric acid solution. Detection wavelength was UV 280 nm, flow rate was 5 mL/min, and the sample injection proportion of pumps A/B was adjusted. The column was first washed with 100% B (pH 2.3) to remove protein impurities, the pH was balanced with 10% B (pH 8.0), the signal at the detection wavelength returned to zero after it was stable, then the sample was loaded. After the flow through peak passed, 10% B was used for balance until the signal at the detection wavelength was reduced to zero and was stable, elution was performed using 70% B (pH 4.0), and the elution peak was collected. The elution peak sample was dialyzed into PBS buffer and subjected to assay of concentration and SDS-PAGE and HPLC analysis to determine the purity of IgG antibody. The HPLC results of A31-73, A42-12, A42-23 and A41-8 were shown in FIG. 6, and the four antibodies are single-component.

Example 3: Property Analysis and Functional Evaluation of pH-Dependent Anti-HBsAg Antibodies The 4 strains of phage antibodies with property of pH-dependent binding to HBsAg that were obtained through the preliminary screening by the method of Example 1 were named as A31-73, A42-13, A42-23 and A41-8, respectively. Furthermore, the four strains of phage antibodies were subjected to the eukaryotic expression and purification by the method of Example 2. The VH and VL amino acid sequences of the four antibodies were shown in the table below. In addition, the CDR sequences of the four antibodies were determined, and the amino acid sequences of the CDRs of the heavy chain variable regions and the light chain variable regions were shown in Table 5. The mutation sites that endowed A31-73, A42-13, A42-23 and A41-8 with the property of pH-dependent antigen-binding to HBsAg were summarized in Table 5.

TABLE 4

Amino acid sequences of A31-73/A42-12/A42-23/A41-8 light and heavy chain variable regions

| Sequence name | SEQ ID NO | Amino acid sequence |
|---|---|---|
| A31-71 VH | 1 | QVQLQESGPGLVKPSETLSLTCTVSGGSILISNFWSWIRQPPG KGLEWIGYISGPGFIFITDYNPSLKSRVTISVDTSKNQFSLKLSS VTAADTAVYYCARSHDYGHHDYAFDFWGQGTTVTVSS |
| A31-73 VK | 2 | DIQMTQSPSSLSASVGDRVTITCRATQDISSSLNWYQQKPGK APKLLIYYANRLQSGVP.SRFSGSGSGTDFTLTISSLQPEDFAT YYCQQYHYLPLTFGGGTKVEIK |
| A42-12 VH | 3 | QVQLQESGPGLVKPSETLSLTCTVSGGSIHHNFWSWIRQPPG KGLEWIGYIFIGPGHYTDYNPSLKSRVTISVDTSKNQFSLKLSS VTAADTAVYYCARSHDYGSNDYAFDFWGQGTTVTVSS |
| A42-12 VK | 2 | DIQMTQSPSSLSASVGDRVTITCRATQDISSSLNWYQQKPGK APKLLIYYANRLQSGVP.SRFSGSGSGTDFTLTISSLQPEDFAT YYCQQYHYLPLTFGGGTKVEIK |
| A42-23 VH | 4 | QVQLQESGPGLVKPSETLSLTCTVSGGSITHNFWSWIEtQPPG KGLEWIGYISGYDTYTDYNPSLKSRVTISVDTSKNQFSLKLSS VTAADTAVYYCARSHDYGHHDYAFDFWGQGTTVTVSS |

TABLE 4-continued

Amino acid sequences of A31-73/A42-12/A42-23/A41-8 light and heavy chain variable regions

| Sequence name | SEQ ID NO | Amino acid sequence |
|---|---|---|
| A42-23 VK | 5 | DIQMTQSPSSLSASVGDRVTITCRATQDIFIHSLNAVYQQKPGK APKLLIYYANRLQSGVP.SRFSGSGSGTDFTLTISSLQPEDFAT YYCQQYHYLPLTFGGGTKVEIK |
| A41-8 VH | 6 | QVQLQESGPGLVKPSETLSLTCTVSGGSITSNFWSWIFtQPPGK GLEWIGYISGSGTYTDYNPSLKSRVTISVDTSKNQFSLKLSSV TAADTAVYYCARSHHYGSNDYAFDFWGQGTTVTVSS |
| A41-8 VK | 7 | DIQMTQSPSSLSASVGDRVTITCRATQDISYSLNWYQQKPGK APKLLIYYANRLQSGVP.SRFSGSGSGTDFTLTISSLQPEDFAT YYCQQYHYLPLTFGGGTKVEIK |

TABLE 5

Sequence of A31-73/A42-12/A42-23/A41-8 light and heavy chain CDRs

| | | | |
|---|---|---|---|
| A31-73 | | | |
| VH CDR1 | GGSHASNFW | SEQ ID NO: | 8 |
| VH CDR2 | SGPGHHT | SEQ ID NO: | 9 |
| VH CDR3 | ARSFIDYGHHDYAFDF | SEQ ID NO: | 10 |
| VL CDR1 | QDISSS | SEQ ID NO: | 11 |
| VL CDR2 | YAN | SEQ ID NO: | 12 |
| VL CDR3 | QQYHYLPLT | SEQ ID NO: | 13 |
| A42-12 | | | |
| VH CDR1 | GGSIFIFINFW | SEQ ID NO: | 14 |
| VH CDR2 | HGPGHYT | SEQ ID NO: | 15 |
| VH CDR3 | ARSHDYGSNDYAFDF | SEQ ID NO: | 16 |
| VL CDR1 | QDISSS | SEQ ID NO: | 11 |
| VL CDR2 | YAN | SEQ ID NO: | 12 |
| VL CDR3 | QQYHYLPLT | SEQ ID NO: | 13 |
| A42-23 | | | |
| VH CDR1 | GGSITHNFW | SEQ ID NO: | 17 |
| VH CDR2 | SGYDTYT | SEQ ID NO: | 18 |
| VH CDR3 | ARSHDYGFIFIDYAFDF | SEQ ID NO: | 10 |
| VL CDR1 | QDIHHS | SEQ ID NO: | 19 |
| VL CDR2 | YAN | SEQ ID NO: | 12 |
| VL CDR3 | QQYHYLPLT | SEQ ID NO: | 13 |
| A41-8 | | | |
| VH CDR1 | GGSITSNFW | SEQ ID NO: | 20 |
| VH CDR2 | SGSGTYT | SEQ ID NO: | 21 |
| VH CDR3 | ARSHHYGSNDYAFDF | SEQ ID NO: | 22 |
| VL CDR1 | QDISYS | SEQ ID NO: | 23 |
| VL CDR2 | YAN | SEQ ID NO: | 12 |
| VL CDR3 | QQYHYLPLT | SEQ ID NO: | 13 |

3.1 Determination of Antigen-Binding Activity of pH-Dependent Anti-HBsAg Antibodies at Different pH The present inventors tested the ability of pH-dependent antigen binding to HBsAg for A31-73, A42-12, A42-23 and A41-8 respectively by ELISA method. First, BCA protein quantification kit was used to determine the concentration of the purified antibody, and the antibody concentrations were unified to 1111.11 ng/mL by dilution. Subsequently, 20% NBS was used to perform the gradient dilution of antibody concentration by 3-fold gradient dilution, and a total of 8 concentrations were obtained by the gradient dilution. Subsequently, the diluted antibody was added to a commercial HBsAg plate (purchased from Beijing Wantai), and incubated at 37° C. for 1 h (two wells per supernatant). Subsequently, the ELISA plate was washed once with PBST and spin-dried. Then 120 μL of PBS with pH 7.4 and pH 6.0 were added to the two wells of each supernatant and incubated at 37° C. for 30 min. The plate was washed 5 times with PBST of corresponding pH and spin-dried. Subsequently, GAH-HRP-labeled secondary antibody was added, incubated for 30 min, the plate was washed 5 times with PBST, and spin-dried. And the substrate TMB solution was added. After 15 minutes of color development, the color reaction was terminated with $H_2SO_4$, and the reading was measured at OD450/630.

Figure 7:
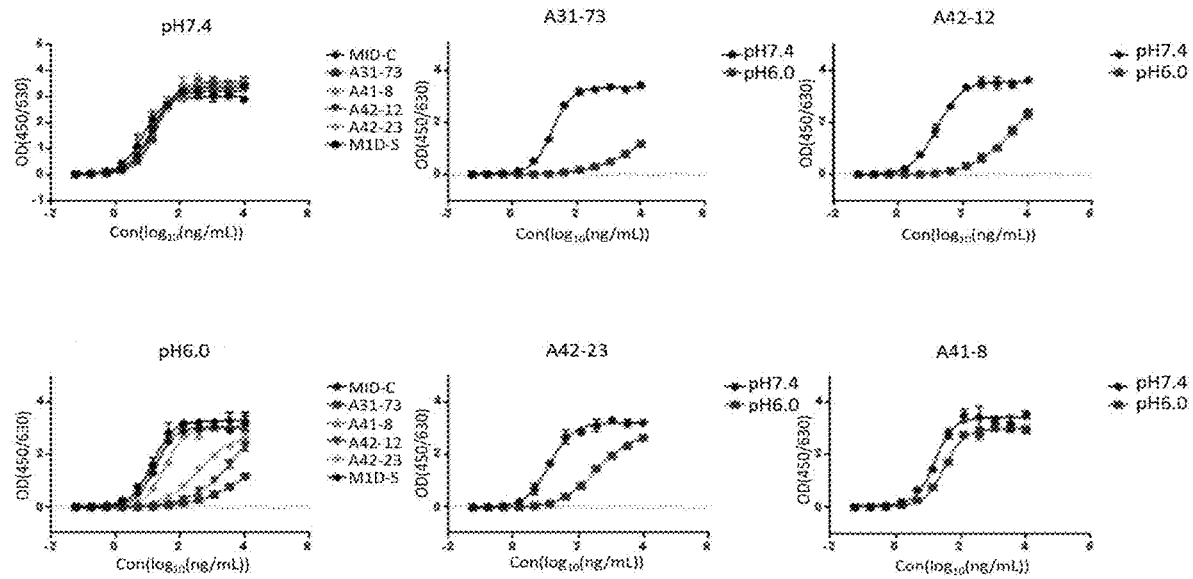
FIG. 7 shows the detection results of binding to HBsAg at pH 7.4 and pH 6.0 for A31-73, A42-12, A42-23 and A41-8 in Example 3, in which the abscissa represents the antibody concentration (Log 10 ng/ml), the ordinate represents the OD value. The results show that the four antibodies all can maintain the equivalent antigen-binding activity at neutral pH of the parent antibody, and all have a significant decrease in the antigen-binding activity under the condition of pH 6.0, in which A31-73 is better than A42-12, A42-23 and A41-8.

The results were shown in FIG. 7. At pH 7.4, all of A31-73, A42-12, A42-23 and A41-8 had an antigen-binding activity comparable to that of M1D, but at pH 6.0, their antigen-binding activities were significantly reduced. The EC50 results were summarized in Table 6.

TABLE 6

EC50 for pH-dependent activity detection of A31-73, A42-12, A42-23 and A41-8

| Antibody | EC50 in pH 6.0 (ng/mL) | EC50 in pH 7.4 (ng/mL) | EC50(pH 6.0)/ EC50(pH 7.4) |
|---|---|---|---|
| A31-73 | 14046.00 | 17.32 | 810.97 |
| A42-12 | 4604.00 | 15.13 | 304.30 |
| A42-23 | 345.00 | 12.68 | 27.21 |
| A41-8 | 31.13 | 15.78 | 1.97 |

3.2 Determination of Therapeutic Effect of pH-Dependent Anti-HBsAg Antibodies in Animal Model HBV transgenic mice were used to evaluate the ability of the above-mentioned pH-dependent anti-HBsAg antibodies to eliminate HBV virus in animals. The pH-dependent anti-HBsAg antibodies and the parental antibody M1D were administered to HBV transgenic mice (presented by Professor Chen Peizhe, National Taiwan University) at a dose of 10 mg/kg via tail vein injection, with 4 to 5 HBV transgenic mice per group. Subsequently, blood samples were collected from the mice through retro-orbital venous plexus, and the changes in HBsAg and antibody levels in mouse serum were detected.

3.2.1 Quantitative Detection of HBsAg (1) Preparation of reaction plate: the mouse monoclonal antibody HBs-45E9 was diluted with 20 mM PB buffer ($Na_2HPO_4/NaH_2PO_4$ buffer, pH 7.4) to 2 µg/mL, 100 µL of coating solution was added to each well of a chemiluminescence plate to perform coating at 2-8° C. for 16-24 h, followed by another 2 hours at 37° C., the plate was washed once with PBST washing solution, and spin-dried. After washing, 200 µL of blocking solution was added to each well to perform blocking at 37° C. for 2 h. Subsequently, the blocking solution was discarded, and the plate was dried in a drying room, and stored at 2-8° C. for later use.

(2) Sample dilution: the collected mouse serum was diluted with a PBS solution comprising 20% NBS (newborn bovine serum) to form two gradients of 1:30 and 1:150 for subsequent quantitative detection.

(3) Sample denaturation treatment: 15 µL of the above-diluted serum sample was fully mixed with 7.5 µL of denaturation buffer (15% SDS, dissolved in 20 mM PB7.4), and reacted at 37° C. for 1 h. Then, 90 µL of stop buffer (4% CHAPS, dissolved in 20 mM PB7.4) was added and mixed well.

(4) Sample reaction: 100 µL of the above-mentioned denatured serum sample was added to a reaction plate, and reacted at 37° C. for 1 hour. Subsequently, the reaction plate was washed 5 times with PBST and spin-dried.

(5) Enzymatic label reaction: HBs-A6A7-HRP reaction solution was added to the chemiluminescence plate at 100 µL/well, and reacted at 37° C. for 1 h. Then, the plate was washed 5 times with PBST and spin-dried.

(6) Luminescence reaction and measurement: a luminescence solution was added (100 µL/well) to the chemiluminescence plate, and light intensity detection was performed.

(7) Calculation of HBsAg concentration in mouse serum sample: parallel experiments were performed using standard products, and a standard curve was drawn based on the measurement results of the standard products. Then, the light intensity measurement value of the mouse serum sample was substituted into the standard curve, and the concentration of HBsAg in the serum sample to be tested was calculated.

3.2.2 Quantitative Detection of Antibody in Serum (1) Sample dilution: the serum samples were diluted with 20% NBS into 3 gradients: 1000 times, 10000 times, 100000 times; the corresponding control antibody was diluted with 20% NBS to 20 ng/mL in the first well, and then 3 times diluted into 6 gradients, (3) Sample addition: 100 µL/well of the sample diluted in the previous step and corresponding antibody diluent were added to a commercial HBsAb plate (purchased from Beijing Wantai), and incubated 37° C. for 1 h.

(4) Washing: the plate was washed 5 times with 300 µL/well of PBST by a plate washer, and spin-dried;

(5) Adding enzyme-labeled secondary antibody: 100 µL/well of GAH-HRP-labeled secondary antibody diluent was added, and incubated at 37° C. for 30 min;

(6) Washing: the plate was washed 5 times with 300 µL/well of PBST by a plate washer, and spin-dried.

(7) Color development: 100 µL/well of color development solution, 37° C., 10-15 min;

(8) Stop and read: 50 µL/well of stop solution was added, the reading value was measured at OD450/630 within 10 minutes by a microplate reader.

(9) Calculation of antibody concentration in mouse serum sample: a standard curve was drawn based on the measurement results of corresponding standard antibodies. Then, the light intensity measurement value of the mouse serum sample was substituted into the standard curve, and the antibody concentration in the serum sample to be tested was calculated.

Figure 8A:
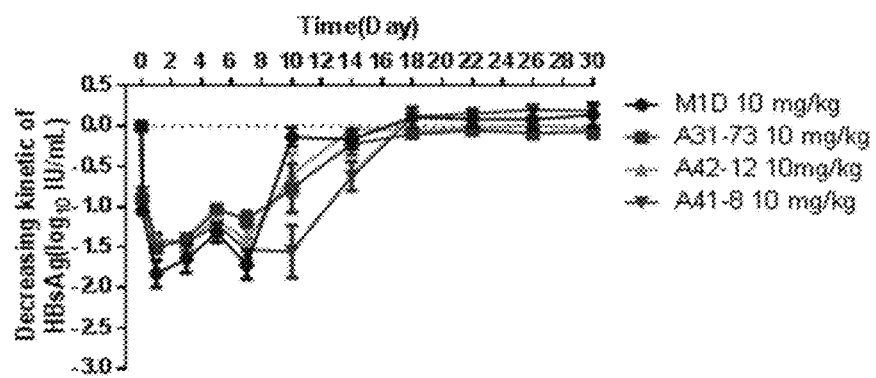
FIGS. 8A to 8B show the results of the therapeutic effect of A31-71, A41-8, A42-12 and the parental M1D in HBV transgenic female mice in Example 3.
Figure 8B:
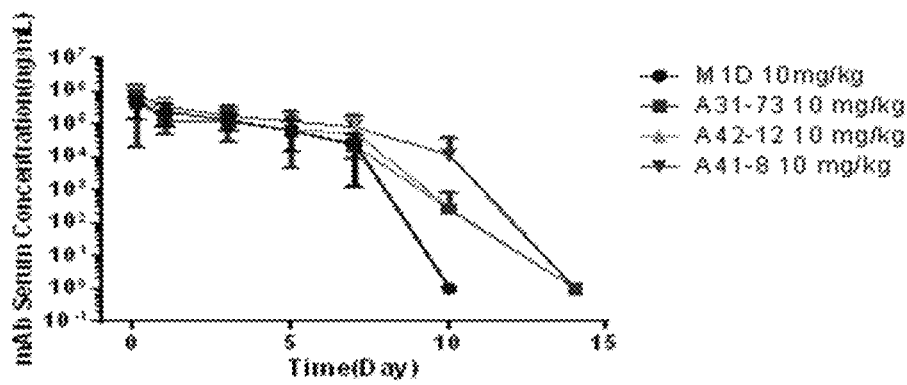

The detection results of HBsAg and antibody levels in the serum of mice after antibody treatment were shown in FIGS. 8A to 8B. The results showed that the HBsAg level of the parent antibody M1D rebounded back to the baseline in about 10 days, while the HBsAg level of pH-dependent antibodies rebounded back to the baseline in about 15 days; comparing the antibody concentrations in serum, M1D showed the lowest antibody concentration on the $10^{th}$ day, while the three pH-dependent antibodies still can be detectable on the $15^{th}$ day, indicating that the pH-dependent antibodies had an antigen inhibition time longer than that of the parent antibody while maintaining the ability to eliminate HBsAg which is equivalent to that of the parent antibody, that was, the clearance effect of pH-dependent antibodies could be exerted for a longer time. The clearance results of HBsAg by A31-73, A42-12 and A41-8 were shown in FIG. 8A, and the results of serum concentrations of A31-73, A42-12 and A41-8 were shown in FIG. 8B. The results of animal treatment effects indicated that A31-73, A42-12 and A41-8 had a potential to treat HBV infection or a disease associated with HBV infection (for example, hepatitis B).

Example 4: Construction and Functional Evaluation of Scavenger Antibody

Figure 9:
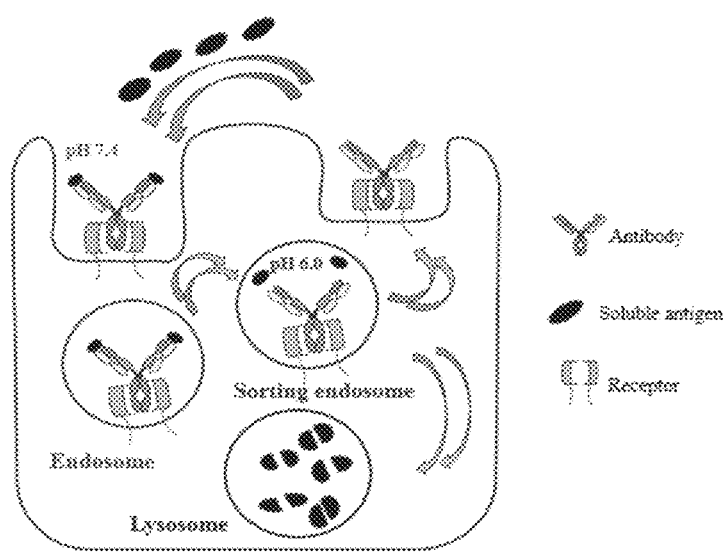
FIG. 9 shows the working principle of scavenger antibody. The pH-dependent antigen binding activity plays a role in cells. Thus, if this first limiting factor of cell entry is not broken, the pH-dependent antigen-binding properties will not be applied subsequently, and the benefit of modification will be greatly reduced. A scavenger antibody obtained by further mutation of amino acids in the Fc region can enhance the binding to hFcRn receptor at neutral pH, or enhance the binding to FcγRs receptor.

The pH-dependent antibody needs to enter the cell to exert its pH-dependent antigen-binding activity. Therefore, if the first limiting factor of cell entry is not broken, the subsequent pH-dependent antigen-binding properties will have no chance to "play". Therefore, in this example, the scavenger antibody was obtained by further mutation of amino acids in the Fc region, which could enhance the binding to hFcRn receptor at neutral pH, or enhance the binding to FcγRs receptor. As shown in FIG. 9, the scavenger antibody is located outside the cell and played the role of a "transportation helper" that reciprocally transported antigens into the cell, thereby extremely extending the antibody half-life, and it could bind to antigen again, thereby improving the efficiency of cell entry of antigen, and significantly improving the clearance efficiency.

Figure 10:
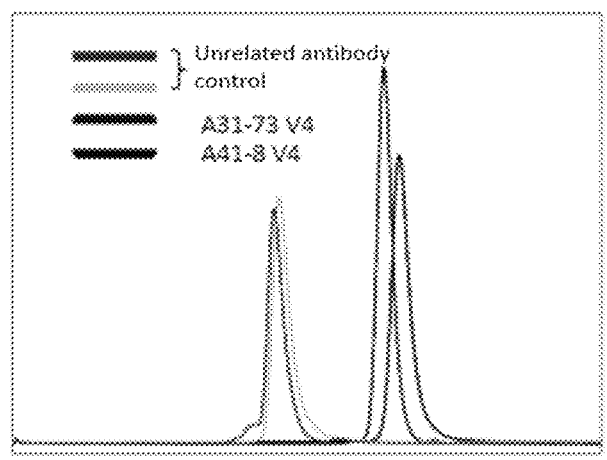
FIG. 10 shows the HPLC results of two molecules A31-73 and A41-8 in Example 4, in which the red and the green represent irrelevant positive controls. It can be seen from the results that all antibodies are single-component.

4.1 Scavenger Antibody Capable of Binding to hFcRn 4.1.1 Construction. Expression and Purification of Scavenger Antibody Capable of Binding to hFcRn The A31-73 and A41-8 with the best performance in HBV transgenic mice in Example 3 were subjected to V4 (M252Y, N286E, N434Y) mutation in Fc region (this work was commissioned to General Biology, order number: G120460) to enhance the affinity to hFcRn under neutral conditions. Two scavenger antibodies A31-73 V4 and A41-8 V4 were obtained, and the heavy chain constant region after mutation was shown in SEQ ID NO:47. The above two antibodies were subjected to large-scale eukaryotic expression and purification, which specific operation steps were shown in Examples 2.2 and 2.3. The HPLC results of A31-73 V4 and A41-8 V4 were shown in FIG. 10, and the results indicated that the antibodies are single-component.

Figure 11:
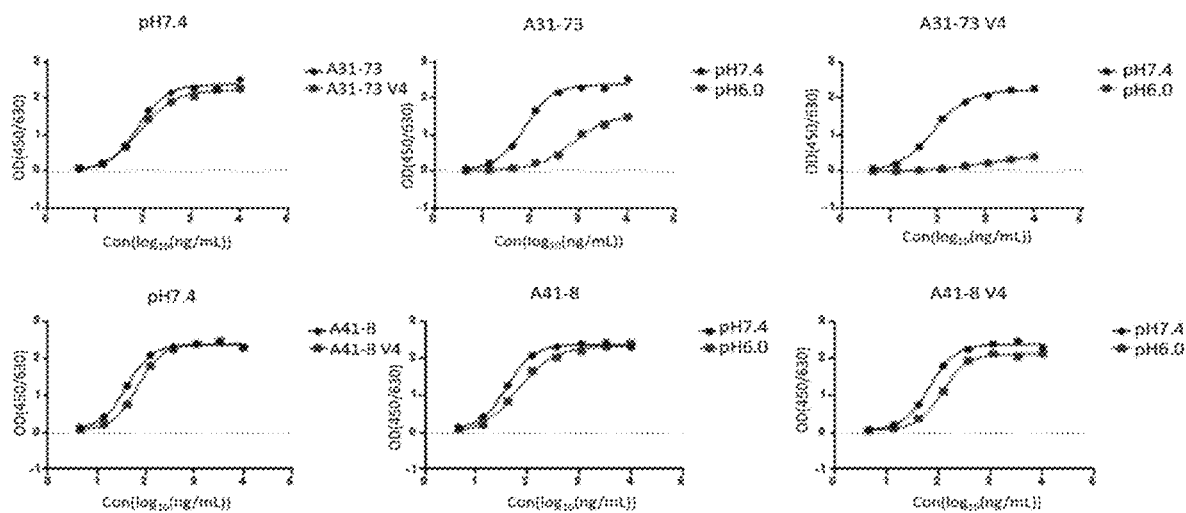
FIG. 11 shows the detection results of binding to HBsAg at pH 7.4 and pH 6.0 for A31-73 V4 and A41-8 V4 in Example 4, in which the abscissa represents the antibody concentration (Log10 ng/ml), and the ordinate represents OD value. The results show that both molecules can maintain the antigen-binding activity and pH-dependent antigen-binding activity at neutral pH of the parent antibody, and the pH-dependent antigen-binding activity is slightly enhanced.

4.1.2 In Vitro Activity Detection of Scavenger Antibody Capable of Binding to hFcRn 4.1.2.1 Determination of Antigen Binding Activity of Scavenger Antibody Capable of Binding to hFcRn at Different pH The antigen binding activities of A31-73 V4 and A41-8 V4 at pH 7.4 and pH 6.0 were detected respectively, specific operation steps of which were shown in Example 3.1. The results were shown in FIG. 11. The results showed that both A31-73 V4 and A41-8 V4 could maintain an antigen-binding activity equivalent to that of the parent at neutral pH, and the antigen-binding activity at acidic pH was further weakened, indicating that the pH-dependent antigen binding activities of A31-73 V4 and A41-8 V4 were enhanced to a certain extent.

4.1.2.2 Function Verification at Cellular Level of Scavenger Antibody Capable of Binding to hFgRn 4.1.2.2.1 Labeling HBsAg with 488 Fluorescence The labeling of 1 mg of HBsAg was taken as an example, and the whole process was protected from light.

(1) 1 mL of 1 mg/mL HBsAg was dialyzed into borate buffer (PH 8.5, 500 mL) at 4° C. for 4 h;

(2) The molar ratio of HBsAg to 488 label was 1:5, and 0.1988 mg of 488 fluorescence was required after calculation;

(3) 10 mg/mL of 488 fluorescence solution was prepared with DMF and mixed well;

(4) 19.88 μL of 488 fluorescence was added to 1 mL of the dialyzed HBsAg, mixed well, and incubated at room temperature for 1 h;

(5) The incubation mixture was dialyzed into PBS at 4° C. overnight.

4.1.2.2.2 Immunofluorescence Experiment Based on MDCK Cells (all steps involving the fluorescence labelled sample were operated in a dark environment)

(1) Cell plating: the cells at a density of $2 \times 10^5$ cells/mL were cultured in a 24-well glass-bottom culture plate for cell imaging overnight at 250 μL/well;

(2) the antibody and antigen labeled with the corresponding fluorescence were diluted in serum-free medium: 800 ng/mL for antigen, and 2 μg/mL for antibody;

(3) 125 μL each of the antigen and antibody were mixed uniformly, and then allowed to stand for 1 hour in a 37° C., $CO_2$ incubator;

(4) the cell supernatant in the cell imaging culture plate was discarded, the antigen-antibody complex was added, shaken evenly, and allowed to stand in a $CO_2$ incubator at 37° C. for 2 hours;

(5) the supernatant was discarded, 1 mL of sterile PBS incubated at 37° C. in advance was used to "wash" the cell surface 3 to 5 times, and removed by pipetting;

(6) 1 mL of 10% paraformaldehyde was added, and allowed to stand for 0.5 h in a 37° C., $CO_2$ incubator protected from light;

(7) the paraformaldehyde was discarded, 1 mL of sterile PBS incubated at 37° C. in advance was used to "wash" the cell surface 3 to 5 times, and removed by pipetting;

(8) 0.5 mL of DAPI (diluted at 1:1000 with sterile PBS) was added, and allowed to stand for 15 minutes in a 37° C., $CO_2$ incubator protected from light;

(9) the DAPI diluent was discarded, 1 mL of sterile PBS incubated at 37° C. in advance was used to "wash" the cell surface for 3~5 times, and removed by pipetting, and 0.5 mL of PBS was added, and placed in a high-content imager for imaging.

Figure 12A:
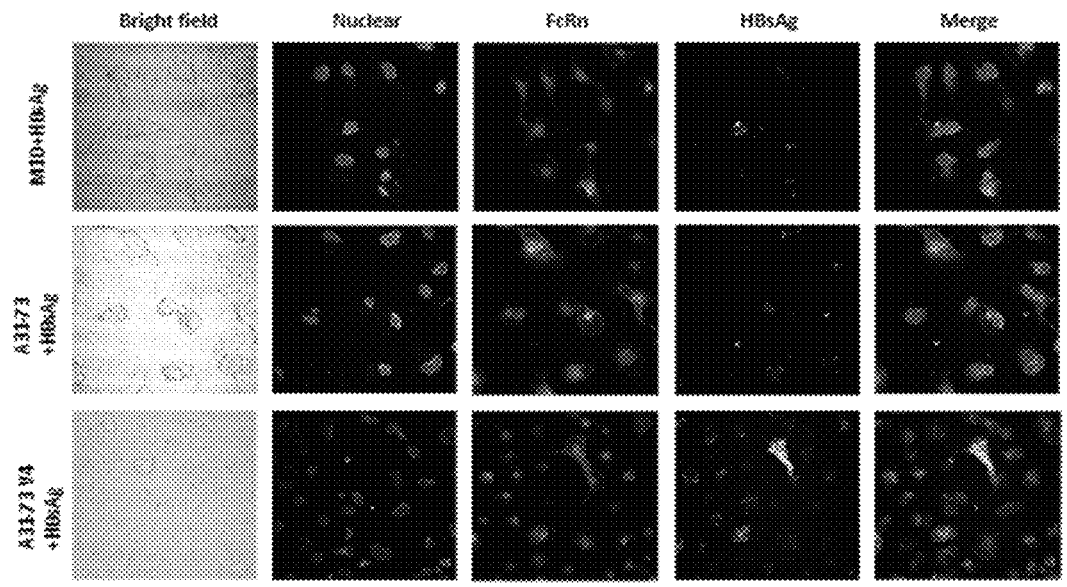
FIGS. 12A to 12B show the immunofluorescence results on MDCK cell of A31-73 V4 and A31-73 (FIG. 12A), and A41-8 V4 and A41-8 (FIG. 12B) in Example 4. The green fluorescence represents hFcRn, the blue fluorescence represents the nucleus, and the red fluorescence represents HBsAg. The results show that the antigen fluorescence intensities in the cells treated with A31-73 V4 and A41-8 V4 variants are significantly higher than those of the cells treated with A31-73 and A41-8, indicating that the scavenger antibody with V4 modification can efficiently transport more antigens into the cells. It is confirmed that the V4 mutation in the scavenger antibody can enhance the binding of antibody to hFcRn under neutral conditions. After the antigen-antibody complex enters the cell, the antigen-antibody complex is dissociated under the intracellular pH of only about 6.0, and the antibody returns to the cell surface to perform the antigen-binding function again. The enhancement of scavenger antibody's ability to bind to hFcRn under neutral conditions can improve the subsequent pH-dependent antigen-binding properties.
Figure 12B:
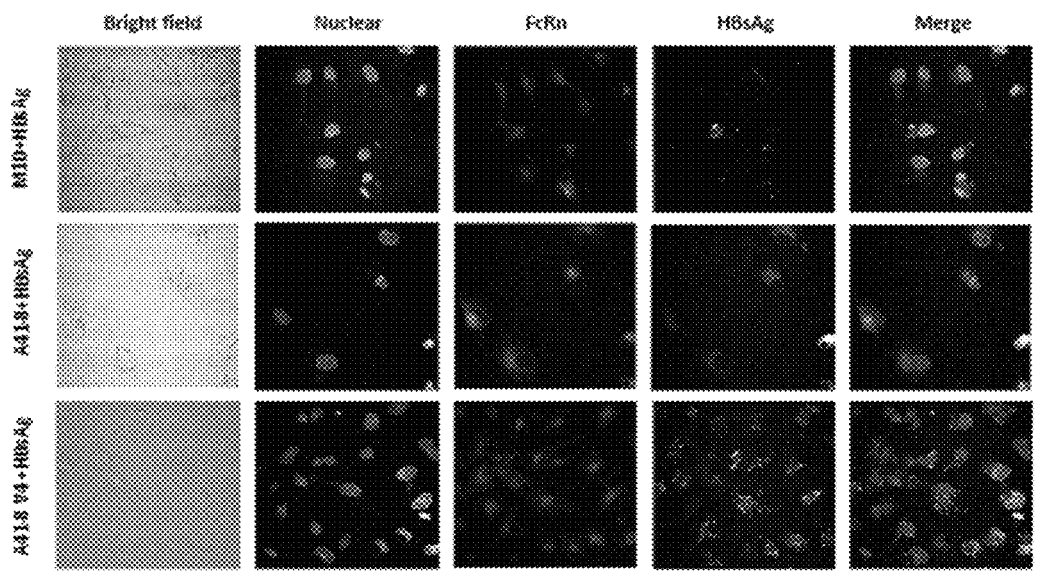

The experimental results were shown in FIGS. 12A to 12B. The results showed that the antigen fluorescence intensity in cells treated with A31-73 V4 and A41-8 V4 was significantly higher than that of cells treated with A31-73 and A41-8, indicating that the above scavenger antibodies can efficiently transport more antigens into the cells. This result confirmed that the V4 mutation in the scavenger antibody could enhance the binding of the antibody to hFcRn under neutral conditions. After the antigen-antibody complex entered into the cells, the intracellular pH was only about 6.0, the antibody was dissociated from the antigen-antibody complex and returned to the cell surface to perform the antigen-binding function again. The enhancement of ability to bind to hFcRn under neutral conditions for scavenger antibody could open the "convenience door" for subsequent pH-dependent antigen binding properties.

4.1.3 Determination of Therapeutic Effect of Scavenger Antibodies Capable of Binding to hFcRn in Animal Models The V4 modification was aimed at the hFcRn receptor. The receptor of HBV transgenic mice was mFcRn, which could not be used to evaluate the effect of modification. Therefore, the model of hFcRn transgenic mice infected with rAAV-HBV adr was adopted. The hFcRn transgenic mice aged 6 to 8 weeks (purchased from Biosaitu) were subjected to single injection of an appropriate dose of rAAV-HBV adr (purchased from Beijing Wujiahe Molecular Medicine Institute Co., Ltd.) via tail vein. The HBV virus titer in the mice were monitored for four consecutive weeks. After the virus titer was stable, the hFcRn transgene mice with stable HBV virus titer (4 in each group) were injected via tail vein with two scavenger antibodies, M1D and negative control 16G12 respectively, at a single dose of 20 mg/kg, and assisted with intraperitoneal injection of anti-CD4 antibody to suppress humoral immune response. Then the concentrations of HBsAg, antibody and HBV DNA in serum were measured to analyze the in vivo antigen clearance rate and antibody half-life of the scavenger antibodies.

4.1.3.1 Quantitative Detection of HBsAg

Figure 13A:
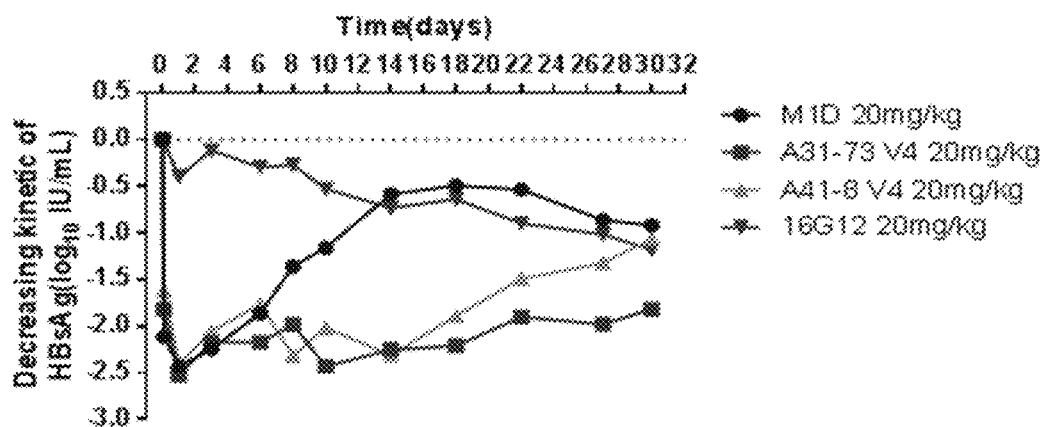
FIGS. 13A to 13C show the therapeutic effects of the two scavenger antibodies A31-73 V4 and A41-8 V4, M1D and negative control 16G12 by single injection via tail vein at dose of 20 mg/kg in hFcRn transgenic mice with stable HBV virus titer in Example 4.

The specific steps were shown in Example 3.2.1, and the detection results of A31-73 V4 and A41-8 V4 were shown in FIG. 13A.

4.1.3.2 Quantitative Detection of Antibodies in Serum

Figure 13B:
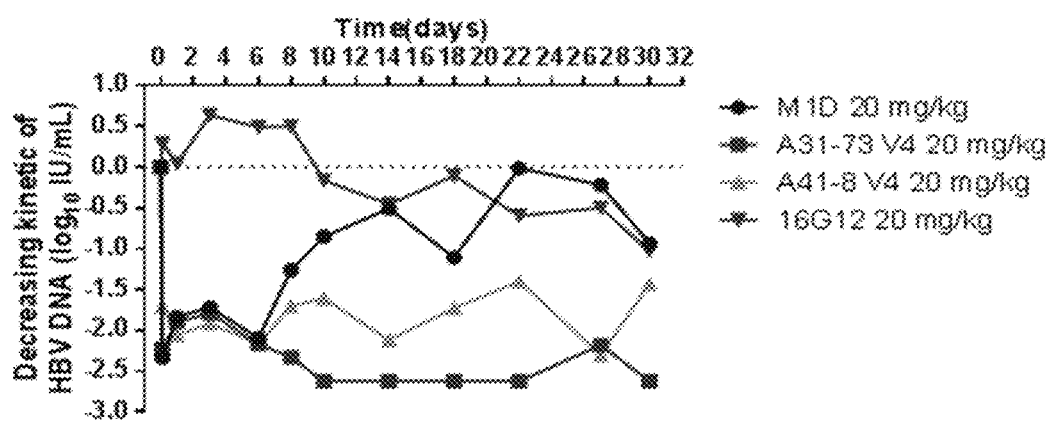

The specific steps were shown in Example 3.2.2, and the detection results of A31-73 V4 and A41-8 V4 were shown in FIG. 13B.

4.1.3.3 Quantitative Detection of HBV DNA

The quantitative detection of HBV DNA was carried out in accordance with the instructions of the HBV DNA real-time fluorescence quantitative detection kit (the kit was purchased from Beijing Jinmaige Biotechnology Co., Ltd.).

In this example, the virus clearance abilities of A31-73 V4, A41-8 V4 and the reference antibody M1D in animals were determined. The experimental results were shown in FIG. 13C.

Figure 13C:
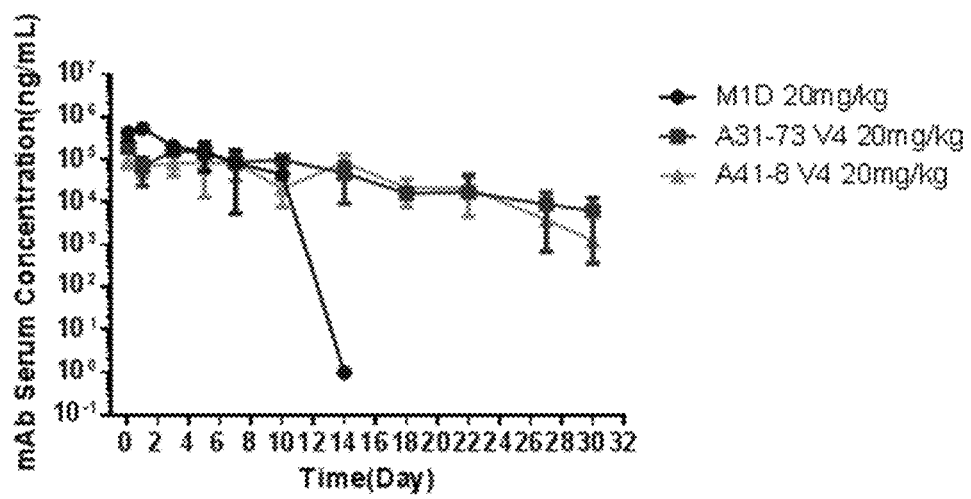

The results of FIGS. 13A to 13C showed that scavenger antibodies A31-73 V4 and A41-8 V4 had antigen clearance capabilities comparable to that of M1D, but had a longer inhibition time. After M1D exerted the maximum antigen clearance effect, the antigen rebound started quickly, and M1D started to fail on the 14$^{th}$ day and the HBsAg in serum returned to the baseline level (based on the negative control 16G12). However, the 2 scavenger antibodies could still maintain a lower antigen level for a long-term after exerting the maximum clearance effect, and rebound slowly. In the A41-8 V4 treatment group, HBsAg rebounded back to the baseline in about 30 days. In the A31-73 V4 treatment group, it did not return to the baseline level after the expected end of the experiment. These was consistent with the detection results of antibody half-life in serum. Such technical effects are remarkable and unexpected.

Figure 14:
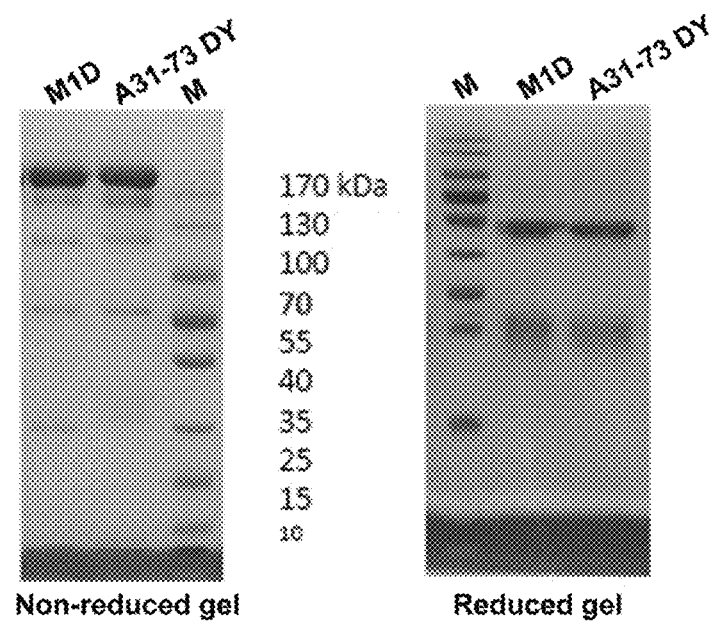
FIG. 14 shows the protein gel results of A31-73 DY in Example 4, and M1D is a positive control. It can be seen from the results that all antibodies are single-component.

4.2 Scavenger Antibody Capable of Binding to mFcγRII 4.2.1 Construction. Expression and Purification of Scavenger Antibody Capable of Binding to mFcγRII The A31-73 and A41-8 with the best performance in HBV transgenic mice in Example 3 were subjected to DY (K326D, L328Y) mutation on Fc region (this work was commissioned to General Biology, order number: G120460) to obtain A31-73 DY and A41-8 DY respectively, the heavy chain constant region after mutation was shown in SEQ ID NO:48. The antibodies was subjected to large-scale eukaryotic expression and purification, the specific operation steps of which were shown in Examples 2.2 and 2.3. The protein gel results of A31-73 DY were shown in FIG. 14. The results showed that the antibody are single-component.

Figure 15:
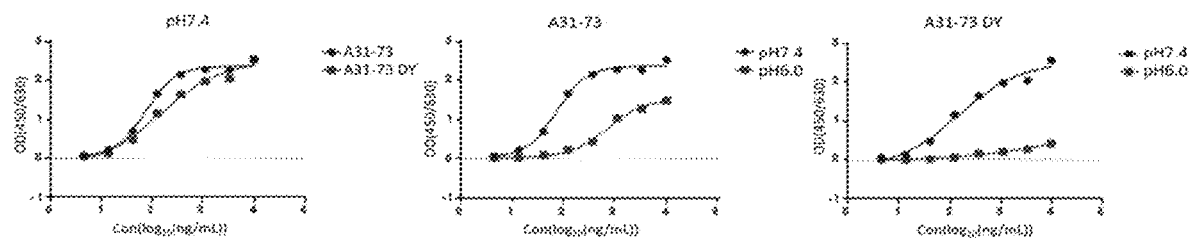
FIG. 15 shows the detection results of A31-73 DY binding to HBsAg at pH 7.4 and pH 6.0 in Example 4, wherein the abscissa represents the antibody concentration (Log10 ng/ml), and the ordinate represents the OD value. The results show that A31-73 DY can maintain the antigen-binding activity and pH-dependent antigen-binding activity at neutral pH of the parent antibody, and the pH-dependent antigen-binding activity is slightly enhanced.

4.2.2 In Vitro Activity Detection of Scavenger Antibody Capable of Binding to mFcγRII 4.2.2.1 Determination of antigen binding activity of scavenger antibodies capable of binding to mFcγRII at different pH The antigen binding activities of A31-73 DY at pH 7.4 and pH 6.0 were detected respectively, specific operation steps of which are shown in Example 3.1. The results were shown in FIG. 15. The A31-73 DY could maintain an antigen-binding activity and pH-dependent antigen-binding activity equivalent to those of the parent antibody at neutral pH, and the antigen-binding activity at acidic pH was further weakened, indicating the pH-dependent antigen-binding activity of A31-73 DY was enhanced to a certain extent.

4.2.2.2 Functional Verification at Cellular Level of Scavenger Antibodies Capable of Binding to mFcγRII 4.2.2.2.1 Labeling HBsAg with 488 Fluorescence Specific steps were shown in 4.1.2.2.1.

4.2.2.2.2 Immunofluorescence Experiment Based on Mouse Primary Macrophages (1) 4 days before the experiment, 1.5 mL of 3% sodium thioglycolate solution was injected into the abdominal cavity of each mouse, but not injected into the intestine;

(2) two mice were executed and soaked in 75% alcohol for 3 minutes;

(3) the mouse was horizontally fixed on a foam board to expose the abdomen; the abdominal skin was cut with tissue scissors, the peritoneum was disinfected and incised to expose the abdominal cavity, the abdominal incision skin was pulled by two toothed forceps hold in the left hand and fixed, 1640 culture medium was pipetted by Pasteur pipette hold in the right hand for peritoneal lavage with 4 mL/time, for a total of two times. The pipette was used to gently and fully stir the abdominal cavity to make the lavage more fully and thoroughly. After fully stirring for about 2 minutes and standing for about 5 minutes to fully isolate the macrophages, the lavage solution was pipetted and transferred into a centrifuge tube;

(4) 4° C., 1100 g, 5 min;

(5) the supernatant was carefully discarded, the cells were washed twice with 1640 medium, centrifuged at 4° C., 1100 g for 5 min, the supernatant was discarded, and the cells were resuspended in RPM1640;

(6) after counting the cells, the cells were adjusted to have a density of 10$^6$ cells/mL, cultured on a 24-well glass-bottom cell imaging culture plate, 250 μL/well, the medium was changed after 2 hours, the washing was performed once with RPM1640, the non-adherent cells were discarded, and then incubation was performed overnight in a 37° C., $CO_2$ incubator;

(7) the antibody and antigen labeled with corresponding fluorescence were diluted in serum-free medium to: 800 ng/mL for antigen, and 20 μg/mL for antibody;

(8) 125 μL each of the antigen and antibody were mixed uniformly, and then allowed to stand for 1 hour in a 37° C., $CO_2$ incubator;

(9) the cell supernatant in the cell imaging culture plate was discarded, the antigen-antibody complex was added, shaken evenly, and allowed to stand in a $CO_2$ incubator at 37° C. for 2 hours;

(10) the supernatant was discarded, and 1 mL of sterile PBS incubated at 37° C. in advance was used to "wash" the cell surface 3 to 5 times, and removed by pipetting;

(11) Dio was diluted at 1:2000, added at an amount to submerge the cells, and allowed to stand at room temperature for 20 min;

(12) the supernatant was discarded, and 1 mL of sterile PBS incubated at 37° C. in advance was used to "wash" the cell surface 3 to 5 times, and removed by pipetting;

(13) the live cell nuclear dye (2 drops were added to 1 mL volume) was added, allowed to stand at room temperature for 20 min, and placed in a high-content imager for imaging.

Figure 16:
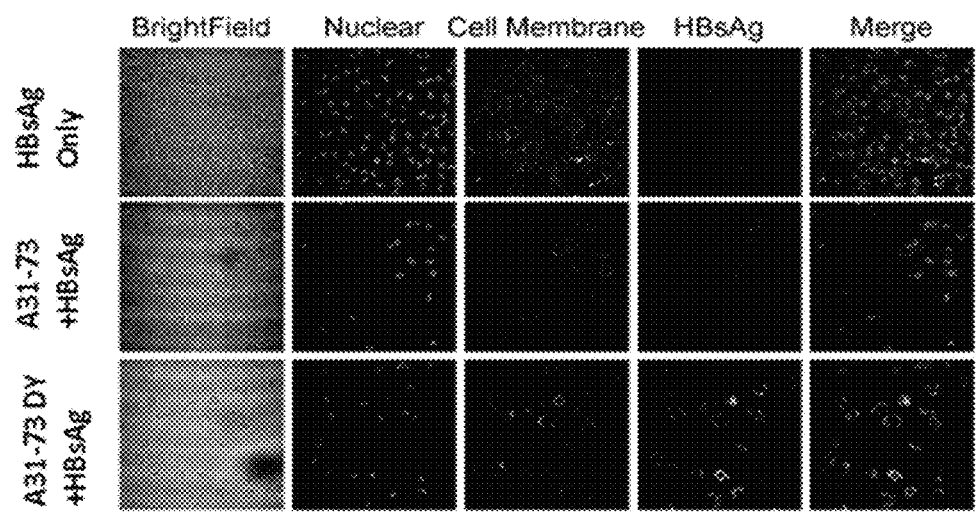
FIG. 16 shows the results of immunofluorescence experiment for A31-73 DY and A31-73 on murine primary macrophages in Example 4, wherein the green fluorescence represents hFcRn, the blue fluorescence represents the nucleus, and the red fluorescence represents HBsAg. The results show that the DY modification enhances the phagocytosis of antigen-antibody complexes by murine macrophages.
Figure 17A:
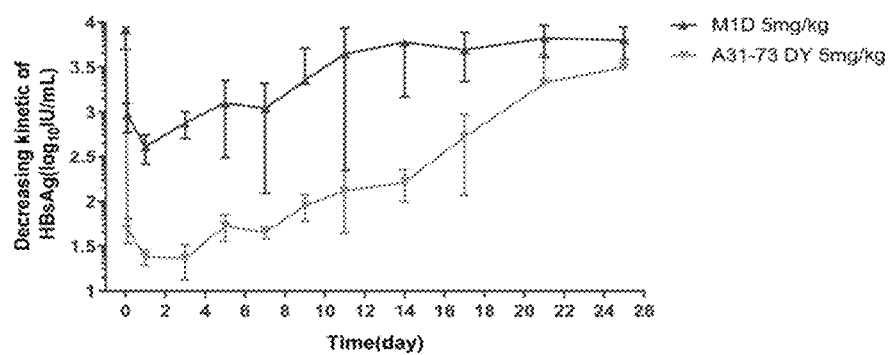
FIGS. 17A to 17C show the therapeutic effects of A31-73 DY scavenger antibody and MID in Example 4 after single injection via tail vein at dose of 5 mg/kg in HBV transgenic mice.
Figure 17B:
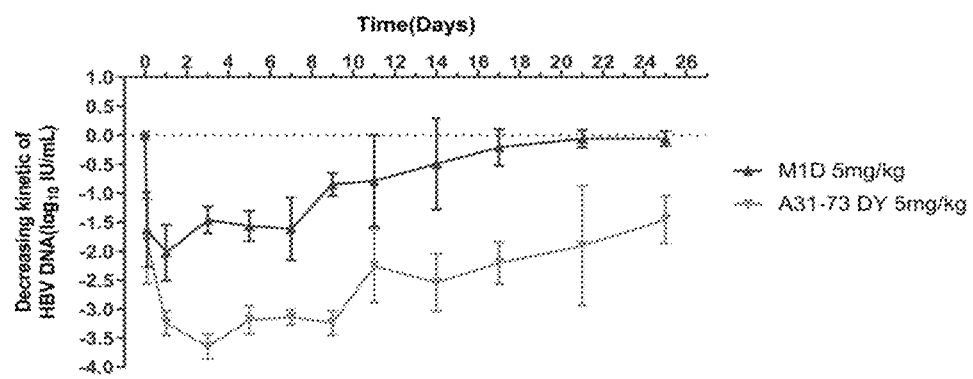
Figure 17C:
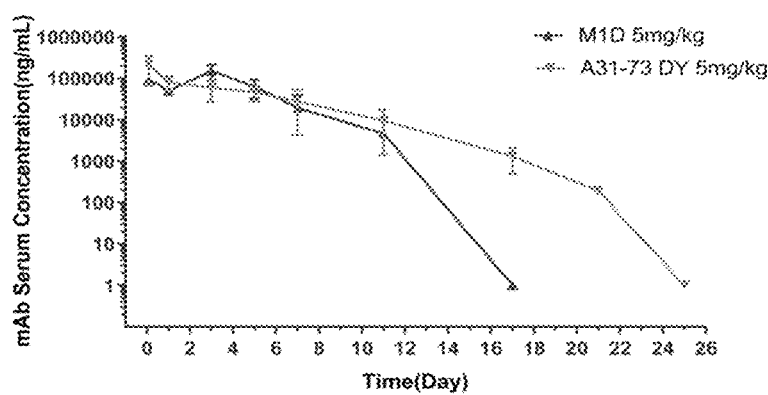

The results of the experiment were shown in FIG. 16. It could be seen from the results that the DY modification enhanced the phagocytosis of antigen-antibody complex by mouse macrophages, leading to more antigen degradation.

4.2.3 Determination of Therapeutic Effect of Scavenger Antibody Capable of Binding to mFcγRII in Animal Model 4.2.3.1 Evaluation of Therapeutic Effect of Scavenger Antibody in Transgenic Mice HBV transgenic mice aged 6-8 weeks were selected, and injected with A31-73 DY scavenger antibody and M1D via tail vein at a single dose of 5 mg/kg (4 mice per group). By detecting the concentrations of HBsAg, antibody and HBV DNA in serum, the in vivo antigen clearance rate and antibody half-life of scavenger antibody were analyzed.

4.2.3.1.1 Quantitative Detection of HBsAg

The specific steps were shown in Example 3.2.1, and the detection results of A31-73 DY were shown in FIG. 17A.

4.2.3.1.2 Quantitative Detection of HBV DNA

The quantitative detection of HBV DNA was carried out in accordance with the instructions of the HBV DNA real-time fluorescence quantitative detection kit (the kit was purchased from Beijing Jinmaige Biotechnology Co., Ltd.).

In this example, the virus clearance abilities of A31-73 DY and reference antibody M1D in animals were determined. The experimental results were shown in FIG. 17B.

4.2.3.1.3 Quantitative Detection of Antibody in Serum

The specific steps were shown in Example 3.2.2, and the detection results of A31-73 DY were shown in FIG. 17C.

The results of FIGS. 17A to 17C showed that the scavenger antibody A31-73 DY with DY modification was more than an order of magnitude stronger than M1D in antigen clearance ability. The A31-73 DY could not only quickly clear HBsAg in HBV transgenic mice (FIG. 17A), but also effectively reduce the HBV DNA titer in mice (FIG. 17B), which was consistent with the detection result of antibody half-life in serum (FIG. 17C). Comparing the antibody concentrations in the serum, the half-life of A31-73 DY was longer than that of M1D by nearly 12 days, which showed that the scavenger antibody A31-73 DY had the function of reciprocally binding antigen, thereby increasing the time of antigen clearance.

4.2.3.2 Evaluation of Therapeutic Effect of Scavenger Antibody in HBV Mouse Model Transfected with Adeno-Associated Virus As shown in FIG. 18A, 4-6 weeks old C57 mice were injected with $1 \times 10^{11}$ rAAV8-1.3HBV adr to establish an HBV mouse model generated by transfection by adeno-associated virus (Day −28), and the mouse virus titer was continuously monitored. After the virus titer became stable, the baseline HBsAg level in mice was detected and the mice were divided into groups (Day −1). scavenger antibody A31-73 DY (73 DY for short) and the negative control 16G12 were injected at a dose of 5 mg/kg, for 5 times; all mice were sacrificed 2 weeks after the $5^{th}$ treatment, the mouse serum was collected, and the serum HBsAg and Anti-HBs levels were analyzed.

4.2.3.2.1 Quantitative Detection of HBsAg

Figure 18A:
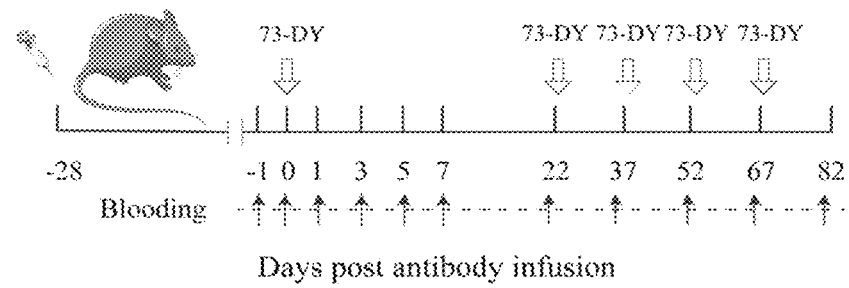
FIGS. 18A to 18C show the therapeutic effect of scavenger antibody A31-73 DY and negative control 16G12 in Example 4 after the injection of scavenger antibody at a dose of 5 mg/kg for 5 times in an HBV mouse model which is obtained by transfection by adeno-associated virus.
Figure 18B:
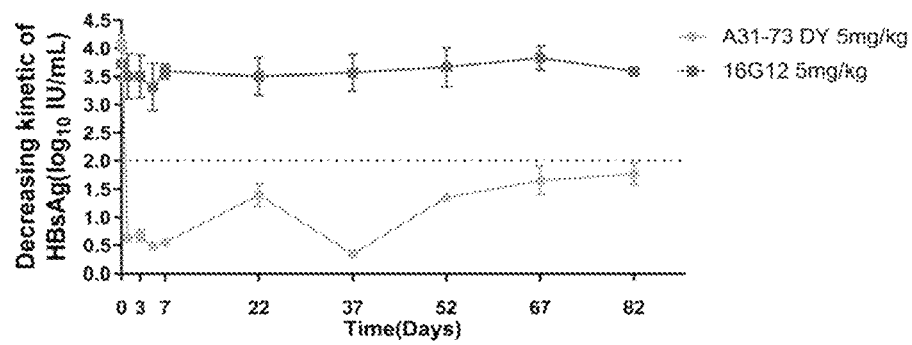

The specific steps were shown in Example 3.2.1, and the detection results of A31-73DY were shown in FIG. 18B.

4.2.3.2.2 Qualitative Detection of Anti-HBs (1) Sample dilution: the serum sample was diluted with 20% NBS into 5 gradients: 100 times, 500 times, 2500 times, 12500 times and 62500 times;

(3) Sample addition: 100 μL/well of the sample diluted in the previous step and the corresponding antibody diluent were added to a commercial HBsAb plate (purchased from Beijing Wantai), and incubated at 37° C. for 1 h.

(4) Washing: the plate was washed 5 times with 300 μL/well of PBST by a plate washer and spin-dried;

(5) Adding enzyme-labeled secondary antibody: 100 μL/well of GAM-HRP-labeled secondary antibody diluent was added, and incubated at 37° C. for 30 min;

(6) Washing: the plate was washed 5 times with 300 μL/well of PBST by a plate washer, and spin-dried;

(7) Color development: 100 μL/well of color development solution, 37° C., 10-15 min;

(8) Stop and read: 50 μL/well stop solution was added, the reading value was measured by a microplate reader at OD450/630 within 10 minutes.

(9) Calculation of Anti-HBs concentration in mouse serum sample: the reading value between 0.1 and 1 was multiplied by the dilution factor, and its logarithmic value ($\log_{10}$) was taken.

Figure 18C:
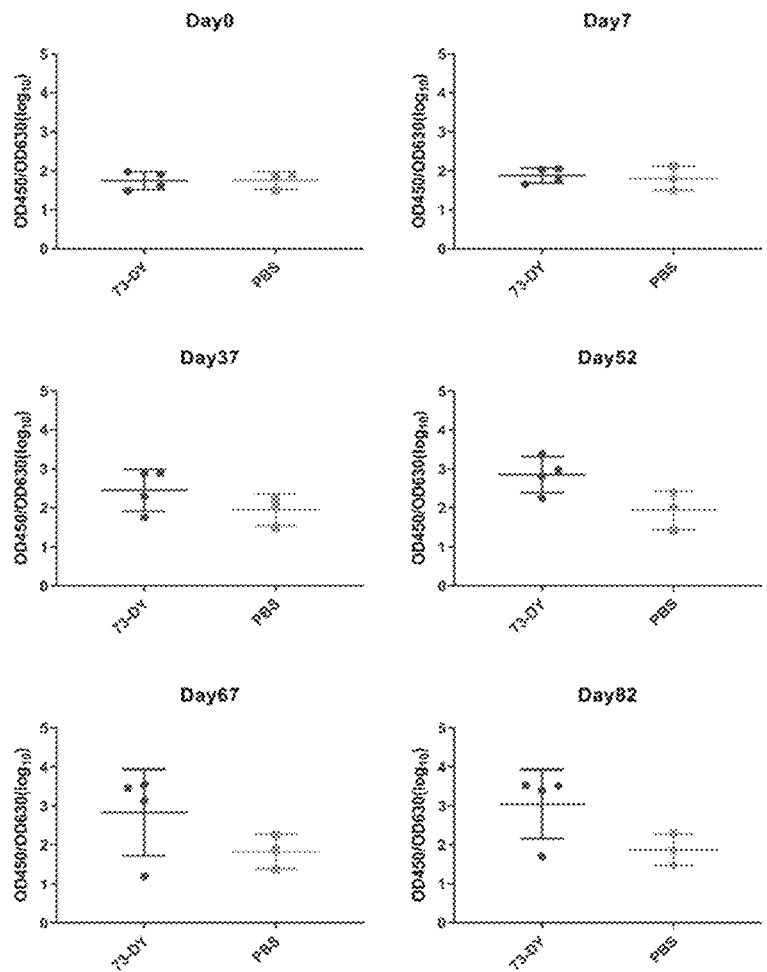

The detection results of Anti-HBs level in mouse serum after antibody treatment were shown in FIG. 18C.

The results of FIG. 18B showed that the scavenger antibody A31-73 DY could control the HBsAg level in the HBV mice model generated by adeno-associated virus below 100 IU/ml for a long time with a dose of 5 mg/kg and a dosing frequency of 15 days/injection. The results of FIG. 18C showed the Anti-HBs levels in mice on days 0, 7, 37, 52, 67 and 82, and it could be seen that the A31-73 DY antibody-treated mice had higher Anti-HBs levels, 3 out of 4 mice produced obvious Anti-HBs (only the mice continuously treated to the end were counted), indicating that the production of Anti-HBs could be related to the continuous inhibition of HBsAg. This showed that the scavenger antibody A31-73 DY broke through the limitations of traditional antibodies and achieved low-dose, low-frequency treatment; and more importantly, after long-term treatment, the humoral immune response in mice was activated that allowed the production of Anti-HBs.

Example 5: Affinity Determination of M1D, A31-73 and A41-8

HBsAg was dissolved in sodium acetate (pH 4.5) at 5 μg/mL, and the chip coating program was run on the Biacore 3000 device to coat HBsAg on the CM5 chip. The coating volume of HBsAg was 2400RU. The analyte was diluted 2-fold from 100 nM to prepare samples of 7 concentrations. The affinity determination program was run on the Biacore 3000 device, the flow rate was set to 50 μL/min, the binding time was set to 90 s, the dissociation time was set to 600 s, the temperature of sample chamber was set to 10° C., the regeneration solution was 50 mM NaOH, the regeneration flow rate was set to 50 μL/min, and the regeneration time was set to 60 s. The results were summarized in Table 7.

TABLE 7

Affinity determination of M1D, A31-73 and A41-8

| | KD(M) in pH 7.4 | KD(M) in pH 6.0 | KD(pH 6.0)/KD(pH 7.4) |
|---|---|---|---|
| M1D | 5.34E−10 | | |
| A31-73 | 7.3E−10 | 3.62E−09 | 4.95 |
| A41-8 | 1.68E−09 | 1.93E−09 | 1.15 |

Although the specific embodiments of the present invention have been described in detail, those skilled in the art will understand that according to all the teachings that have been published, various modifications and changes can be made to the details, and these changes are within the protection scope of the present invention. All of the present invention is given by the appended claims and any equivalents thereof.

What is claimed is:

1. An antibody or antigen-binding fragment thereof capable of specifically binding to HBsAg, wherein the antibody or antigen-binding fragment thereof binds to HBsAg with higher affinity at neutral pH than at acidic pH, and the antibody or antigen-binding fragment thereof comprises:

(1) a VH comprising three CDRs:
HCDR1 consisting of the amino acid sequence of SEQ ID NO:8,
HCDR2 consisting of the amino acid sequence of SEQ ID NO: 9, and
HCDR3 consisting of the amino acid sequence of SEQ ID NO: 10;
and
a VL comprising three CDRs:
LCDR1 consisting of the amino acid sequence of SEQ ID NO: 11,
LCDR2 consisting of the amino acid sequence of SEQ ID NO: 12, and
LCDR3 consisting of the amino acid sequence of SEQ ID NO: 13;
(2) a VH comprising three CDRs:
HCDR1 consisting of the amino acid sequence of SEQ ID NO: 14,
HCDR2 consisting of the amino acid sequence of SEQ ID NO: 15, and
HCDR3 consisting of the amino acid sequence of SEQ ID NO: 16;
and
a VL comprising three CDRs:
LCDR1 consisting of the amino acid sequence of SEQ ID NO: 11,
LCDR2 consisting of the amino acid sequence of SEQ ID NO: 12, and
LCDR3 consisting of the amino acid sequence of SEQ ID NO: 13;
(3) a VH comprising three CDRs:
HCDR1 consisting of the amino acid sequence of SEQ ID NO: 20,
HCDR2 consisting of the amino acid sequence of SEQ ID NO: 21, and
HCDR3 consisting of the amino acid sequence of SEQ ID NO: 22;
and
a VL comprising three CDRs:
LCDR1 consisting of the amino acid sequence of SEQ ID NO: 23,
LCDR2 consisting of the amino acid sequence of SEQ ID NO: 12, and
LCDR3 consisting of the amino acid sequence of SEQ ID NO: 13;
or
(4) a VH comprising three 3 CDRs:
HCDR1 consisting of the amino acid sequence of SEQ ID NO: 17,
HCDR2 consisting of the amino acid sequence of SEQ ID NO: 18, and
HCDR3 consisting of the amino acid sequence of SEQ ID NO: 10;
and
a VL comprising three CDRs:
LCDR1 consisting of the amino acid sequence of SEQ ID NO: 19,
LCDR2 consisting of the amino acid sequence of SEQ ID NO: 12, and
LCDR3 consisting of the amino acid sequence of SEQ ID NO: 13.

2. The antibody or antigen-binding fragment thereof according to claim 1, wherein the antibody or antigen-binding fragment thereof further comprises a framework region of a human immunoglobulin, and the framework region optionally comprises at least one back mutation from human residues to murine residues.

3. The antibody or antigen-binding fragment thereof according to claim 1, wherein the antibody or antigen-binding fragment thereof comprises:
(1) a VH consisting of the amino acid sequence of SEQ ID NO: 1 and a VL consisting of the amino acid sequence of SEQ ID NO: 2;
(2) a VH consisting of the amino acid sequence of SEQ ID NO: 3 and a VL consisting of the amino acid sequence of SEQ ID NO: 2;
(3) a VH consisting of the amino acid sequence of SEQ ID NO: 4 and a VL consisting of the amino acid sequence of SEQ ID NO: 5; or
(4) a VH consisting of the amino acid sequence of SEQ ID NO: 6 and a VL consisting of the amino acid sequence of SEQ ID NO: 7.

4. The antibody or antigen-binding fragment thereof according to claim 1, wherein the antibody or antigen-binding fragment thereof further comprises a constant region derived from a human immunoglobulin.

5. The antibody or antigen-binding fragment thereof according to claim 4, wherein the antibody or antigen-binding fragment thereof comprises a variant of a human IgGI heavy chain constant region, the variant has the following substitution as compared to a wild-type sequence from which it is derived: (i) M252Y, N286E, N434Y; or, (ii) K326D, L328Y; wherein the amino acid positions are positions according to the Kabat numbering system.

6. The antibody or antigen-binding fragment thereof according to claim 1, wherein the antibody or antigen-binding fragment thereof comprises:
(1) a heavy chain comprising a VH consisting of the amino acid sequence of SEQ ID NO: 1 and a CH consisting of the amino acid sequence of SEQ ID NO: 57, and a light chain comprising a VL consisting of the amino acid sequence of SEQ ID NO: 2 and a CL consisting of the amino acid sequence of SEQ ID NO: 58;
(2) a heavy chain comprising a VH consisting of the amino acid sequence of SEQ ID NO: 1 and a CH consisting of the amino acid sequence of SEQ ID NO: 47, and a light chain comprising a VL consisting of the amino acid sequence of SEQ ID NO: 2 and a CL consisting of the amino acid sequence of SEQ ID NO: 58;
(3) a heavy chain comprising a VH consisting of the amino acid sequence of SEQ ID NO: 1 and a CH consisting of the amino acid sequence of SEQ ID NO: 48, and a light chain comprising a VL consisting of the amino acid sequence of SEQ ID NO: 2 and a CL consisting of the amino acid sequence of SEQ ID NO: 58;
(4) a heavy chain comprising a VH consisting of the amino acid sequence of SEQ ID NO: 3 and a CH consisting of the amino acid sequence of SEQ ID NO: 57, and a light chain comprising a VL consisting of the amino acid sequence of SEQ ID NO: 2 and a CL consisting of the amino acid sequence of SEQ ID NO: 58;

(5) a heavy chain comprising a VH consisting of the amino acid sequence of SEQ ID NO: 3 and a CH consisting of the amino acid sequence of SEQ ID NO: 47, and a light chain comprising a VL consisting of the amino acid sequence of SEQ ID NO: 2 and a CL consisting of the amino acid sequence of SEQ ID NO: 58;

(6) a heavy chain comprising a VH consisting of the amino acid sequence of SEQ ID NO: 3 and a CH consisting of the amino acid sequence of SEQ ID NO: 48, and a light chain comprising a VL consisting of the amino acid sequence of SEQ ID NO: 2 and a CL consisting of the amino acid sequence of SEQ ID NO: 58;

(7) a heavy chain comprising a VH consisting of the amino acid sequence of SEQ ID NO: 4 and a CH consisting of the amino acid sequence of SEQ ID NO: 57, and a light chain comprising a VL consisting of the amino acid sequence of SEQ ID NO: 5 and a CL consisting of the amino acid sequence of SEQ ID NO: 58;

(8) a heavy chain comprising a VH consisting of the amino acid sequence of SEQ ID NO: 4 and a CH consisting of the amino acid sequence of SEQ ID NO: 47, and a light chain comprising a VL consisting of the amino acid sequence of SEQ ID NO: 5 and a CL consisting of the amino acid sequence of SEQ ID NO: 58;

(9) a heavy chain comprising a VH consisting of the amino acid sequence of SEQ ID NO: 4 and a CH consisting of the amino acid sequence of SEQ ID NO: 48, and a light chain comprising a VL consisting of the amino acid sequence of SEQ ID NO: 5 and a CL consisting of the amino acid sequence of SEQ ID NO: 58;

(10) a heavy chain comprising a VH consisting of the amino acid sequence of SEQ ID NO: 6 and a CH consisting of the amino acid sequence of SEQ ID NO: 57, and a light chain comprising a VL consisting of the amino acid sequence of SEQ ID NO: 7 and a CL consisting of the amino acid sequence of SEQ ID NO: 58;

(11) a heavy chain comprising a VH consisting of the amino acid sequence of SEQ ID NO: 6 and a CH consisting of the amino acid sequence of SEQ ID NO: 47, and a light chain comprising a VL consisting of the amino acid sequence of SEQ ID NO: 7 and a CL consisting of the amino acid sequence of SEQ ID NO: 58; or

(12) a heavy chain comprising a VH consisting of the amino acid sequence of SEQ ID NO: 6 and a CH consisting of the amino acid sequence of SEQ ID NO: 48, and a light chain comprising a VL consisting of the amino acid sequence of SEQ ID NO: 7 and a CL consisting of the amino acid sequence of SEQ ID NO: 58.

7. The antibody or antigen-binding fragment thereof according to claim 1, wherein the antibody or antigen-binding fragment thereof is selected from the group consisting of scFv, Fab, Fab', (Fab')$_2$, Fv fragment, diabody, bispecific antibody, multispecific antibody, probody, chimeric antibody and humanized antibody.

8. An isolated nucleic acid molecule, which encodes the antibody or antigen-binding fragment thereof according to claim 1, or its heavy chain variable region and light chain variable region.

9. A vector, which comprises an isolated nucleic acid molecule encoding the antibody or antigen-binding fragment thereof according to claim 1 or its heavy chain variable region and light chain variable region.

10. A host cell, comprising: (i) an isolated nucleic acid molecule encoding the antibody or antigen-binding fragment thereof according to claim 1 or its heavy chain variable region and light chain variable region, or (ii) a vector comprising the isolated nucleic acid molecule.

11. A method for preparing the antibody or antigen-binding fragment thereof according to claim 1, the method comprising:
culturing a host cell comprising an isolated nucleic acid molecule encoding the antibody or antigen-binding fragment thereof under a condition that allows the expression of the antibody or antigen-binding fragment thereof, and
recovering the antibody or antigen-binding fragment thereof from the cultured host cell culture.

12. A pharmaceutical composition, comprising the antibody or antigen-binding fragment thereof according to claim 1, and a pharmaceutically acceptable carrier and/or excipient.

13. A method for treatment of an HBV infection or HBV infection-associated disease in a subject, for neutralizing a virulence of HBV in a subject, for reducing a serum level of HBV DNA and/or HBsAg in a subject, and/or for activating a humoral immune response against HBV in a subject, the method comprising:
administering an effective amount of the antibody or antigen-binding fragment thereof according to claim 1, or a pharmaceutical composition comprising the antibody or antigen-binding fragment thereof, to a subject in need thereof.

14. The antibody or antigen-binding fragment thereof according to claim 2, wherein:
(i) the antibody or antigen-binding fragment thereof comprises:
a heavy chain framework region contained in an amino acid sequence encoded by IGHV4-4*08, and
a light chain framework region contained in an amino acid sequence encoded by IGKV1-39*01,
wherein the heavy chain framework region and/or the light chain framework region optionally comprises at least one back mutation from human residues to murine residues; or,
(ii) the VH of the antibody or antigen-binding fragment thereof comprises:
a VH FR1 consisting of the amino acid sequence of SEQ ID NO: 24,
a VH FR2 consisting of the amino acid sequence of SEQ ID NO: 25,
a VH FR3 consisting of the amino acid sequence of SEQ ID NO: 26, and
a VH FR4 consisting of the amino acid sequence of SEQ ID NO: 27;
and/or
the VL of the antibody or antigen-binding fragment thereof comprises:
a VL FR1 consisting of the amino acid sequence of SEQ ID NO: 28,
a VL FR2 consisting of the amino acid sequence of SEQ ID NO: 29,
a VL FR3 consisting of the amino acid sequence of SEQ ID NO: 30, and
a VL FR4 consisting of the amino acid sequence of SEQ ID NO: 31.

15. The antibody or antigen-binding fragment thereof according to claim 4, wherein:
(i) the antibody or antigen-binding fragment thereof comprises a heavy chain constant region (CH) consisting of the amino acid sequence of SEQ ID NO: 47 or 48 or 57; and/or,
(ii) the antibody or antigen-binding fragment thereof comprises a light chain constant region (CL) consisting of the amino acid sequence of SEQ ID NO: 58.

16. The method according to claim 13, wherein the subject is a human.

17. The method according to claim 13, wherein the subject is a person having chronic HBV infection or chronic hepatitis B.

* * * * *